US012806018B2

(12) United States Patent
Khairkhahan et al.

(10) Patent No.: US 12,806,018 B2
(45) **Date of Patent: *Nov. 24, 2026**

(54) MITRAL VALVE IMPLANTS FOR THE TREATMENT OF VALVULAR REGURGITATION

(71) Applicant: Polares Medical Inc., Palo Alto, CA (US)

(72) Inventors: Alexander K. Khairkhahan, Palo Alto, CA (US); Michael D. Lesh, Mill Valley, CA (US)

(73) Assignee: Polares Medical Inc., Palo Alto, CA (US)

( * ) Notice: Subject to any disclaimer, the term of this patent is extended or adjusted under 35 U.S.C. 154(b) by 0 days.

This patent is subject to a terminal disclaimer.

(21) Appl. No.: 18/616,839

(22) Filed: Mar. 26, 2024

(65) Prior Publication Data

US 2024/0341957 A1 Oct. 17, 2024

Related U.S. Application Data

(63) Continuation of application No. 16/705,605, filed on Dec. 6, 2019, now Pat. No. 11,974,921, which is a (Continued)

(51) Int. Cl.
*A61F 2/24* (2006.01)
*A61B 17/04* (2006.01)

(Continued)

(52) U.S. Cl.
CPC ........ *A61F 2/2466* (2013.01); *A61B 17/0401* (2013.01); *A61B 17/068* (2013.01);

(Continued)

(58) Field of Classification Search
CPC .... A61F 2/2466; A61F 2/2442; A61F 2/2454; A61F 2210/0014; A61B 17/068;

(Continued)

(56) References Cited

U.S. PATENT DOCUMENTS 3,491,376 A 1/1970 Shiley
3,503,079 A 3/1970 Smith (Continued)

FOREIGN PATENT DOCUMENTS

CN 102256568 12/2002
CN 1984621 6/2007

(Continued)

OTHER PUBLICATIONS

Biocina et al., Mitral Valve Repair With The New Mitrofast® Repair System, Dubrava University Hospital, Zagreb, Crotia, Mitrofast Abstract European Soc CVS 55th Congress—May 11-14, 2006 Suppl 1 to vol. 5.

(Continued)

*Primary Examiner* — Anh T Dang
(74) *Attorney, Agent, or Firm* — Knobbe, Martens, Olson & Bear, LLP

(57) ABSTRACT

The invention relates in some aspects to a device for use in the transcatheter treatment of mitral valve regurgitation, including steerable guidewires, implantable coaptation assistance devices, anchoring systems for attaching a ventricular projection of an implantable coaptation device, a kit, and methods of using an implantable coaptation assistance device among other methods.

19 Claims, 30 Drawing Sheets

Related U.S. Application Data continuation of application No. 14/742,199, filed on Jun. 17, 2015, now Pat. No. 10,500,048.

(60) Provisional application No. 62/014,060, filed on Jun. 18, 2014.

(51) Int. Cl.

| | |
|---|---|
| ***A61B 17/068*** | (2006.01) |
| *A61B 17/00* | (2006.01) |
| *A61B 17/06* | (2006.01) |
| *A61B 17/064* | (2006.01) |

(52) U.S. Cl.

CPC ....................... *A61F 2/2442* (2013.01); *A61B 2017/00323* (2013.01); *A61B 2017/0053* (2013.01); *A61B 2017/0409* (2013.01); *A61B 2017/0417* (2013.01); *A61B 2017/0441* (2013.01); *A61B 2017/0461* (2013.01); *A61B 2017/0464* (2013.01); *A61B 2017/06052* (2013.01); *A61B 2017/0641* (2013.01); *A61B 2017/0649* (2013.01); *A61F 2210/0014* (2013.01)

(58) Field of Classification Search

CPC ........ A61B 17/0401; A61B 2017/0417; A61B 2017/0464; A61B 2017/0014; A61B 2017/00323; A61B 2017/0053; A61B 2017/0409; A61B 2017/0441; A61B 2017/0461; A61B 2017/06052; A61B 2017/0641; A61B 2017/0649

See application file for complete search history.

(56) References Cited

U.S. PATENT DOCUMENTS

| | | | |
|---|---|---|---|
| 3,656,185 | A | 4/1972 | Carpentier |
| 3,671,979 | A | 6/1972 | Moulopoulos |
| 3,874,388 | A | 4/1975 | King et al. |
| 3,898,701 | A | 8/1975 | La Russa |
| 3,938,197 | A | 2/1976 | Milo |
| 4,007,743 | A | 2/1977 | Blake |
| 4,011,601 | A | 3/1977 | Clune et al. |
| 4,042,979 | A | 8/1977 | Angell |
| 4,078,268 | A | 3/1978 | Possis |
| 4,204,283 | A | 5/1980 | Bellhouse et al. |
| 4,218,783 | A | 8/1980 | Reul et al. |
| 4,261,342 | A | 4/1981 | Aranguren Duo |
| 4,263,680 | A | 4/1981 | Ruel et al. |
| 4,275,469 | A | 6/1981 | Gabbay |
| RE31,040 | E | 9/1982 | Possis |
| 4,352,211 | A | 10/1982 | Parravicini |
| 4,488,318 | A | 12/1984 | Kaster |
| 4,490,859 | A | 1/1985 | Black et al. |
| 4,491,986 | A | 1/1985 | Gabbay |
| 4,561,129 | A | 12/1985 | Arpesella |
| 4,687,483 | A | 8/1987 | Fisher et al. |
| 4,705,516 | A | 11/1987 | Barone et al. |
| 4,759,758 | A | 7/1988 | Gabbay |
| 4,790,843 | A | 12/1988 | Carpentier et al. |
| 4,960,424 | A | 10/1990 | Grooters |
| 4,994,077 | A | 2/1991 | Dobben |
| 5,002,567 | A | 3/1991 | Bona et al. |
| 5,078,737 | A | 1/1992 | Bona et al. |
| 5,131,905 | A | 7/1992 | Grooters |
| 5,197,980 | A | 3/1993 | Gorshkov et al. |
| 5,217,484 | A | 6/1993 | Marks |
| 5,258,023 | A | 11/1993 | Reger |
| 5,332,402 | A | 7/1994 | Teitelbaum |
| 5,344,442 | A | 9/1994 | Deac |
| 5,370,662 | A | 12/1994 | Stone et al. |
| 5,397,347 | A | 3/1995 | Cuilleron et al. |
| 5,397,348 | A | 3/1995 | Campbell et al. |
| 5,413,599 | A | 5/1995 | Imachi et al. |
| 5,487,760 | A | 1/1996 | Villafana |
| 5,500,015 | A | 3/1996 | Deac |
| 5,522,886 | A | 6/1996 | Milo |
| 5,554,186 | A | 9/1996 | Guo et al. |
| 5,582,616 | A | 12/1996 | Bolduc et al. |
| 5,593,435 | A | 1/1997 | Carpentier et al. |
| 5,626,613 | A | 5/1997 | Schmieding |
| 5,658,313 | A | 8/1997 | Thal |
| 5,662,683 | A | 9/1997 | Kay |
| 5,662,704 | A | 9/1997 | Gross |
| 5,716,370 | A | 2/1998 | Williamson, IV et al. |
| 5,733,331 | A | 3/1998 | Peredo |
| 5,824,065 | A | 10/1998 | Gross |
| 5,824,066 | A | 10/1998 | Gross |
| 5,824,067 | A | 10/1998 | Gross |
| 5,855,601 | A | 1/1999 | Bessler et al. |
| 5,888,240 | A | 3/1999 | Carpentier et al. |
| 5,957,949 | A | 9/1999 | Leonhardt et al. |
| 6,007,577 | A | 12/1999 | Vanney et al. |
| 6,024,096 | A | 2/2000 | Buckberg |
| 6,042,607 | A | 3/2000 | Williamson, IV et al. |
| 6,045,497 | A | 4/2000 | Schweich et al. |
| 6,045,573 | A | 4/2000 | Wenstrom et al. |
| 6,063,114 | A | 5/2000 | Nash et al. |
| 6,066,160 | A | 5/2000 | Colvin et al. |
| 6,086,612 | A | 7/2000 | Jansen |
| 6,113,631 | A | 9/2000 | Jansen |
| 6,162,233 | A | 12/2000 | Williamson, IV et al. |
| 6,217,610 | B1 | 4/2001 | Carpentier et al. |
| 6,221,104 | B1 | 4/2001 | Buckberg et al. |
| 6,250,308 | B1 | 6/2001 | Cox |
| 6,264,602 | B1 | 7/2001 | Mortier et al. |
| 6,287,339 | B1 | 9/2001 | Vazquez et al. |
| 6,296,662 | B1 | 10/2001 | Caffey |
| 6,299,637 | B1 | 10/2001 | Shaolian et al. |
| 6,312,447 | B1 | 11/2001 | Grimes |
| 6,312,464 | B1 | 11/2001 | Navia |
| 6,332,893 | B1 | 12/2001 | Mortier et al. |
| 6,358,277 | B1 | 3/2002 | Duran |
| 6,383,147 | B1 | 5/2002 | Stobie |
| 6,391,053 | B1 | 5/2002 | Brendzel et al. |
| 6,391,054 | B2 | 5/2002 | Carpentier et al. |
| 6,402,679 | B1 | 6/2002 | Mortier et al. |
| 6,402,780 | B2 | 6/2002 | Williamson, IV et al. |
| 6,409,758 | B2 | 6/2002 | Stobie et al. |
| 6,419,695 | B1 | 7/2002 | Gabbay |
| 6,439,237 | B1 | 8/2002 | Buckberg et al. |
| 6,450,171 | B1 | 9/2002 | Buckberg et al. |
| 6,451,024 | B1 | 9/2002 | Thompson et al. |
| 6,454,799 | B1 | 9/2002 | Schreck |
| 6,458,153 | B1 | 10/2002 | Bailey et al. |
| 6,482,228 | B1 | 11/2002 | Norred |
| 6,540,782 | B1 | 4/2003 | Snyders |
| 6,544,167 | B2 | 4/2003 | Buckberg et al. |
| 6,551,302 | B1 | 4/2003 | Rosinko et al. |
| 6,565,603 | B2 | 5/2003 | Cox |
| 6,569,198 | B1 | 5/2003 | Wilson |
| 6,602,288 | B1 | 8/2003 | Cosgrove et al. |
| 6,602,289 | B1 | 8/2003 | Colvin et al. |
| 6,626,930 | B1 | 9/2003 | Allen et al. |
| 6,629,534 | B1 | 10/2003 | St. Goar et al. |
| 6,652,578 | B2 | 11/2003 | Bailey et al. |
| 6,676,698 | B2 | 1/2004 | McGuckin, Jr. et al. |
| 6,682,559 | B2 | 1/2004 | Myers et al. |
| 6,702,852 | B2 | 3/2004 | Stobie et al. |
| 6,719,790 | B2 | 4/2004 | Brendzel et al. |
| 6,752,813 | B2 | 6/2004 | Goldfarb et al. |
| 6,764,510 | B2 | 7/2004 | Vidlund et al. |
| 6,780,200 | B2 | 8/2004 | Jansen |
| 6,790,237 | B2 | 9/2004 | Stinson |
| 6,797,002 | B2 | 9/2004 | Spence et al. |
| 6,800,090 | B2 | 10/2004 | Alferness et al. |
| 6,805,710 | B2 | 10/2004 | Bolling et al. |
| 6,821,297 | B2 | 11/2004 | Snyders |
| 6,837,247 | B2 | 1/2005 | Buckberg et al. |
| 6,840,246 | B2 | 1/2005 | Downing |
| 6,846,324 | B2 | 1/2005 | Stobie |
| 6,869,444 | B2 | 3/2005 | Gabbay |
| 6,908,478 | B2 | 6/2005 | Alferness et al. |
| 6,911,043 | B2 | 6/2005 | Myers et al. |

(56) References Cited

U.S. PATENT DOCUMENTS 6,926,730 B1 8/2005 Nguyen et al.
6,966,925 B2 11/2005 Stobie
6,991,649 B2 1/2006 Sievers
6,997,950 B2 2/2006 Chawla
7,018,408 B2 3/2006 Bailey et al.
7,037,333 B2 5/2006 Myers et al.
7,048,754 B2 5/2006 Martin et al.
7,056,280 B2 6/2006 Buckberg et al.
7,070,618 B2 7/2006 Streeter
7,077,861 B2 7/2006 Spence
7,077,862 B2 7/2006 Vidlund et al.
7,083,628 B2 8/2006 Bachman
7,087,064 B1 8/2006 Hyde
7,112,207 B2 9/2006 Allen et al.
7,122,043 B2 10/2006 Greenhalgh et al.
7,160,322 B2 1/2007 Gabbay
7,166,126 B2 1/2007 Spence et al.
7,175,656 B2 2/2007 Khairkhahan
7,195,641 B2 3/2007 Palmaz et al.
7,217,284 B2 5/2007 Houser et al.
7,226,467 B2 6/2007 Lucatero et al.
7,275,546 B2 10/2007 Buckberg et al.
7,291,168 B2 11/2007 Macoviak et al.
7,294,148 B2 11/2007 McCarthy
7,296,577 B2 11/2007 Taylor et al.
7,316,706 B2 1/2008 Bloom et al.
7,320,704 B2 1/2008 Lashinski et al.
7,335,213 B1 2/2008 Hyde et al.
7,338,520 B2 3/2008 Bailey et al.
7,341,584 B1 3/2008 Starkey
7,357,814 B2 4/2008 Gabbay
7,374,572 B2 5/2008 Gabbay
RE40,377 E 6/2008 Williamson, IV et al.
7,381,220 B2 6/2008 Macoviak et al.
7,396,364 B2 7/2008 Moaddeb et al.
7,404,824 B1 7/2008 Webler et al.
7,435,257 B2 10/2008 Lashinski et al.
7,445,630 B2 11/2008 Lashinski et al.
7,455,689 B2 11/2008 Johnson
7,485,143 B2 2/2009 Webler et al.
7,510,573 B2 3/2009 Gabbay
7,510,576 B2 3/2009 Langberg et al.
7,527,646 B2 5/2009 Rahdert et al.
7,527,647 B2 5/2009 Spence
7,530,998 B1 5/2009 Starkey
7,534,259 B2 5/2009 Lashinski et al.
7,556,645 B2 7/2009 Lashinski et al.
7,559,936 B2 7/2009 Levine
7,563,267 B2 7/2009 Goldfarb et al.
7,563,273 B2 7/2009 Goldfarb et al.
7,591,847 B2 9/2009 Navia et al.
7,608,091 B2 10/2009 Goldfarb et al.
7,611,534 B2 11/2009 Kapadia et al.
7,621,948 B2 11/2009 Herrmann et al.
7,648,532 B2 1/2010 Greenhalgh et al.
7,655,015 B2 2/2010 Goldfarb et al.
7,658,762 B2 2/2010 Lashinski et al.
7,658,763 B2 2/2010 Stobie
7,666,224 B2 2/2010 Vidlund et al.
7,674,286 B2 3/2010 Alfieri et al.
7,678,145 B2 3/2010 Vidlund et al.
7,682,391 B2 3/2010 Johnson
7,691,144 B2 4/2010 Chang et al.
7,699,892 B2 4/2010 Rafiee et al.
7,704,269 B2 4/2010 St. Goar et al.
7,704,277 B2 4/2010 Zakay et al.
7,736,388 B2 6/2010 Goldfarb et al.
7,740,638 B2 6/2010 Hyde
7,744,609 B2 6/2010 Allen et al.
7,753,923 B2 7/2010 St. Goar et al.
7,758,491 B2 7/2010 Buckner et al.
7,758,595 B2 7/2010 Allen et al.
7,776,084 B2 8/2010 Johnson
7,785,366 B2 8/2010 Maurer et al.
7,799,038 B2 9/2010 Sogard et al.
7,803,187 B2 9/2010 Hauser
7,819,915 B2 10/2010 Stobie et al.
7,846,203 B2 12/2010 Cribier
7,887,552 B2 2/2011 Bachman
7,901,454 B2 3/2011 Kapadia et al.
7,909,866 B2 3/2011 Stobie
7,914,576 B2 3/2011 Navia et al.
7,927,370 B2 4/2011 Webler et al.
7,935,144 B2 5/2011 Robin et al.
7,935,145 B2 5/2011 Alfieri et al.
7,938,827 B2 5/2011 Hauck et al.
7,942,928 B2 5/2011 Webler et al.
7,951,195 B2 5/2011 Antonsson et al.
7,951,196 B2 5/2011 McCarthy
7,955,385 B2 6/2011 Crittenden
7,959,673 B2 6/2011 Carpentier et al.
7,981,139 B2 7/2011 Martin et al.
7,988,725 B2 8/2011 Gross et al.
7,993,396 B2 8/2011 McCarthy
7,998,151 B2 8/2011 St. Goar et al.
8,012,201 B2 9/2011 Lashinski et al.
8,012,202 B2 9/2011 Alameddine
8,016,882 B2 9/2011 Macoviak et al.
8,029,518 B2 10/2011 Goldfarb et al.
8,052,751 B2 11/2011 Aklog et al.
8,057,493 B2 11/2011 Goldfarb et al.
8,062,355 B2 11/2011 Figulla et al.
8,070,804 B2 12/2011 Hyde et al.
8,070,805 B2 12/2011 Vidlund et al.
8,092,525 B2 1/2012 Eliasen et al.
8,118,866 B2 2/2012 Herrmann et al.
8,128,691 B2 3/2012 Keranen
8,133,272 B2 3/2012 Hyde
8,142,494 B2 3/2012 Rahdert et al.
8,142,495 B2 3/2012 Hasenkam et al.
8,147,542 B2 4/2012 Maisano et al.
8,152,844 B2 4/2012 Rao et al.
8,163,013 B2 4/2012 Machold et al.
8,187,207 B2 5/2012 Machold et al.
8,187,299 B2 5/2012 Goldfarb et al.
8,187,323 B2 5/2012 Mortier et al.
8,204,605 B2 6/2012 Hastings et al.
8,206,439 B2 6/2012 Gomez Duran
8,216,230 B2 7/2012 Hauck et al.
8,216,256 B2 7/2012 Raschdorf, Jr. et al.
8,216,302 B2 7/2012 Wilson et al.
8,216,303 B2 7/2012 Navia
8,221,493 B2 7/2012 Boyle et al.
8,226,711 B2 7/2012 Mortier et al.
8,241,304 B2 8/2012 Bachman
8,241,351 B2 8/2012 Cabiri
8,252,050 B2 8/2012 Maisano
8,252,051 B2 8/2012 Chau et al.
8,262,725 B2 9/2012 Subramanian
8,277,502 B2 10/2012 Miller et al.
8,287,591 B2 10/2012 Keidar et al.
8,292,884 B2 10/2012 Levine et al.
8,308,796 B2 11/2012 Lashinski et al.
8,323,336 B2 12/2012 Hill et al.
8,337,390 B2 12/2012 Ferrazzi
8,353,956 B2 1/2013 Miller et al.
8,361,086 B2 1/2013 Allen et al.
8,377,118 B2 2/2013 Lashinski et al.
8,382,796 B2 2/2013 Blaeser et al.
8,382,828 B2 2/2013 Roberts
8,382,829 B1 2/2013 Call et al.
RE44,075 E 3/2013 Williamson, IV et al.
8,398,708 B2 3/2013 Meiri et al.
8,408,214 B2 4/2013 Spenser
8,413,573 B2 4/2013 Rebecchi
8,414,644 B2 4/2013 Quadri et al.
8,449,606 B2 5/2013 Eliasen et al.
8,454,683 B2 6/2013 Rafiee et al.
8,470,028 B2 6/2013 Thornton et al.
8,500,800 B2 8/2013 Maisano et al.
8,506,624 B2 8/2013 Vidlund et al.
8,523,881 B2 9/2013 Cabiri et al.
8,545,553 B2 10/2013 Zipory et al.
8,608,797 B2 12/2013 Gross et al.

(56) References Cited

U.S. PATENT DOCUMENTS

| | | | |
|---|---|---|---|
| 8,657,872 | B2 | 2/2014 | Seguin |
| 8,690,939 | B2 | 4/2014 | Miller et al. |
| 8,715,342 | B2 | 5/2014 | Zipory et al. |
| 8,734,467 | B2 | 5/2014 | Miller et al. |
| 8,784,483 | B2 | 7/2014 | Navia |
| 8,790,394 | B2 | 7/2014 | Miller et al. |
| 8,795,352 | B2 | 8/2014 | O'beirne et al. |
| 8,808,368 | B2 | 8/2014 | Maisano et al. |
| 8,845,717 | B2 | 9/2014 | Khairkhahan et al. |
| 8,858,623 | B2 | 10/2014 | Miller et al. |
| 8,888,843 | B2 | 11/2014 | Khairkhahan et al. |
| 8,888,844 | B2 | 11/2014 | Eliasen et al. |
| 8,911,494 | B2 | 12/2014 | Hammer et al. |
| 8,926,695 | B2 | 1/2015 | Gross et al. |
| 8,926,696 | B2 | 1/2015 | Cabiri et al. |
| 8,926,697 | B2 | 1/2015 | Gross et al. |
| 8,940,042 | B2 | 1/2015 | Miller et al. |
| 8,940,044 | B2 | 1/2015 | Hammer et al. |
| 8,968,395 | B2 | 3/2015 | Hauser et al. |
| 9,005,279 | B2 | 4/2015 | Gabbay |
| 9,011,520 | B2 | 4/2015 | Miller et al. |
| 9,011,530 | B2 | 4/2015 | Reich et al. |
| 9,050,189 | B2 | 6/2015 | Padala et al. |
| 9,056,006 | B2 | 6/2015 | Edelman et al. |
| 9,119,719 | B2 | 9/2015 | Zipory et al. |
| 9,180,007 | B2 | 11/2015 | Reich et al. |
| 9,192,472 | B2 | 11/2015 | Gross et al. |
| 9,204,964 | B2 | 12/2015 | Dahlgren et al. |
| 9,232,996 | B2 | 1/2016 | Sun et al. |
| 9,232,999 | B2 | 1/2016 | Maurer et al. |
| 9,265,608 | B2 | 2/2016 | Miller et al. |
| 9,277,994 | B2 | 3/2016 | Miller et al. |
| 9,295,553 | B2 | 3/2016 | Padala et al. |
| 9,351,830 | B2 | 5/2016 | Gross et al. |
| 9,414,921 | B2 | 8/2016 | Miller et al. |
| 9,452,048 | B2 | 9/2016 | O'beirne et al. |
| 9,474,606 | B2 | 10/2016 | Zipory et al. |
| 9,526,613 | B2 | 12/2016 | Gross et al. |
| 9,549,817 | B2 | 1/2017 | Rafiee |
| 9,554,906 | B2 | 1/2017 | Aklog et al. |
| 9,561,104 | B2 | 2/2017 | Miller et al. |
| 9,592,118 | B2 | 3/2017 | Khairkhahan et al. |
| 9,592,121 | B1 | 3/2017 | Khairkhahan |
| 9,592,122 | B2 | 3/2017 | Zipory et al. |
| 9,610,161 | B2 | 4/2017 | Macoviak et al. |
| 9,610,162 | B2 | 4/2017 | Zipory et al. |
| 9,610,163 | B2 | 4/2017 | Khairkhahan et al. |
| 9,622,861 | B2 | 4/2017 | Miller et al. |
| 9,636,224 | B2 | 5/2017 | Zipory et al. |
| 9,662,209 | B2 | 5/2017 | Gross et al. |
| 9,713,530 | B2 | 7/2017 | Cabiri et al. |
| 9,724,192 | B2 | 8/2017 | Sheps et al. |
| 9,730,793 | B2 | 8/2017 | Reich et al. |
| 9,775,709 | B2 | 10/2017 | Miller et al. |
| 9,814,572 | B2 | 11/2017 | Edelman et al. |
| 9,872,769 | B2 | 1/2018 | Gross et al. |
| 9,883,943 | B2 | 2/2018 | Gross et al. |
| 9,918,840 | B2 | 3/2018 | Reich et al. |
| 9,937,042 | B2 | 4/2018 | Cabiri et al. |
| 9,949,828 | B2 | 4/2018 | Sheps et al. |
| 9,968,452 | B2 | 5/2018 | Sheps et al. |
| 9,968,454 | B2 | 5/2018 | Reich et al. |
| 9,974,653 | B2 | 5/2018 | Gross et al. |
| 10,028,832 | B2 | 7/2018 | Quill et al. |
| 10,098,737 | B2 | 10/2018 | Miller |
| 10,123,874 | B2 | 11/2018 | Khairkhahan et al. |
| 10,130,472 | B2 | 11/2018 | O'beirne et al. |
| 10,149,672 | B2 | 12/2018 | Halkos et al. |
| 10,166,098 | B2 | 1/2019 | Khairkhahan et al. |
| 10,195,030 | B2 | 2/2019 | Gross et al. |
| 10,226,342 | B2 | 3/2019 | Kutzik et al. |
| 10,251,635 | B2 | 4/2019 | Khairkhahan et al. |
| 10,265,170 | B2 | 4/2019 | Zipory et al. |
| 10,299,793 | B2 | 5/2019 | Zipory et al. |
| 10,350,068 | B2 | 7/2019 | Miller et al. |
| 10,357,366 | B2 | 7/2019 | Gross et al. |
| 10,363,136 | B2 | 7/2019 | Miller et al. |
| 10,363,137 | B2 | 7/2019 | Gross et al. |
| 10,368,982 | B2 | 8/2019 | Weber et al. |
| 10,376,266 | B2 | 8/2019 | Herman et al. |
| 10,376,365 | B2 | 8/2019 | Khairkhahan et al. |
| 10,383,726 | B2 | 8/2019 | Kramer |
| 10,426,619 | B2 | 10/2019 | Mohl |
| 10,433,955 | B2 | 10/2019 | Edelman et al. |
| 10,449,046 | B2 | 10/2019 | Rafiee |
| 10,449,049 | B2 | 10/2019 | Li et al. |
| 10,449,333 | B2 | 10/2019 | Hammer et al. |
| 10,470,882 | B2 | 11/2019 | Gross et al. |
| 10,470,883 | B2 | 11/2019 | Khairkhahan et al. |
| 10,478,303 | B2 | 11/2019 | Khairkhahan et al. |
| 10,492,909 | B2 | 12/2019 | Miller et al. |
| 10,500,048 | B2 | 12/2019 | Khairkhahan et al. |
| 10,512,542 | B2 | 12/2019 | Khairkhahan et al. |
| 10,517,719 | B2 | 12/2019 | Miller et al. |
| 10,543,088 | B2 | 1/2020 | Lashinski |
| 10,548,729 | B2 | 2/2020 | Zipory et al. |
| 10,548,731 | B2 | 2/2020 | Lashinski et al. |
| 10,561,498 | B2 | 2/2020 | Gross et al. |
| 10,568,738 | B2 | 2/2020 | Sheps et al. |
| 10,583,009 | B2 | 3/2020 | Hauser et al. |
| 10,610,360 | B2 | 4/2020 | Reich et al. |
| 10,653,524 | B2 | 5/2020 | Khairkhahan et al. |
| 10,702,386 | B2 | 7/2020 | Khairkhahan et al. |
| 10,751,180 | B2 | 8/2020 | Schewel |
| 11,000,372 | B2 | 5/2021 | Khairkhahan et al. |
| 11,007,057 | B2 | 5/2021 | Pham et al. |
| 11,026,791 | B2 | 6/2021 | Genovese et al. |
| 11,076,957 | B2 | 8/2021 | Mohl |
| 11,160,656 | B2 | 11/2021 | Khairkhahan |
| 11,266,502 | B1 | 3/2022 | Wallace et al. |
| 11,298,229 | B2 | 4/2022 | Khairkhahan |
| 11,413,145 | B2 | 8/2022 | Khairkhahan |
| 11,419,719 | B2 | 8/2022 | Schewel et al. |
| 11,419,722 | B2 | 8/2022 | Khairkhahan et al. |
| 11,426,279 | B2 | 8/2022 | Khairkhahan et al. |
| 11,432,928 | B2 | 9/2022 | Mohl |
| 11,464,634 | B2 | 10/2022 | Khairkhahan et al. |
| 11,497,606 | B2 | 11/2022 | Khairkhahan et al. |
| 11,504,237 | B2 | 11/2022 | Gifford et al. |
| 11,534,302 | B2 | 12/2022 | Khairkhahan et al. |
| 11,571,305 | B2 | 2/2023 | Padala et al. |
| 11,622,759 | B2 | 4/2023 | Khairkhahan et al. |
| 11,633,281 | B2 | 4/2023 | Kappetein et al. |
| 11,648,119 | B2 | 5/2023 | Khairkhahan et al. |
| 11,648,120 | B2 | 5/2023 | Khairkhahan et al. |
| 11,672,659 | B2 | 6/2023 | Khairkhahan et al. |
| 11,672,660 | B2 | 6/2023 | Moh et al. |
| 11,678,986 | B2 | 6/2023 | Khairkhahan et al. |
| 11,701,228 | B2 | 7/2023 | Genovese et al. |
| 11,759,321 | B2 | 9/2023 | Khairkhahan et al. |
| 11,883,291 | B2 | 1/2024 | Gifford et al. |
| 11,974,921 | B2 | 5/2024 | Khairkhahan et al. |
| 12,053,373 | B2 | 8/2024 | McLean et al. |
| 12,109,116 | B2 | 10/2024 | Khairkhahan et al. |
| 12,150,856 | B2 | 11/2024 | Khairkhahan et al. |
| 12,251,308 | B2 | 3/2025 | McLean et al. |
| 12,285,336 | B2 | 4/2025 | Khairkhahan |
| 12,290,439 | B2 | 5/2025 | Padala et al. |
| 12,295,845 | B2 | 5/2025 | Khairkhahan et al. |
| 12,350,153 | B2 | 7/2025 | Khairkhahan et al. |
| 12,364,601 | B2 | 7/2025 | Zimmerman et al. |
| 12,370,048 | B2 | 7/2025 | Padala et al. |
| 12,390,331 | B2 | 8/2025 | Kappetein et al. |
| 12,396,855 | B1 | 8/2025 | Padala |
| 12,414,855 | B2 | 9/2025 | Miyashiro et al. |
| 12,419,747 | B2 | 9/2025 | Khairkhahan et al. |
| 12,433,749 | B2 | 10/2025 | Padala |
| 12,447,018 | B2 | 10/2025 | Pham et al. |
| 12,458,341 | B2 | 11/2025 | Khairkhahan et al. |
| 12,465,489 | B2 | 11/2025 | Khairkhahan |
| 12,478,474 | B2 | 11/2025 | Khairkhahan et al. |
| 12,599,482 | B2 | 4/2026 | Khairkhahan et al. |
| 12,616,574 | B2 | 5/2026 | Khairkhahan |
| 2001/0007956 | A1 | 7/2001 | Letac et al. |

(56) References Cited

U.S. PATENT DOCUMENTS

| | | | | |
|---|---|---|---|---|
| 2001/0021872 | A1 | 9/2001 | Bailey et al. | |
| 2002/0029080 | A1 | 3/2002 | Mortier et al. | |
| 2002/0058995 | A1 | 5/2002 | Stevens | |
| 2002/0116024 | A1 | 8/2002 | Goldberg et al. | |
| 2002/0138135 | A1 | 9/2002 | Duerig | |
| 2002/0188301 | A1 | 12/2002 | Dallara et al. | |
| 2003/0023248 | A1 | 1/2003 | Parodi | |
| 2003/0100943 | A1 | 5/2003 | Bolduc | |
| 2003/0105474 | A1 | 6/2003 | Bonutti | |
| 2003/0135263 | A1 | 7/2003 | Rourke et al. | |
| 2003/0191497 | A1 | 10/2003 | Cope | |
| 2003/0199975 | A1 | 10/2003 | Gabbay | |
| 2004/0082956 | A1 | 4/2004 | Baldwin et al. | |
| 2004/0088047 | A1 | 5/2004 | Spence et al. | |
| 2004/0143323 | A1 | 7/2004 | Chawla | |
| 2004/0172046 | A1 | 9/2004 | Hlavka et al. | |
| 2004/0193217 | A1 | 9/2004 | Lubbers et al. | |
| 2004/0210307 | A1 | 10/2004 | Khairkhahan | |
| 2005/0004665 | A1 | 1/2005 | Aklog | |
| 2005/0004668 | A1 | 1/2005 | Aklog et al. | |
| 2005/0010287 | A1 | 1/2005 | Macoviak et al. | |
| 2005/0075727 | A1 | 4/2005 | Wheatley et al. | |
| 2005/0096740 | A1 | 5/2005 | Langberg et al. | |
| 2005/0107871 | A1 | 5/2005 | Realyvasquez | |
| 2005/0159810 | A1 | 7/2005 | Filsoufi | |
| 2005/0177180 | A1 | 8/2005 | Kaganov et al. | |
| 2005/0228495 | A1 | 10/2005 | Macoviak | |
| 2005/0251162 | A1 | 11/2005 | Rothe et al. | |
| 2005/0261708 | A1 | 11/2005 | Pasricha et al. | |
| 2005/0267573 | A9 | 12/2005 | Macoviak et al. | |
| 2005/0283232 | A1 | 12/2005 | Gabbay | |
| 2006/0030885 | A1 | 2/2006 | Hyde | |
| 2006/0058871 | A1 | 3/2006 | Zakay et al. | |
| 2006/0122608 | A1 | 6/2006 | Fallin et al. | |
| 2006/0149368 | A1 | 7/2006 | Spence | |
| 2006/0190030 | A1 | 8/2006 | To et al. | |
| 2006/0252984 | A1 | 11/2006 | Rahdert et al. | |
| 2007/0005069 | A1 | 1/2007 | Contiliano et al. | |
| 2007/0049942 | A1 | 3/2007 | Hindrichs et al. | |
| 2007/0049970 | A1 | 3/2007 | Belef et al. | |
| 2007/0093890 | A1 | 4/2007 | Eliasen et al. | |
| 2007/0112352 | A1 | 5/2007 | Sorensen et al. | |
| 2007/0112425 | A1 | 5/2007 | Schaller et al. | |
| 2007/0118151 | A1 | 5/2007 | Davidson | |
| 2007/0129758 | A1 | 6/2007 | Saadat | |
| 2007/0149947 | A1 * | 6/2007 | Byrum .............. | A61M 39/0208<br>604/288.04 |
| 2007/0185571 | A1 | 8/2007 | Kapadia et al. | |
| 2007/0233239 | A1 | 10/2007 | Navia et al. | |
| 2007/0239272 | A1 | 10/2007 | Navia et al. | |
| 2007/0244554 | A1 | 10/2007 | Rafiee et al. | |
| 2007/0244555 | A1 | 10/2007 | Rafiee et al. | |
| 2007/0244556 | A1 | 10/2007 | Rafiee et al. | |
| 2007/0250160 | A1 | 10/2007 | Rafiee | |
| 2007/0255399 | A1 | 11/2007 | Eliasen et al. | |
| 2007/0265658 | A1 | 11/2007 | Nelson et al. | |
| 2007/0265700 | A1 | 11/2007 | Eliasen et al. | |
| 2007/0265702 | A1 | 11/2007 | Lattouf | |
| 2007/0282375 | A1 | 12/2007 | Hindrichs et al. | |
| 2007/0293943 | A1 | 12/2007 | Quinn | |
| 2008/0065204 | A1 | 3/2008 | Macoviak et al. | |
| 2008/0109075 | A1 | 5/2008 | Keranen | |
| 2008/0125860 | A1 | 5/2008 | Webler et al. | |
| 2008/0125861 | A1 | 5/2008 | Webler et al. | |
| 2008/0195205 | A1 | 8/2008 | Schwartz | |
| 2008/0262609 | A1 | 10/2008 | Gross et al. | |
| 2008/0319541 | A1 | 12/2008 | Filsoufi | |
| 2009/0012354 | A1 | 1/2009 | Wood | |
| 2009/0088836 | A1 | 4/2009 | Bishop et al. | |
| 2009/0177277 | A1 | 7/2009 | Milo | |
| 2009/0234404 | A1 | 9/2009 | Fitzgerald et al. | |
| 2009/0259304 | A1 | 10/2009 | OBeirne et al. | |
| 2009/0259307 | A1 | 10/2009 | Gross et al. | |
| 2009/0287304 | A1 | 11/2009 | Dahlgren et al. | |
| 2009/0326648 | A1 | 12/2009 | Machold et al. | |
| 2010/0010538 | A1 | 1/2010 | Juravic et al. | |
| 2010/0069954 | A1 | 3/2010 | Blaeser et al. | |
| 2010/0121435 | A1 | 5/2010 | Subramanian et al. | |
| 2010/0121437 | A1 | 5/2010 | Subramanian et al. | |
| 2010/0131057 | A1 | 5/2010 | Subramanian et al. | |
| 2010/0161043 | A1 | 6/2010 | Maisano et al. | |
| 2010/0161047 | A1 | 6/2010 | Cabiri et al. | |
| 2010/0249920 | A1 | 9/2010 | Bolling et al. | |
| 2010/0249947 | A1 | 9/2010 | Lesh et al. | |
| 2010/0262233 | A1 | 10/2010 | He | |
| 2010/0280603 | A1 | 11/2010 | Maisano et al. | |
| 2010/0280604 | A1 | 11/2010 | Zipory et al. | |
| 2010/0280605 | A1 | 11/2010 | Hammer | |
| 2010/0280606 | A1 | 11/2010 | Naor | |
| 2010/0286767 | A1 | 11/2010 | Zipory et al. | |
| 2010/0298929 | A1 | 11/2010 | Thornton et al. | |
| 2010/0312333 | A1 | 12/2010 | Navia et al. | |
| 2011/0004299 | A1 | 1/2011 | Navia et al. | |
| 2011/0082538 | A1 | 4/2011 | Dahlgren et al. | |
| 2011/0106245 | A1 | 5/2011 | Miller et al. | |
| 2011/0106247 | A1 | 5/2011 | Miller et al. | |
| 2011/0137397 | A1 | 6/2011 | Chau et al. | |
| 2011/0166649 | A1 | 7/2011 | Gross et al. | |
| 2011/0184510 | A1 | 7/2011 | Maisano et al. | |
| 2011/0224785 | A1 | 9/2011 | Hacohen | |
| 2011/0238088 | A1 | 9/2011 | Bolduc et al. | |
| 2011/0282361 | A1 | 11/2011 | Miller | |
| 2011/0288635 | A1 | 11/2011 | Miller et al. | |
| 2011/0301698 | A1 | 12/2011 | Miller et al. | |
| 2011/0301701 | A1 | 12/2011 | Padala et al. | |
| 2011/0319989 | A1 | 12/2011 | Lane et al. | |
| 2011/0319990 | A1 | 12/2011 | Macoviak et al. | |
| 2012/0016468 | A1 | 1/2012 | Robin et al. | |
| 2012/0022557 | A1 | 1/2012 | Cabiri et al. | |
| 2012/0022644 | A1 | 1/2012 | Reich et al. | |
| 2012/0078360 | A1 | 3/2012 | Rafiee | |
| 2012/0136436 | A1 | 5/2012 | Cabiri et al. | |
| 2012/0165930 | A1 | 6/2012 | Gifford et al. | |
| 2012/0197388 | A1 | 8/2012 | Khairkhahan et al. | |
| 2012/0203336 | A1 | 8/2012 | Annest | |
| 2012/0245604 | A1 | 9/2012 | Tegzes | |
| 2012/0283757 | A1 | 11/2012 | Miller et al. | |
| 2012/0323316 | A1 | 12/2012 | Chau et al. | |
| 2012/0330410 | A1 | 12/2012 | Hammer et al. | |
| 2012/0330411 | A1 | 12/2012 | Gross et al. | |
| 2013/0023985 | A1 | 1/2013 | Khairkhahan et al. | |
| 2013/0030523 | A1 | 1/2013 | Padala et al. | |
| 2013/0096672 | A1 | 4/2013 | Reich et al. | |
| 2013/0116776 | A1 | 5/2013 | Gross et al. | |
| 2013/0116780 | A1 | 5/2013 | Miller et al. | |
| 2013/0131792 | A1 | 5/2013 | Miller et al. | |
| 2013/0190861 | A1 | 7/2013 | Chau et al. | |
| 2013/0190866 | A1 | 7/2013 | Zipory et al. | |
| 2013/0238024 | A1 | 9/2013 | Taylor et al. | |
| 2013/0282028 | A1 | 10/2013 | Conklin et al. | |
| 2013/0325110 | A1 | 12/2013 | Khalil et al. | |
| 2013/0338763 | A1 | 12/2013 | Rowe et al. | |
| 2014/0018906 | A1 | 1/2014 | Rafiee | |
| 2014/0025163 | A1 | 1/2014 | Padala et al. | |
| 2014/0039615 | A1 | 2/2014 | Padala et al. | |
| 2014/0067048 | A1 | 3/2014 | Chau | |
| 2014/0067054 | A1 | 3/2014 | Chau et al. | |
| 2014/0094903 | A1 | 4/2014 | Miller et al. | |
| 2014/0128965 | A1 | 5/2014 | Rafiee | |
| 2014/0142695 | A1 | 5/2014 | Gross et al. | |
| 2014/0148898 | A1 | 5/2014 | Gross et al. | |
| 2014/0155995 | A1 | 6/2014 | Sun et al. | |
| 2014/0222137 | A1 | 8/2014 | Miller et al. | |
| 2014/0243963 | A1 | 8/2014 | Sheps et al. | |
| 2014/0276648 | A1 | 9/2014 | Hammer et al. | |
| 2014/0277088 | A1 | 9/2014 | Friedman | |
| 2014/0309661 | A1 | 10/2014 | Sheps et al. | |
| 2014/0343668 | A1 | 11/2014 | Zipory et al. | |
| 2014/0358223 | A1 | 12/2014 | Rafiee et al. | |
| 2014/0379075 | A1 | 12/2014 | Maurer et al. | |
| 2015/0012087 | A1 | 1/2015 | Miller et al. | |
| 2015/0039083 | A1 | 2/2015 | Rafiee et al. | |
| 2015/0057682 | A1 | 2/2015 | Kovach | |
| 2015/0081014 | A1 | 3/2015 | Gross et al. | |

(56) References Cited

U.S. PATENT DOCUMENTS

| | | | |
|---|---|---|---|
| 2015/0100116 | A1 | 4/2015 | Mohl et al. |
| 2015/0105855 | A1 | 4/2015 | Cabiri et al. |
| 2015/0112429 | A1 | 4/2015 | Khairkhahan et al. |
| 2015/0112432 | A1 | 4/2015 | Reich et al. |
| 2015/0119981 | A1 | 4/2015 | Khairkhahan et al. |
| 2015/0164637 | A1 | 6/2015 | Khairkhahan et al. |
| 2015/0182336 | A1 | 7/2015 | Zipory et al. |
| 2015/0202043 | A1 | 7/2015 | Zakai et al. |
| 2015/0230924 | A1 | 8/2015 | Miller et al. |
| 2015/0257877 | A1 | 9/2015 | Hernandez |
| 2015/0272586 | A1 | 10/2015 | Herman et al. |
| 2015/0272734 | A1 | 10/2015 | Sheps et al. |
| 2015/0297212 | A1 | 10/2015 | Reich et al. |
| 2015/0366556 | A1 | 12/2015 | Khairkhahan et al. |
| 2015/0366666 | A1 | 12/2015 | Khairkhahan et al. |
| 2016/0008132 | A1 | 1/2016 | Cabiri et al. |
| 2016/0030176 | A1 | 2/2016 | Mohl et al. |
| 2016/0058557 | A1 | 3/2016 | Reich et al. |
| 2016/0074164 | A1 | 3/2016 | Naor |
| 2016/0089233 | A1 | 3/2016 | Lee et al. |
| 2016/0106437 | A1 | 4/2016 | van der Burg et al. |
| 2016/0113767 | A1 | 4/2016 | Miller et al. |
| 2016/0157862 | A1 | 6/2016 | Hernandez et al. |
| 2016/0158008 | A1 | 6/2016 | Miller et al. |
| 2016/0262755 | A1 | 9/2016 | Zipory et al. |
| 2016/0324639 | A1 | 11/2016 | Nguyen et al. |
| 2016/0331523 | A1 | 11/2016 | Chau et al. |
| 2016/0361168 | A1 | 12/2016 | Gross et al. |
| 2016/0361169 | A1 | 12/2016 | Gross et al. |
| 2017/0000508 | A1 | 1/2017 | Halkos et al. |
| 2017/0000609 | A1 | 1/2017 | Gross et al. |
| 2017/0086975 | A1 | 3/2017 | Gilmore et al. |
| 2017/0100249 | A1 | 4/2017 | Miller et al. |
| 2017/0105839 | A1 | 4/2017 | Subramanian et al. |
| 2017/0112618 | A1 | 4/2017 | Li et al. |
| 2017/0135815 | A1 | 5/2017 | Gross et al. |
| 2017/0135816 | A1 | 5/2017 | Lashinski et al. |
| 2017/0189186 | A1 | 7/2017 | Mohl |
| 2017/0196691 | A1 | 7/2017 | Zipory et al. |
| 2017/0209270 | A1 | 7/2017 | Miller et al. |
| 2017/0245993 | A1 | 8/2017 | Gross et al. |
| 2017/0245994 | A1 | 8/2017 | Khairkhahan et al. |
| 2017/0258588 | A1 | 9/2017 | Zipory et al. |
| 2017/0258589 | A1 | 9/2017 | Pham et al. |
| 2017/0258590 | A1 | 9/2017 | Khairkhahan et al. |
| 2017/0265995 | A1 | 9/2017 | Khairkhahan et al. |
| 2017/0296340 | A1 | 10/2017 | Gross et al. |
| 2017/0325958 | A1 | 11/2017 | Reich et al. |
| 2017/0325959 | A1 | 11/2017 | Sheps et al. |
| 2017/0354500 | A1 | 12/2017 | Martinez et al. |
| 2017/0367825 | A1 | 12/2017 | Cabiri et al. |
| 2018/0008409 | A1 | 1/2018 | Kutzik et al. |
| 2018/0014933 | A1 | 1/2018 | Miller et al. |
| 2018/0014934 | A1 | 1/2018 | Miller et al. |
| 2018/0049875 | A1 | 2/2018 | Iflah et al. |
| 2018/0116797 | A9 | 5/2018 | Miller et al. |
| 2018/0125657 | A1 | 5/2018 | Dahlgren et al. |
| 2018/0228608 | A1 | 8/2018 | Sheps et al. |
| 2018/0250133 | A1 | 9/2018 | Reich et al. |
| 2018/0256318 | A1 | 9/2018 | Khairkhahan |
| 2018/0256333 | A1 | 9/2018 | Cabiri et al. |
| 2018/0256334 | A1 | 9/2018 | Sheps et al. |
| 2018/0256865 | A1 | 9/2018 | Finch et al. |
| 2018/0263776 | A1 | 9/2018 | Gross et al. |
| 2018/0263777 | A1 | 9/2018 | Gross et al. |
| 2018/0318080 | A1 | 11/2018 | Quill et al. |
| 2018/0325670 | A1 | 11/2018 | De Canniere |
| 2019/0008641 | A1 | 1/2019 | Dahlgren et al. |
| 2019/0046318 | A1 | 2/2019 | Miller et al. |
| 2019/0070004 | A1 | 3/2019 | Ifah et al. |
| 2019/0076247 | A1 | 3/2019 | Zeng |
| 2019/0076249 | A1 | 3/2019 | Khairkhahan |
| 2019/0125325 | A1 | 5/2019 | Sheps et al. |
| 2019/0133586 | A1 | 5/2019 | Zipory et al. |
| 2019/0151090 | A1 | 5/2019 | Gross et al. |
| 2019/0151093 | A1 | 5/2019 | Keidar et al. |
| 2019/0159898 | A1 | 5/2019 | Kutzik et al. |
| 2019/0167425 | A1 | 6/2019 | Reich et al. |
| 2019/0175344 | A1 | 6/2019 | Khairkhahan |
| 2019/0183644 | A1 | 6/2019 | Hacohen |
| 2019/0201191 | A1 | 7/2019 | McLean et al. |
| 2019/0216600 | A1 | 7/2019 | Zipory et al. |
| 2019/0254821 | A1 | 8/2019 | Rafiee et al. |
| 2019/0269512 | A9 | 9/2019 | Lashinski |
| 2019/0269513 | A9 | 9/2019 | Cabiri et al. |
| 2019/0274830 | A1 | 9/2019 | Miller et al. |
| 2019/0282358 | A1 | 9/2019 | Khairkhahan et al. |
| 2019/0282364 | A1 | 9/2019 | Khairkhahan et al. |
| 2019/0290431 | A1 | 9/2019 | Genovese et al. |
| 2019/0298332 | A1 | 10/2019 | Khairkhahan et al. |
| 2019/0298522 | A1 | 10/2019 | Subramanian et al. |
| 2019/0321049 | A1 | 10/2019 | Herman et al. |
| 2019/0336288 | A1 | 11/2019 | Gross et al. |
| 2019/0336289 | A1 | 11/2019 | Miller et al. |
| 2019/0350703 | A1 | 11/2019 | Weber et al. |
| 2019/0350705 | A1 | 11/2019 | Schewel et al. |
| 2019/0374343 | A1 | 12/2019 | Lashinski et al. |
| 2019/0374750 | A1 | 12/2019 | Hammer et al. |
| 2019/0380834 | A1 | 12/2019 | Rafiee |
| 2020/0015971 | A1 | 1/2020 | Brauon et al. |
| 2020/0030097 | A1 | 1/2020 | Khairkhahan et al. |
| 2020/0038186 | A1 | 2/2020 | Gross et al. |
| 2020/0100899 | A1 | 4/2020 | Miller et al. |
| 2020/0113685 | A1 | 4/2020 | Miller et al. |
| 2020/0205966 | A1 | 7/2020 | Khairkhahan et al. |
| 2020/0205975 | A1 | 7/2020 | Khairkhahan |
| 2020/0205978 | A1 | 7/2020 | Padala et al. |
| 2020/0205980 | A1 | 7/2020 | Khairkhahan et al. |
| 2020/0214841 | A1 | 7/2020 | Khairkhahan et al. |
| 2020/0222185 | A1 | 7/2020 | Kappetein et al. |
| 2020/0229918 | A1 | 7/2020 | Pham et al. |
| 2020/0268512 | A1 | 8/2020 | Mohl |
| 2020/0275974 | A1 | 9/2020 | Gifford et al. |
| 2020/0289265 | A1 | 9/2020 | Gifford et al. |
| 2020/0330229 | A1 | 10/2020 | Serraf et al. |
| 2020/0337843 | A1 | 10/2020 | Khairkhahan et al. |
| 2020/0383776 | A1 | 12/2020 | Schewel |
| 2020/0397567 | A1 | 12/2020 | Khairkhahan et al. |
| 2021/0085462 | A1 | 3/2021 | Gifford et al. |
| 2021/0196462 | A1 | 7/2021 | Khairkhahan |
| 2021/0212824 | A1 | 7/2021 | Pham et al. |
| 2021/0212825 | A1 | 7/2021 | Pham et al. |
| 2021/0275305 | A1 | 9/2021 | Pham et al. |
| 2021/0290390 | A1 | 9/2021 | Genovese et al. |
| 2021/0298896 | A1 | 9/2021 | Pham et al. |
| 2021/0298901 | A1 | 9/2021 | Khairkhahan et al. |
| 2021/0346159 | A1 | 11/2021 | Keränen |
| 2021/0353418 | A1 | 11/2021 | Mohl |
| 2022/0000621 | A1 | 1/2022 | Gifford et al. |
| 2022/0039944 | A1 | 2/2022 | Khairkhahan |
| 2022/0039951 | A1 | 2/2022 | Khairkhahan |
| 2022/0054269 | A1 | 2/2022 | Khairkhahan |
| 2022/0079753 | A1 | 3/2022 | Zimmerman et al. |
| 2022/0079755 | A1 | 3/2022 | Zimmerman et al. |
| 2022/0096234 | A1 | 3/2022 | Sorajja |
| 2022/0096236 | A1 | 3/2022 | Guidotti et al. |
| 2022/0125579 | A1 | 4/2022 | McLean et al. |
| 2022/0160499 | A1 | 5/2022 | Miyashiro et al. |
| 2022/0160508 | A1 | 5/2022 | Miyashiro et al. |
| 2022/0183837 | A1 | 6/2022 | Tuval et al. |
| 2022/0183839 | A1 | 6/2022 | Khairkhahan |
| 2022/0192822 | A1 | 6/2022 | McLean et al. |
| 2022/0233311 | A1 | 7/2022 | Khairkhahan |
| 2022/0273433 | A1 | 9/2022 | Kuck et al. |
| 2022/0296368 | A1 | 9/2022 | Tuval et al. |
| 2022/0354637 | A1 | 11/2022 | Khairkhahan |
| 2022/0354647 | A1 | 11/2022 | Khairkhahan |
| 2022/0354648 | A1 | 11/2022 | Khairkhahan |
| 2022/0362012 | A1 | 11/2022 | Khairkhahan |
| 2022/0409372 | A1 | 12/2022 | Khairkhahan |
| 2023/0040410 | A1 | 2/2023 | Khairkhahan |
| 2023/0105858 | A1 | 4/2023 | Khalil et al. |
| 2023/0107129 | A1 | 4/2023 | Mohl |
| 2023/0132907 | A1 | 5/2023 | McLean et al. |

(56) References Cited

U.S. PATENT DOCUMENTS

| | | | |
|---|---|---|---|
| 2023/0138388 | A1 | 5/2023 | Padala et al. |
| 2023/0142064 | A1 | 5/2023 | Chau et al. |
| 2023/0147741 | A1 | 5/2023 | Khairkhahan |
| 2023/0181313 | A1 | 6/2023 | Mohl et al. |
| 2023/0248518 | A1 | 8/2023 | Khairkhahan |
| 2023/0270549 | A1 | 8/2023 | Guidotti et al. |
| 2023/0277169 | A1 | 9/2023 | Khairkhahan |
| 2023/0293298 | A1 | 9/2023 | Khairkhahan |
| 2023/0293299 | A1 | 9/2023 | Khairkhahan |
| 2023/0329865 | A1 | 10/2023 | Kappetein et al. |
| 2023/0404757 | A1 | 12/2023 | Khairkhahan |
| 2023/0405190 | A1 | 12/2023 | Padala et al. |
| 2024/0016473 | A1 | 1/2024 | Schewel et al. |
| 2024/0033083 | A1 | 2/2024 | Khairkhahan |
| 2024/0041601 | A1 | 2/2024 | Khairkhahan et al. |
| 2024/0138977 | A1 | 5/2024 | Pham et al. |
| 2024/0156591 | A1 | 5/2024 | Pham et al. |
| 2024/0245512 | A1 | 7/2024 | Padala et al. |
| 2024/0366379 | A1 | 11/2024 | Khairkhahan et al. |
| 2025/0041061 | A1 | 2/2025 | Khairkhahan et al. |
| 2025/0064589 | A1 | 2/2025 | Padala |
| 2025/0099241 | A1 | 3/2025 | Zimmerman et al. |
| 2025/0099247 | A1 | 3/2025 | Khairkhahan et al. |
| 2025/0186205 | A1 | 6/2025 | McLean et al. |
| 2025/0262055 | A1 | 8/2025 | Khairkhahan |
| 2025/0318926 | A1 | 10/2025 | Padala et al. |
| 2025/0381034 | A1 | 12/2025 | Khairkhahan et al. |
| 2026/0047931 | A1 | 2/2026 | Khairkhahan et al. |
| 2026/0096812 | A1 | 4/2026 | Khairkhahan et al. |
| 2026/0096884 | A1 | 4/2026 | Khairkhahan |
| 2026/0144638 | A1 | 5/2026 | Khairkhahan et al. |

FOREIGN PATENT DOCUMENTS

| | | | |
|---|---|---|---|
| CN | 101056596 | | 10/2007 |
| CN | 101068508 | | 11/2007 |
| CN | 101947146 | | 1/2011 |
| CN | 102065777 | | 5/2011 |
| CN | 102458309 | | 5/2012 |
| CN | 102665612 | | 9/2012 |
| CN | 102781790 | | 11/2012 |
| CN | 102933175 | | 2/2013 |
| CN | 202821715 | | 3/2013 |
| CN | 103118602 | | 5/2013 |
| CN | 103338726 | | 10/2013 |
| CN | 104203158 | | 12/2014 |
| CN | 102905648 | | 1/2015 |
| CN | 104394803 | | 3/2015 |
| CN | 104582637 | | 4/2015 |
| CN | 105287050 | | 2/2016 |
| CN | 105451688 | | 3/2016 |
| CN | 106061437 | | 10/2016 |
| EP | 1 294 310 | | 3/2003 |
| EP | 1 959 865 | | 8/2008 |
| EP | 2 410 948 | | 2/2012 |
| EP | 1 796 597 | | 1/2013 |
| EP | 2 661 239 | | 11/2013 |
| EP | 2 667 824 | | 12/2013 |
| EP | 2 995 279 | | 3/2016 |
| EP | 3 160 396 | | 5/2017 |
| EP | 3 167 846 | | 5/2017 |
| EP | 3 372 198 | | 9/2018 |
| EP | 3 658 075 | | 6/2020 |
| EP | 3 768 195 | | 1/2021 |
| EP | 3 852 681 | | 7/2021 |
| EP | 3 880 124 | | 9/2021 |
| EP | 3 911 272 | | 11/2021 |
| EP | 3 912 595 | | 11/2021 |
| EP | 3 157 469 | | 12/2021 |
| EP | 4 084 738 | | 11/2022 |
| EP | 4 171 443 | | 5/2023 |
| JP | S54-088693 | | 7/1979 |
| JP | 2005-535384 | | 11/2005 |
| JP | 2006-528911 | | 12/2006 |
| JP | 2007-518492 | | 7/2007 |
| JP | 2008-517672 | | 5/2008 |
| JP | 2010-511469 | | 4/2010 |
| JP | 2012-511402 | | 5/2012 |
| JP | 2012-520716 | | 9/2012 |
| JP | 2014-510563 | | 5/2014 |
| JP | 2014-231015 | | 12/2014 |
| JP | 2015-523898 | | 8/2016 |
| JP | 2016-533798 | | 11/2016 |
| JP | 2017-18675 | | 1/2017 |
| JP | 2019-500965 | | 1/2019 |
| JP | 2020-506007 | | 2/2020 |
| JP | 2020-127779 | | 8/2020 |
| JP | 2020-532402 | | 11/2020 |
| WO | WO 97/007744 | | 3/1997 |
| WO | WO 99/53869 | | 10/1998 |
| WO | WO 2004/014258 | | 2/2004 |
| WO | WO 2004/100803 | | 11/2004 |
| WO | WO 2004/103162 | | 12/2004 |
| WO | WO 2005/069875 | | 8/2005 |
| WO | WO 2006/032051 | | 3/2006 |
| WO | WO 2006/041877 | | 4/2006 |
| WO | WO 2006/086434 | | 8/2006 |
| WO | WO 2007/062054 | | 5/2007 |
| WO | WO 2007/135101 | | 11/2007 |
| WO | WO 2007/140470 | | 12/2007 |
| WO | WO 2008/068756 | | 6/2008 |
| WO | WO 2008/141322 | | 11/2008 |
| WO | WO 2010/106438 | | 9/2010 |
| WO | WO 2011/037891 | | 3/2011 |
| WO | WO 2011/047168 | | 4/2011 |
| WO | WO 2012/061809 | | 5/2012 |
| WO | WO 2012/092437 | | 7/2012 |
| WO | WO 2012/102928 | | 8/2012 |
| WO | WO 2013/059747 | | 4/2013 |
| WO | WO 2013/131069 | | 9/2013 |
| WO | WO 2013/173587 | | 11/2013 |
| WO | WO 2013/178335 | | 12/2013 |
| WO | WO 2013/192107 | | 12/2013 |
| WO | WO 2014/181336 | | 11/2014 |
| WO | WO 2014/207575 | | 12/2014 |
| WO | WO 2015/020971 | | 2/2015 |
| WO | WO 2015/052570 | | 4/2015 |
| WO | WO 2015/061533 | | 4/2015 |
| WO | WO 2015/195823 | | 12/2015 |
| WO | WO 2015/200497 | | 12/2015 |
| WO | WO 2016/059639 | | 4/2016 |
| WO | WO 2016/178136 | | 11/2016 |
| WO | WO 2016/183485 | | 11/2016 |
| WO | WO 2017/079279 | | 5/2017 |
| WO | WO 2017/120404 | | 7/2017 |
| WO | WO 2017/136596 | | 8/2017 |
| WO | WO 2018/169878 | | 9/2018 |
| WO | WO 2018/169878 | A1 | 9/2018 |
| WO | WO 2019/116322 | | 6/2019 |
| WO | WO 2019/157331 | | 8/2019 |
| WO | WO 2019/222694 | | 11/2019 |
| WO | WO 2019/241777 | | 12/2019 |
| WO | WO 2020/055811 | | 3/2020 |
| WO | WO 2021/055983 | | 3/2021 |
| WO | WO 2021/138053 | | 7/2021 |
| WO | WO 2022/006087 | | 1/2022 |
| WO | WO 2022/018494 | | 1/2022 |
| WO | WO 2022/132424 | | 6/2022 |
| WO | WO 2022/272189 | | 12/2022 |
| WO | WO 2023/105334 | | 6/2023 |
| WO | WO 2023/114289 | | 6/2023 |
| WO | WO 2023/218127 | | 11/2023 |
| WO | WO 2024/229113 | | 11/2024 |

OTHER PUBLICATIONS

Biocina, The arteficial coaptation surface concept in mitral valve repair, University of Zagreb School of Medicine, Department of Cardiac Surgery, Savudrija Mitrofast 2010.

Chiam et al., Percutaneous Transcatheter Mitral Valve Repair, The American College of Cardiology Foundation, JACC: Cardiovascular Interventions, vol. 4 No. 1, Jan. 2011:1-13.

(56) References Cited

OTHER PUBLICATIONS

Jassar et al., Posterior Leaflet Augmentation in Ischemic Mitral Regurgitation Increases Leaflet Coaptation and Mobility, The Society of Thoracic Surgeons, Ann Thorac Surg 2012; 94:1438-45.
Langer et al., Posterior mitral leaflet extension: An adjunctive repair option for ischemic mitralregurgitation?, Surgery for Acquired Cardiovascular Disease, The Journal of Thoracic and Cardiovascular Surgery, Apr. 2006, downloaded Jun. 18, 2011.
Mohl et al., The Angel Valve Concept, Vienna University of Technology, Medical University of Vienna, Technology Offer, 1 page.
Mohl et al., An Innovative Concept For Transcatheter Treatment of Annular Dilatation and Restrictive Leaflet Motion in Mitral Insufficiency, Medical University of Vienna, 1 page.
Piemonte et al., Cardiovascular™: The Mitral Valve Spacer, Presented at Transcatheter Cardiovascular Therapeutics Conference—TCT Conference, Oct. 2008.
Rumel et al, The Correction of Mitral Insufficiency with a Trans-Valvular Polyvinyl Formalinized Plastic (Ivalon) Sponge Prosthesis: A Preliminary Report, American College of Chest Physicians, 1958;33;401-413, Dec. 2, 2010.
International Preliminary Report on Patentability for PCT/US2012/021744 mailed Aug. 8, 2013 in 15 pages.
International Search Report for Application No. PCT/US2013/046173 dated Oct. 4, 2013 in 15 pages.
International Search Report for Application No. PCT/US2014/061901 dated Jan. 26, 2015 in 14 pages.
International Search Report for Application No. PCT/US2015/036260 dated Oct. 1, 2015 in 20 pages.
International Search Report for Application No. PCT/US2015/037451 dated Oct. 6, 2015 in 12 pages.
International Search Report for Application No. PCT/US2016/060094 dated Feb. 9, 2017 in 8 pages.
International Search Report for Application No. PCT/US2018/022043 dated Jun. 25, 2018 in 13 pages.
Extended European Search Report, EP 12738989.8, dated May 24, 2016.
Office Action for EP 12738989.8 dated Mar. 3, 2017.
Office Action for EP 12738989.8 dated Sep. 19, 2017.
Extended European Search Report, EP 13806272.4, dated Nov. 11, 2015.
Extended European Search Report, EP 14856738.1, dated Jun. 7, 2017.
Extended European Search Report, EP 15809346.8, dated Feb. 13, 2018.
Extended European Search Report, EP 15812032.9, dated Oct. 18, 2017.
Extended European Search Report, EP 16862864.2, dated May 10, 2019.
Office Action for CA 2,825,520 dated Nov. 27, 2017.
Office Action for CA 2,825,520 dated Aug. 21, 2018.
Office Action for CA 2,877,344 dated Mar. 12, 2019.
Office Action for CA 2,877,344 dated Oct. 9, 2019.
Office Action for CA 2,877,344 dated Jul. 21, 2020.
Office Action for CN 201280006673.7 dated Dec. 10, 2014.
Office Action for CN 201280006673.7 dated Sep. 22, 2015.
Office Action for CN 201280006673.7 dated Feb. 1, 2016.
Office Action for CN 201380044122.4 dated Nov. 4, 2015.
Office Action for CN 201380044122.4 dated Aug. 24, 2016.
Office Action for CN 201480070933.6 dated May 10, 2017.
Office Action for CN 201480070933.6 dated Dec. 25, 2017.
Office Action for CN 201480070933.6 dated Aug. 10, 2018.
Office Action for CN 201480070933.6 dated Apr. 17, 2019.
Office Action for CN 201580044329.0 dated Jan. 17, 2018.
Office Action for CN 201580044329.0 dated Jul. 29, 2019.
Office Action for CN 201580045375.2 dated Mar. 29, 2018.
Office Action for CN 201580045375.2 dated Nov. 12, 2018.
Office Action for CN 201680077877.8 dated Aug. 15, 2019.
Office Action for EP 15812032.9, dated Oct. 10, 2019.
Office Action for JP 2013-552015 dated Dec. 7, 2015.
Office Action for JP 2013-552015 dated Oct. 7, 2016.
Office Action for JP 2013-552015 dated Jun. 5, 2017.
Office Action for JP 2015-518499 dated Feb. 27, 2017.
Office Action for JP 2015-518499 dated Aug. 31, 2017.
Office Action for JP 2015-518499 dated Aug. 20, 2018.
Office Action for JP 2016-525999 dated Jul. 9, 2018.
Office Action for JP 2016-525999 dated Jun. 27, 2019.
Office Action for JP 2016-525999 dated Mar. 16, 2020.
Office Action for 2016-573983 dated Apr. 1, 2019.
Office Action for 2016-573983 dated Nov. 11, 2019.
Office Action for JP 2016-574967 dated May 7, 2019.
Office Action for JP 2016-574967 dated Dec. 26, 2019.
International Search Report for Application No. PCT/US2019/050331 dated Jan. 23, 2020 in 9 pages.
Office Action for CN 201580044329.0 dated Mar. 3, 2020.
Office Action for 2016-573983 dated May 11, 2020.
Office Action for CN 201580044329.0 dated Aug. 26, 2020.
Office Action for EP 15812032.9, dated Jul. 6, 2020.
Office Action for JP 2016-574967 dated Jun. 29, 2020.
Office Action for JP 2018-543021 dated Oct. 27, 2020.
Office Action for CA 2,877,344 dated Dec. 23, 2020.
Office Action for CA 2,934,182 dated Dec. 9, 2020.
Office Action for JP 2020-082001 dated Mar. 29, 2021.
Extended European Search Report, EP 18768736.3, dated Oct. 9, 2020.
International Search Report for Application No. PCT/US2020/065261 dated Apr. 13, 2021 in 13 pages.
Office Action for CN 201880031519.2 dated May 19, 2021.
Office Action for EP 13806272.4, dated Mar. 23, 2021.
Office Action for EP 14856738.1, dated Apr. 23, 2021.
Office Action for JP 2020-085273 dated May 31, 2021.
Office Action for CA 2,934,182 dated Jun. 30, 2021.
Office Action for CA 2,958,065 dated Jul. 9, 2021.
Office Action for JP 2018-543021 dated Oct. 4, 2021.
Office Action for JP 2020-085273 dated Aug. 23, 2021.
Office Action for JP 2020-082001 dated Nov. 29, 2021.
Office Action for CA 2,934,182 dated Mar. 2, 2022.
Office Action for CA 2,958,065 dated Mar. 2, 2022.
Office Action for 2020-041944 dated Feb. 21, 2022.
Office Action for 2019-572351 dated Feb. 28, 2022.
International Search Report for Application No. PCT/US2021/016248 dated Mar. 29, 2022 in 15 pages.
Extended European Search Report, EP 19860754.1 dated Jun. 1, 2022.
International Search Report for Application No. PCT/US2022/071235 dated Jun. 27, 2022 in 13 pages.
Office Action for 2020-041944 dated Jul. 22, 2022.
Office Action for 2019-572351 dated Sep. 12, 2022.
Office Action for CN 202010539957.9 dated Nov. 3, 2022.
Office Action for JP 2021-212699 dated Dec. 6, 2022.
Office Action for JP 2021-153169 dated Dec. 26, 2022.
Office Action for CA 2,958,065 dated Nov. 18, 2022.
Office Action for JP 2021-176431 dated Jan. 6, 2023.
Office Action for 2020-041944 dated Feb. 13, 2023.
Office Action for CN 202010539957.9 dated Mar. 22, 2023.
Extended European Search Report, EP 22214458, dated Mar. 24, 2023.
Office Action for CA 3,004,418 dated Dec. 13, 2022.
Office Action for 2021-513859 dated Jun. 14, 2023.
Office Action for JP 2021-153169 dated Jul. 3, 2023.
Office Action for JP 2021-176431 dated Jul. 24, 2023.
Summons to attend oral proceedings, EP 15809346.8, dated Jun. 7, 2023.
Office Action for JP 2022-164138 dated Jul. 31, 2023.
Opposition to EP 3370650 filed Sep. 21, 2023.
Lasala, John M., and Jason H. Rogers. Interventional Procedures for Adult Structural Heart Disease. Elsevier/Saunders, 2014.
Hill, Arthur C et al. "Novel mitral repair device for the treatment of severe mitral regurgitation: preclinical ovine acute and chronic implantation model." Innovations (Philadelphia, Pa.) vol. 9,6 (2014): 432-8. doi:10.1177/155698451400900607.
Iaizzo, Paul A. Handbook of Cardiac Anatomy, Physiology, and Devices. United States, Humana Press, 2009.

(56) References Cited

OTHER PUBLICATIONS

Sonne, Carolin et al. "Age and body surface area dependency of mitral valve and papillary apparatus parameters: assessment by real-time three-dimensional echocardiography." European journal of echocardiography: the journal of the Working Group on Echocardiography of the European Society of Cardiology vol. 10,2 (2009): 287-94. doi:10.1093/ejechocard/jen237.
Opposition to EP 3157469 filed Sep. 14, 2022.
Office Action for JP 2021-212699 dated Sep. 19, 2023.
Office Action for CN 201980059862.2 dated Nov. 29, 2023.
Office Action for JP 2023-039771 dated Dec. 4, 2023.
Extended European Search Report, EP 20910735.8, dated Jan. 8, 2024.
Summons to Attend Oral Proceedings, EP 13806272.4, dated Feb. 9, 2024.
Office Action for JP 2021-212699 dated Mar. 18, 2024.
Office Action for JP 2022-164138 dated Mar. 18, 2024.
Office Action for 2021-513859 dated Mar. 18, 2024.
Interlocutory Decision EP 15809346.8, dated Mar. 19, 2024.
Office Action for CN 202110375324.3 dated Apr. 30, 2024.
International Search Report and Written Opinion for Application No. PCT/US2024/027244 dated Sep. 25, 2024 in 16 pages.
Office Action for CA 3,056,426 dated Feb. 16, 2024.
Office Action for EP19860754.1 dated May 29, 2024.
Office Action for 2023-213880 dated Jul. 16, 2024.
Invitation to Pay Additional Search Fees for PCT/US2024/027244 dated Jul. 30, 2024.
Office Action for JP 2023-039771 dated Aug. 13, 2024.
Extended European Search Report, EP21907438.2, dated Sep. 30, 2024.
Office Action for JP 2022-537714 dated Oct. 21, 2024.
Office Action for CN 202111212597.2 dated Jan. 8, 2025.
Office Action for 2023-213880 dated Jan. 15, 2025.
Office Action for JP 2023-039771 dated Mar. 11, 2025.
Office Action for CN 202080084279.X dated Mar. 15, 2025.
Office Action for CA 2,958,061 dated Apr. 9, 2025.
Extended European Search Report, EP 22829471.6, dated May 15, 2025.
Office Action for CN 202210297940.6 dated May 24, 2025.
Office Action for CN 202210297939.3 dated May 24, 2025.
|Office Action for JP Application No. 2024-080097, dated Jun. 24, 2025; in 4 pages.
Office Action for JP 2022-537714 dated Jul. 29, 2025.
Office Action for JP 2023-536524 dated Sep. 30, 2025.
Office Action for CA 3,056,426 dated Oct. 21, 2025.
Office Action for 2023-213880 dated Oct. 14, 2025.
Office Action for JP Application No. 2023-579327 dated Dec. 2, 2025.
Office Action for CN Application No. 202111212597.2 dated Jan. 13, 2026.
Office Action for JP Application No. 2024-080097, dated Mar. 10, 2026.
Office Action for CN Application No. 202210297940.6, dated Mar. 11, 2026; 13 pages.
Office Action for CN Application No. 202210297939.3 dated Mar. 14, 2026; in 13 pages.
Office Action for EP Application No. 21907438.2 dated Feb. 5, 2026; in 8 pages.
Office Action for 2023-213880 dated Apr. 21, 2026.
Office Action for CA 3,161,977 dated May 13, 2026.

* cited by examiner (Non-limiting example dimensions)

DIMENSIONS TABLE (TABLE 1)

| Dimension | From (Min) | To (Max) | One Embodiment |
|---|---|---|---|
| X | 20mm | 60mm | 35mm |
| Y | 5mm | 35mm | 15mm |
| Z | 10mm | 40mm | 25mm |

(Non-limiting examples of dimensions)
TABLE 2

| Material: Nitinol | | | | |
|---|---|---|---|---|
| A-A Variation | Behavior characteristics | Characteristic dimension | Dimensions (Range) | Dimensions (One Embodiment) |
| 550.1 | Good fatigue characteristics Bends equally in all directions | Diameter | 0.010" to .060" | 0.018" |
| 550.2 | Better fatigue characteristics Bends equally in all directions | Diameter | 0.010" to .060" | 0.018" |
| 550.3 | Highly flexible | Diameter | 0.010" to .040" | 0.022" |
| 550.4 | Good fatigue characteristics | Width | 0.010" to 0.06" | 0.025" |
| | Unidirectional bending characteristics | Aspect Ratio (Width/ thickness) | 1.1 to 3.0 | 1.5 |
| 550.5 | Good fatigue characteristics | Width | 0.010" to 0.06" | 0.025" |
| | Unidirectional bending characteristics | Aspect Ratio (Width/ thickness) | 1.1 to 3.0 | 1.5 |

| Material: PEEK | | | | |
|---|---|---|---|---|
| A-A Variation | Behavior characteristics | Characteristic dimension | Dimensions (Range) | Dimensions (One Embodiment) |
| 550.4 | Good fatigue characteristics | Width | 0.010" to 0.050" | 0.080" |
| | Unidirectional bending characteristics | Aspect Ratio (Width/ thickness) | 1.1 to 20.0 | 10 |
| 550.5 | Good fatigue characteristics | Width | 0.010" to 0.050" | 0.080" |
| | Unidirectional bending characteristics | Aspect Ratio (Width/ thickness) | 1.1 to 20.0 | 10 |

FIG. 5E

MITRAL VALVE IMPLANTS FOR THE TREATMENT OF VALVULAR REGURGITATION

The present application is a continuation of U.S. patent application Ser. No. 16/705,605 filed Dec. 6, 2019, which is a continuation of U.S. patent application Ser. No. 14/742,199 filed Jun. 17, 2015, which in turn claims priority under 35 U.S.C. 119 (e) to U.S. Provisional Application No. 62/014,060, titled "Mitral Valve Implants for the Treatment of Valvular Regurgitation" and filed Jun. 18, 2014. Each of the foregoing applications of which are hereby incorporated by reference in their entireties. Any and all applications for which a foreign or domestic priority claim is identified in the Application Data Sheet as filed with the present application, are hereby incorporated by reference in their entirety under 37 CFR 1.57.

BACKGROUND

Field

The present invention generally provides improved medical devices, systems, and methods, typically for treatment of heart valve disease and/or for altering characteristics of one or more valves of the body. Embodiments of the invention include implants for treatment of mitral valve regurgitation.

The human heart receives blood from the organs and tissues via the veins, pumps that blood through the lungs where the blood becomes enriched with oxygen, and propels the oxygenated blood out of the heart to the arteries so that the organ systems of the body can extract the oxygen for proper function. Deoxygenated blood flows back to the heart where it is once again pumped to the lungs.

The heart includes four chambers: the right atrium (RA), the right ventricle (RV), the left atrium (LA) and the left ventricle (LV). The pumping action of the left and right sides of the heart occurs generally in synchrony during the overall cardiac cycle.

The heart has four valves generally configured to selectively transmit blood flow in the correct direction during the cardiac cycle. The valves that separate the atria from the ventricles are referred to as the atrioventricular (or AV) valves. The AV valve between the left atrium and the left ventricle is the mitral valve. The AV valve between the right atrium and the right ventricle is the tricuspid valve. The pulmonary valve directs blood flow to the pulmonary artery and thence to the lungs; blood returns to the left atrium via the pulmonary veins. The aortic valve directs flow through the aorta and thence to the periphery. There are normally no direct connections between the ventricles or between the atria.

The mechanical heartbeat is triggered by an electrical impulse which spreads throughout the cardiac tissue. Opening and closing of heart valves may occur primarily as a result of pressure differences between chambers, those pressures resulting from either passive filling or chamber contraction. For example, the opening and closing of the mitral valve may occur as a result of the pressure differences between the left atrium and the left ventricle.

At the beginning of ventricular filling (diastole) the aortic and pulmonary valves are closed to prevent back flow from the arteries into the ventricles. Shortly thereafter, the AV valves open to allow unimpeded flow from the atria into the corresponding ventricles. Shortly after ventricular systole (i.e., ventricular emptying) begins, the tricuspid and mitral valves normally shut, forming a seal which prevents flow from the ventricles back into the corresponding atria.

Unfortunately, the AV valves may become damaged or may otherwise fail to function properly, resulting in improper closing. The AV valves are complex structures that generally include an annulus, leaflets, chordae and a support structure. Each atrium interfaces with its valve via an atrial vestibule. The mitral valve has two leaflets; the analogous structure of the tricuspid valve has three leaflets, and opposition or engagement of corresponding surfaces of leaflets against each other helps provide closure or sealing of the valve to prevent blood flowing in the wrong direction. Failure of the leaflets to seal during ventricular systole is known as malcoaptation, and may allow blood to flow backward through the valve (regurgitation). Heart valve regurgitation can have serious consequences to a patient, often resulting in cardiac failure, decreased blood flow, lower blood pressure, and/or a diminished flow of oxygen to the tissues of the body. Mitral regurgitation can also cause blood to flow back from the left atrium to the pulmonary veins, causing congestion. Severe valvular regurgitation, if untreated, can result in permanent disability or death.

Description of the Related Art

A variety of therapies have been applied for treatment of mitral valve regurgitation, and still other therapies may have been proposed but not yet actually used to treat patients. While several of the known therapies have been found to provide benefits for at least some patients, still further options would be desirable. For example, pharmacologic agents (such as diuretics and vasodilators) can be used with patients having mild mitral valve regurgitation to help reduce the amount of blood flowing back into the left atrium. However, medications can suffer from lack of patient compliance. A significant number of patients may occasionally (or even regularly) fail to take medications, despite the potential seriousness of chronic and/or progressively deteriorating mitral valve regurgitation. Pharmacological therapies of mitral valve regurgitation may also be inconvenient, are often ineffective (especially as the condition worsens), and can be associated with significant side effects (such as low blood pressure).

A variety of surgical options have also been proposed and/or employed for treatment of mitral valve regurgitation. For example, open-heart surgery can replace or repair a dysfunctional mitral valve. In annuloplasty ring repair, the posterior mitral annulus can be reduced in size along its circumference, optionally using sutures passed through a mechanical surgical annuloplasty sewing ring to provide coaptation. Open surgery might also seek to reshape the leaflets and/or otherwise modify the support structure. Regardless, open mitral valve surgery is generally a very invasive treatment carried out with the patient under general anesthesia while on a heart-lung machine and with the chest cut open. Complications can be common, and in light of the morbidity (and potentially mortality) of open-heart surgery, the timing becomes a challenge-sicker patients may be in greater need of the surgery, but less able to withstand the surgery. Successful open mitral valve surgical outcomes can also be quite dependent on surgical skill and experience.

Given the morbidity and mortality of open-heart surgery, innovators have sought less invasive surgical therapies. Procedures that are done with robots or through endoscopes are often still quite invasive, and can also be time consuming, expensive, and in at least some cases, quite dependent on the surgeon's skill. Imposing even less trauma on these sometimes frail patients would be desirable, as would be providing therapies that could be successfully implemented by a significant number of physicians using widely distributed skills. Toward that end, a number of purportedly less invasive technologies and approaches have been proposed. These include devices which seek to re-shape the mitral annulus from within the coronary sinus; devices that attempt to reshape the annulus by cinching either above to below the native annulus; devices to fuse the leaflets (imitating the Alfieri stitch); devices to re-shape the left ventricle, and the like.

Perhaps most widely known, a variety of mitral valve replacement implants have been developed, with these implants generally replacing (or displacing) the native leaflets and relying on surgically implanted structures to control the blood flow paths between the chambers of the heart. While these various approaches and tools have met with differing levels of acceptance, none has yet gained widespread recognition as an ideal therapy for most or all patients suffering from mitral valve regurgitation.

Because of the challenges and disadvantages of known minimally invasive mitral valve regurgitation therapies and implants, still further alternative treatments have been proposed. Some of the alternative proposals have called for an implanted structure to remain within the valve annulus throughout the heart beat cycle. One group of these proposals includes a cylindrical balloon or the like to remain implanted on a tether or rigid rod extending between the atrium and the ventricle through the valve opening. Another group relies on an arcuate ring structure or the like, often in combination with a buttress or structural cross-member extending across the valve so as to anchor the implant. Unfortunately, sealing between the native leaflets and the full perimeter of a balloon or other coaxial body may prove challenging, while the significant contraction around the native valve annulus during each heart beat may result in significant fatigue failure issues during long-term implantation if a buttress or anchor interconnecting cross member is allowed to flex. Moreover, the significant movement of the tissues of the valve may make accurate positioning of the implant challenging regardless of whether the implant is rigid or flexible.

In light of the above, it would be desirable to provide improved medical devices, systems, and methods. It would be particularly desirable to provide new techniques for treatment of mitral valve regurgitation and other heart valve diseases, and/or for altering characteristics of one or more of the other valves of the body. The need remains for a device which can directly enhance leaflet coaptation (rather than indirectly via annular or ventricular re-shaping) and which does not disrupt leaflet anatomy via fusion or otherwise, but which can be deployed simply and reliably, and without excessive cost or surgical time. It would be particularly beneficial if these new techniques could be implemented using a less-invasive approach, without stopping the heart or relying on a heart-lung machine for deployment, and without relying on exceptional skills of the surgeon to provide improved valve and/or heart function.

SUMMARY

In some embodiments, disclosed herein is an implant for treating mal-coaptation of a heart valve. The implant can include one or more of a shape memory structure, a biocompatible membrane coupled to the structure, a hub placed on the proximal side of the implant and coupled to the membrane, one, two, or more holes or perforations along the edge of the membrane on the proximal side, and a ventricular projection coupled to an anchoring device. The implant can be folded for delivery through a percutaneous catheter. A shape memory structure can include a shape memory spine, such as nitinol or PEEK for example. A part of the ventricular projection, such as the distal tip, can be radiopaque. The anchoring device could be active, or passive. The spine can include features such as microholes and microhooks for coupling to the membrane and tissue.

Also disclosed herein is a steerable catheter that includes one or more of a steerable shaft, a rotatable handle that is coupled to a pullwire placed within the shaft to adjust the bend radius of the distal tip of the shaft depending on the amount of torque applied to the handle. In some embodiments, the diameter of the handle of the catheter is equal to the diameter of the steerable shaft, or no larger than the diameter of the steerable shaft. Also disclosed herein is a delivery catheter comprising one or more of the following: a rotatable handle coupled to a pullwire placed within a torqueable shaft to adjust the bend radius of the distal tip of the shaft of the catheter, a sheath designed to contain the implant when the implant is folded, and distal tip further comprising of locking features that enable coupling of delivery catheter to either a hub of an implant or to an anchor. In some embodiments, the catheter can also include a tearable and disposable funnel to aid in the folding of the implant. In some embodiments, the distal tip further comprises locking tabs which are naturally set to be in the unlocked position. The delivery catheter may be coupled to the annular hub of the implant which has features that accept the locking tabs of the delivery catheter. In some embodiments, a guidewire or another catheter may be inserted within the shaft to push the locking tabs to the companion features on the hub of the implant so that the catheter and the hub are locked. The catheter can also include a loop, such as wire running from the proximal handle to the distal tip such that the tension in the loop may be controlled via control on the handle. The delivery catheter may be coupled to the annular hub of the implant which has a cross pin. A guidewire or another catheter may be inserted within the shaft and the loop of wire is tensioned against the cross-pin and the guidewire such that the delivery catheter is locked to the hub of the implant until the tension on the loop is maintained.

An implant can be operatively coupled to tissue, such as heart tissue, via a first coupling of the anchor to the delivery catheter, and a second coupling of the anchor to the implant hub where torque is applied to the delivery catheter to insert the anchor into the hub and the tissue. The first coupling can be uncoupled to retract the catheter.

In some embodiments, commissure anchors can be delivered by one or more of the following steps: coupling an anchor to a shaft of a catheter, advancing the anchor and the catheter to an anchor site, delivering the anchor such that it engages with the implant and tissue, and uncoupling the anchor from the shaft. The shaft can be torqueable, and the engaging mechanism can apply torque to the shaft so that the anchor engages with the implant and tissue. The anchors can be made of shape memory materials and be compressed into the shaft of a catheter for delivery to the anchor site, where the distal tip of the catheter is shaped such that it pierces tissue. The anchors can be advanced after the delivery catheter first pierces the tissue and subsequently the catheter is retracted leaving the anchor in place.

In some embodiments, disclosed is an implant for treating mal-coaptation of a heart valve. The implant can include one or more of the following: a removable shape memory structure, a biocompatible membrane coupled to the structure, a hub placed on the proximal side of the implant and coupled to the membrane, one, two, or more holes or perforations along the edge of the membrane on the proximal side, and a ventricular projection coupled to an anchoring device. The implant can also include at least one passageway, such as a passageway placed around the annular edge, and/or along the ventricular projection. In some embodiments, a plurality, such as 2, 3, 4, 5, or more anchors are delivered to couple an implant to the heart tissue. A delivery device can have a distal section that includes 1, 2, or more anchors rotationally coupled to a central spinning shaft. A spring-loaded mechanism can apply a pushing force so as to cause the anchors to exit the distal end. In some embodiments, the anchors can be housed in a housing with grooves on the inside diameter such that as the central spinning shaft rotates, the anchors may exit the distal end. The device can include one or more of, for example, a hollow shaft, a pointed end at the end of the hollow shaft, one, two, or more hollow barrels placed within the hollow shaft threaded by a wire, and a pusher at the proximal end such that when a force is applied to the pusher, the barrels exit the hollow shaft one by one.

In some embodiments, disclosed herein is a steerable guidewire, comprising an elongate flexible body, having a longitudinal axis, a proximal end and a distal deflection zone; a control on the proximal end, for controllable deflection of the deflection zone; and a movable deflection element extending from the control to the deflection zone. In some embodiments, no portion of the guidewire has an outside diameter of greater than about 10 French, 8 French, 6 French, or 4 French. The control can have an outside diameter that is no greater than the outside diameter of the body. Rotation of the control about the axis can cause lateral movement of the deflection zone. Rotation of the control in a first direction about the axis can cause proximal retraction of the deflection element.

Also disclosed herein is an implantable coaptation assistance device, comprising a flexible body; a first, concave surface on the body, configured to restrain a posterior leaflet; a second, convex surface on the body, configured to contact an anterior leaflet; an arcuate, peripheral superior edge on the body defining an opening which faces away from the first surface; and a ventricular projection extending away from the body and configured to anchor in the ventricle. The device can also include an anchor on the ventricular projection. The anchor could be active or passive. The device can also include a flexible spine for supporting the arcuate peripheral edge. The spine can be removable in some cases.

Also disclosed herein is an anchoring system for attaching a ventricular projection of an implantable coaptation device. The system can include a shoulder, having an aperture extending therethrough; a helical tissue anchor, extending distally from the hub; a first engagement structure on the anchor, for releasable engagement of a torque shaft; a second engagement structure on the torque shaft, for engaging the anchor; and an implant, having a hub dimensioned to receive the helical anchor through; wherein the torque shaft is configured for rotation to drive the helical anchor into tissue and secure the implant to tissue. The first engagement structure can be an aperture, and the second engagement structure can be a projection. The projection can be laterally moveable into and out of the aperture, such as in response to axial movement of an elongate element within the torque shaft.

In some embodiments, a steerable guidewire is provided. The steerable guidewire can include an elongate flexible body, having a longitudinal axis, a proximal end and a distal deflection zone. The steerable guidewire can include a control on the proximal end, for controllable deflection of the deflection zone. The steerable guidewire can include a movable deflection element extending from the control to the deflection zone. In some embodiments, no portion of the guidewire has an outside diameter of greater than about 10 French. In some embodiments, no portion of the guidewire has an outside diameter of greater than about 6 French. In some embodiments, no portion of the guidewire has an outside diameter of greater than about 4 French. In some embodiments, the control has an outside diameter that is no greater than the outside diameter of the body. In some embodiments, rotation of the control about the axis causes lateral movement of the deflection zone. In some embodiments, rotation of the control in a first direction about the axis causes proximal retraction of the deflection element.

In some embodiments, an implantable coaptation assistance device is provided. The implantable coaptation assistance device can include a flexible body. The implantable coaptation assistance device can include a first, concave surface on the body, configured to restrain a posterior leaflet. The implantable coaptation assistance device can include a second, convex surface on the body, configured to contact an anterior leaflet. The implantable coaptation assistance device can include an arcuate, peripheral superior edge on the body defining an opening which faces away from the first surface. The implantable coaptation assistance device can include a ventricular projection extending away from the body and configured to anchor in the ventricle.

In some embodiments, the implantable coaptation assistance device can include an anchor on the ventricular projection. In some embodiments, the implantable coaptation assistance device can include an active anchor. In some embodiments, the implantable coaptation assistance device can include a passive anchor. In some embodiments, the implantable coaptation assistance device can include a flexible spine for supporting the arcuate peripheral edge. In some embodiments, the spine is removable.

In some embodiments, an anchoring system for attaching a ventricular projection of an implantable coaptation device is provided. The anchoring system can include a shoulder, having an aperture extending therethrough. The anchoring system can include a helical tissue anchor, extending distally from the hub. The anchoring system can include a first engagement structure on the anchor, for releasable engagement of a torque shaft. The anchoring system can include a second engagement structure on the torque shaft, for engaging the anchor. The anchoring system can include an implant, having a hub dimensioned to receive the helical anchor through. In some embodiments, the torque shaft is configured for rotation to drive the helical anchor into tissue and secure the implant to tissue. In some embodiments, the first engagement structure is an aperture, and the second engagement structure is a projection. In some embodiments, the projection is laterally moveable into and out of the aperture. In some embodiments, the projection is laterally moveable into and out of the aperture in response to axial movement of an elongate element within the torque shaft.

In some embodiments, an implantable coaptation assistance device is provided. The implantable coaptation assistance device can include a coaptation assist body comprising a first coaptation surface, an opposed second coaptation surface, each surface bounded by a first lateral edge, a second lateral edge, an inferior edge, and a superior edge. The implantable coaptation assistance device can include a ventricular projection extending from the inferior edge. The implantable coaptation assistance device can include a first support extending through at least a portion of the coaptation assist device between the superior edge and the ventricular projection. The implantable coaptation assistance device can include a second support extending through at least a portion of the coaptation assist body between the first lateral edge and the second lateral edge. The implantable coaptation assistance device can include a passageway extending through at least a portion of the coaptation assist device sized to accept a steerable catheter therethrough. In some embodiments, the first support has a first configuration wherein the first support is generally linear and a second configuration wherein the first support is curved. In some embodiments, the first and second support are configured to permit percutaneous insertion of the implantable coaptation assistance device.

In some embodiments, the passageway extends through at least a portion of the coaptation assist device between the superior edge and the ventricular projection. In some embodiments, the steerable catheter comprises a distal tip configured to curve. In some embodiments, a handle of the steerable catheter is rotated to cause the distal tip to curve. In some embodiments, the first support comprises a shape memory material. In some embodiments, the first support is bonded to the coaptation assist body. In some embodiments, the coaptation assist body comprises a lumen sized to accept at least a portion of the first support. In some embodiments, the first support is removable. In some embodiments, the first support extends from the superior edge to the ventricular projection. In some embodiments, the passageway extends through at least a portion of the coaptation assist body between the first lateral edge and the second lateral edge. In some embodiments, the second support comprises a shape memory material. In some embodiments, the second support is bonded to the coaptation assist body. In some embodiments, the coaptation assist body comprises a lumen sized to accept at least a portion of the second support. In some embodiments, the second support is removable. In some embodiments, the second support extends from the first lateral edge to the second lateral edge. In some embodiments, the first support is coupled to the second support. In some embodiments, the first support and the second support are coupled to a removable hub, the removable hub projecting from a surface of the coaptation assist body.

In some embodiments, a kit comprising is provided. The kit can include an implantable coaptation assistance device. The implantable coaptation assistance device can include a coaptation assist body comprising a first coaptation surface, an opposed second coaptation surface, each surface bounded by a first lateral edge, a second lateral edge, an inferior edge, and a superior edge. The implantable coaptation assistance device can include a ventricular projection extending from the inferior edge. The implantable coaptation assistance device can include a passageway extending through at least a portion of the coaptation assist device sized to accept a steerable catheter therethrough. The kit can include a steerable catheter. In some embodiments, the steerable catheter is configured to pass through the mitral valve and curve toward the ventricular tissue, wherein the implantable coaptation assistance device is configured to be passed over the steerable catheter toward the ventricular tissue.

In some embodiments, the passageway extends through at least a portion of the coaptation assist device between the superior edge and the ventricular projection. In some embodiments, the steerable catheter comprises a distal tip configured to curve. In some embodiments, a handle of the steerable catheter is rotated to cause the distal tip to curve.

In some embodiments, the passageway extends through at least a portion of the coaptation assist body between the first lateral edge and the second lateral edge.

In some embodiments, a method of using an implantable coaptation assistance device is provided. The method can include the step of inserting a coaptation assist body toward a heart valve. In some embodiments, the coaptation assist body comprising a first coaptation surface, an opposed second coaptation surface, each surface bounded by a first lateral edge, a second lateral edge, an inferior edge, and a superior edge, a ventricular projection extending from the inferior edge. The method can include the step of manipulating a first support to cause the coaptation assist body assume a curved configuration. In some embodiments, the first support extending through at least a portion of the coaptation assist device between the superior edge and the ventricular projection. The method can include the step of manipulating a second support to cause the coaptation assist body assume a curved configuration. In some embodiments, the second support extending through at least a portion of the coaptation assist body between the first lateral edge and the second lateral edge.

In some embodiment, manipulating a first support comprises releasing the coaptation assist body from a delivery catheter. In some embodiment, manipulating a second support comprises releasing the coaptation assist body from a delivery catheter. The method can include the step of guiding the coaptation assist body over a steerable catheter. The method can include the step of passing a steerable catheter from the ventricular projection toward the superior edge prior to inserting the coaptation assist body toward a heart valve. The method can include the step of moving a distal portion of the steerable catheter to curve around the posterior leaflet. The method can include the step of passing the coaptation assist device over the curve of the steerable catheter. In some embodiments, the steerable catheter is removed after the ventricular projection engages with ventricular tissue. In some embodiments, the steerable catheter remains in place as the ventricular projection is advanced toward the ventricular tissue. The method can include the step of removing the first support from the coaptation assist body. The method can include the step of removing the second support from the coaptation assist body. The method can include the step of engaging the ventricular projection with ventricular tissue. In some embodiments, the method is performed percutaneously.

BRIEF DESCRIPTION OF THE DRAWINGS

FIG. 5E illustrates a table of non-limiting examples of variations (materials, range of dimensions) of the support structure.

DETAILED DESCRIPTION

Figure 1A:
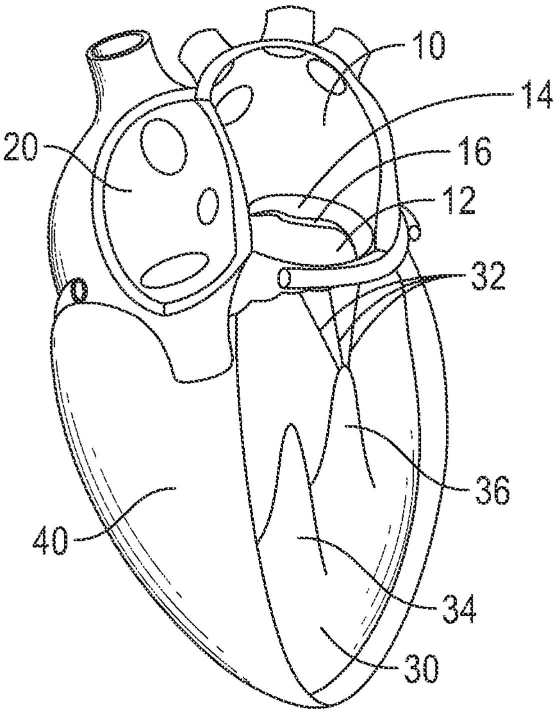
FIG. 1A-1F schematically illustrate some of the tissues of the heart and mitral valve, as described in the Background section and below, and which may interact with the implants and systems described herein
Figure 1B:
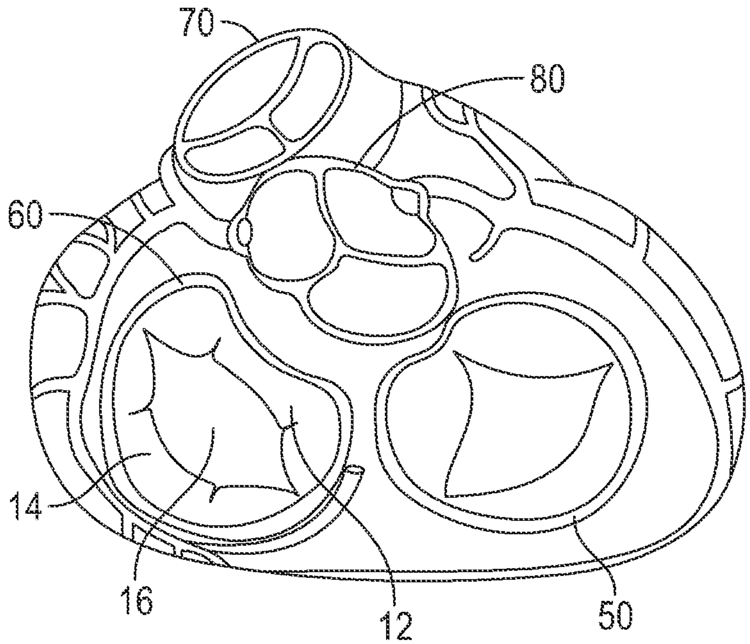
Figure 1C:
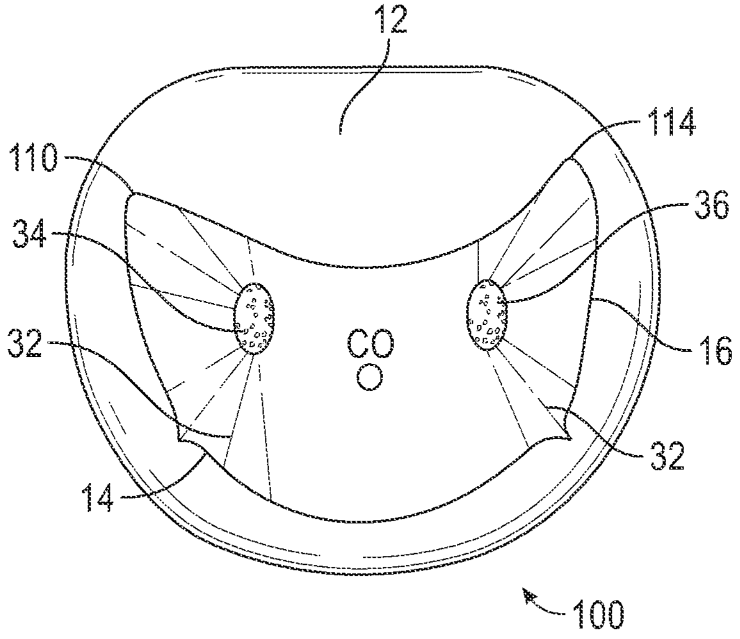
Figure 1D:
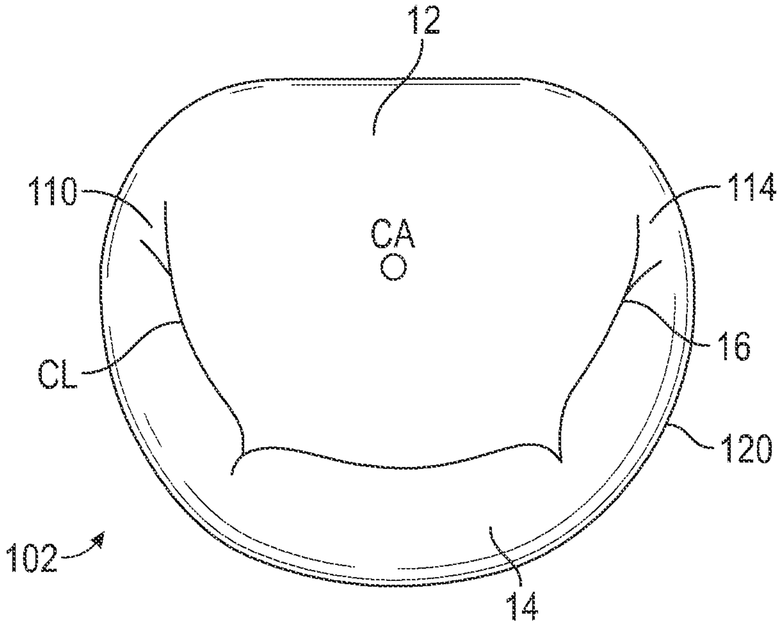

The devices, systems and methods described within this disclosure are generally for the treatment of mitral valve regurgitation (MR). Mitral valve regurgitation occurs when the mitral valve does not prevent the backflow of blood from the left ventricle to the left atrium during the systolic phase. The mitral valve is composed of two leaflets, the anterior leaflet and the posterior leaflet, which coapt or come together during the systolic phase to prevent backflow. There are generally two types of mitral valve regurgitations, functional and degenerative regurgitations. Functional MR is caused by multiple mechanisms including abnormal or impaired left ventricular (LV) wall motion, left ventricular dilation and papillary muscle disorders. Degenerative MR is caused by structural abnormalities of the valve leaflets and the sub-valvular tissue including stretching or rupture of the chordae. Damaged chordae may lead to prolapsing of the leaflets which means that the leaflets bulge out (generally into the atrium), or become flail if the chordae become torn, leading to backflows of blood. As will be described below, the devices, system and methods in this disclosure provide a new coaptation surface over the native posterior valve such that the backward flow of blood is minimized or eliminated.

Referring to FIGS. 1A-1D, the four chambers of the heart are shown, the left atrium 10, right atrium 20, left ventricle 30, and right ventricle 40. The mitral valve 60 is disposed between the left atrium 10 and left ventricle 30. Also shown are the tricuspid valve 50 which separates the right atrium 20 and right ventricle 40, the aortic valve 80, and the pulmonary valve 70. The mitral valve 60 is composed of two leaflets, the anterior leaflet 12 and posterior leaflet 14. In a healthy heart, the edges of the two leaflets oppose during systole at the coaptation zone 16.

Figure 1E:
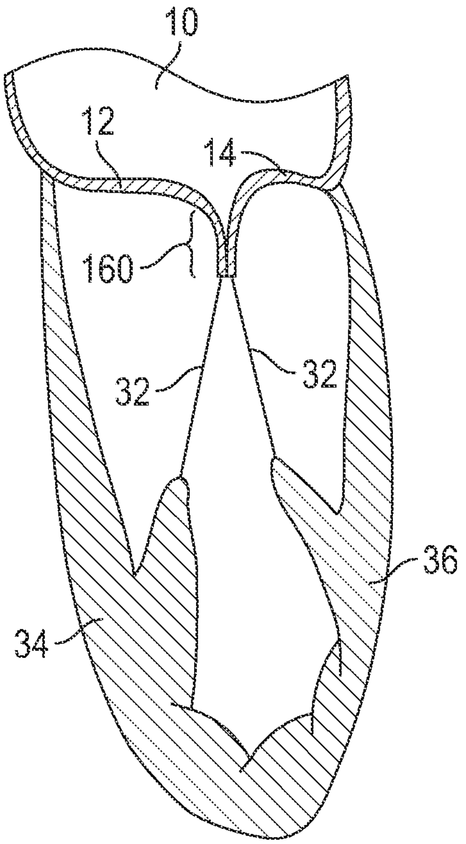

The fibrous annulus 120, part of the cardiac skeleton, provides attachment for the two leaflets of the mitral valve, referred to as the anterior leaflet 12 and the posterior leaflet 14. The leaflets are axially supported by attachment to the chordae tendinae 32. The chordae, in turn, attach to one or both of the papillary muscles 34, 36 of the left ventricle. In a healthy heart, the chordae support structures tether the mitral valve leaflets, allowing the leaflets to open easily during diastole but to resist the high pressure developed during ventricular systole. In addition to the tethering effect of the support structure, the shape and tissue consistency of the leaflets helps promote an effective seal or coaptation. The leading edges of the anterior and posterior leaflet come together along the zone of coaptation 16, with a lateral cross-section 160 of the three-dimensional coaptation zone (CZ) being shown schematically in FIG. 1E.

Figure 1F:
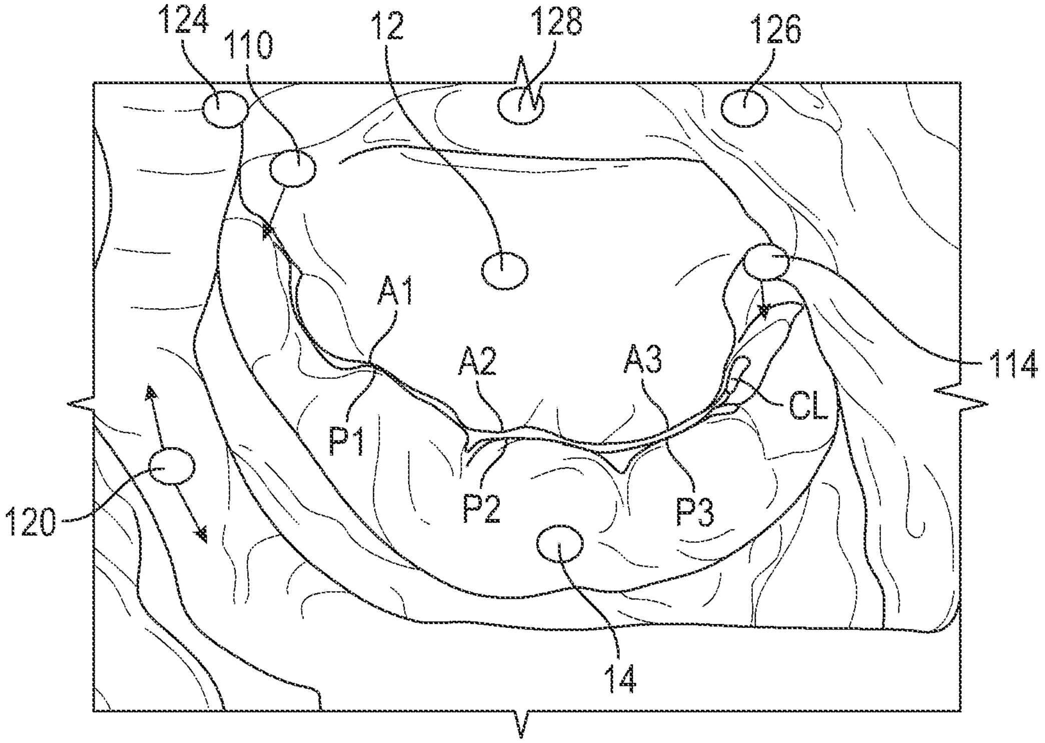

The anterior and posterior mitral leaflets are dissimilarly shaped. The anterior leaflet is more firmly attached to the annulus overlying the central fibrous body (cardiac skeleton), and is somewhat stiffer than the posterior leaflet, which is attached to the more mobile posterior mitral annulus. Approximately 80 percent of the closing area is the anterior leaflet. Adjacent to the commissures 110, 114, on or anterior to the annulus 120, lie the left (lateral) 124 and right (septal) 126 fibrous trigones which are formed where the mitral annulus is fused with the base of the non-coronary cusp of the aorta (FIG. 1F). The fibrous trigones 124, 126 form the septal and lateral extents of the central fibrous body 128. The fibrous trigones 124, 126 may have an advantage, in some embodiments, as providing a firm zone for stable engagement with one or more annular or atrial anchors. The coaptation zone CL between the leaflets 12, 14 is not a simple line, but rather a curved funnel-shaped surface interface. The first 110 (lateral or left) and second 114 (septal or right) commissures are where the anterior leaflet 12 meets the posterior leaflet 14 at the annulus 120. As seen most clearly in the axial views from the atrium of FIG. 1C, ID, and IF, an axial cross-section of the coaptation zone generally shows the curved line CL that is separated from a centroid of the annulus CA as well as from the opening through the valve during diastole CO. In addition, the leaflet edges are scalloped, more so for the posterior versus the anterior leaflet. Mal-coaptation can occur between one or more of these A-P (anterior-posterior) segment pairs A1/P1, A2/P2, and A3/P3, so that mal-coaptation characteristics may vary along the curve of the coaptation zone CL.

Figure 2A:
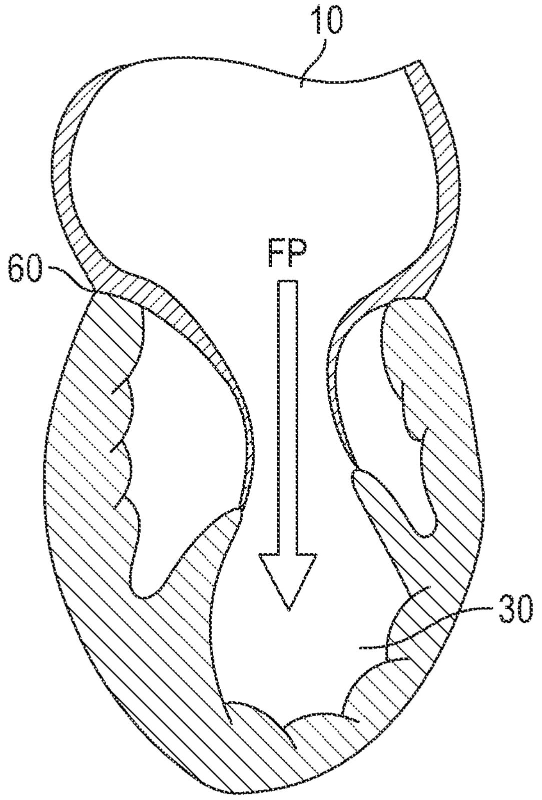
FIG. 2A illustrates a simplified cross-section of a heart, schematically showing mitral valve function during diastole.
Figure 2B:
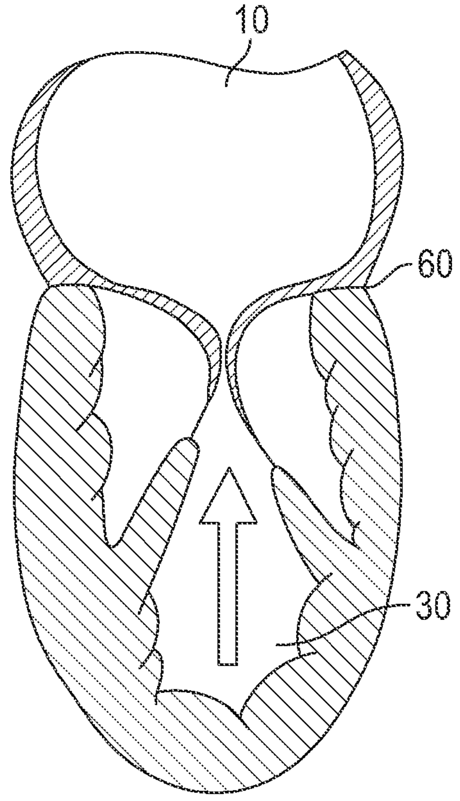
FIG. 2B illustrates a simplified cross-section of a heart, schematically showing mitral valve function during systole

Referring now to FIG. 2A, a properly functioning mitral valve 60 of a heart is open during diastole to allow blood to flow along a flow path FP from the left atrium toward the left ventricle 30 and thereby fill the left ventricle. As shown in FIG. 2B, the functioning mitral valve 60 closes and effectively seals the left ventricle 30 from the left atrium 10 during systole, first passively then actively by increase in ventricular pressure, thereby allowing contraction of the heart tissue surrounding the left ventricle to advance blood throughout the vasculature.

Referring to FIGS. 3A-3B and 4A-4B, there are several conditions or disease states in which the leaflet edges of the mitral valve fail to oppose sufficiently and thereby allow blood to regurgitate in systole from the ventricle into the atrium. Regardless of the specific etiology of a particular patient, failure of the leaflets to seal during ventricular systole is known as mal-coaptation and gives rise to mitral regurgitation.

Figure 3A:
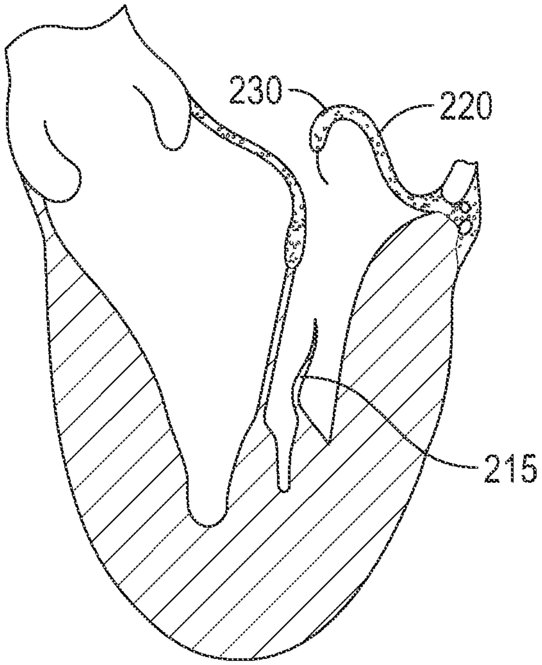
FIGS. 3A-3B illustrate a simplified cross-section of a heart, schematically showing mitral valve regurgitation during systole in the setting of mal-coaptation of the mitral valve leaflets.

Generally, mal-coaptation can result from either excessive tethering by the support structures of one or both leaflets, or from excessive stretching or tearing of the support structures. Other, less common causes include infection of the heart valve, congenital abnormalities, and trauma. Valve malfunction can result from the chordae tendinae becoming stretched, known as mitral valve prolapse, and in some cases tearing of the chordae 215 or papillary muscle, known as a flail leaflet 220, as shown in FIG. 3A. Or if the leaflet tissue itself is redundant, the valves may prolapse so that the level of coaptation occurs higher into the atrium, opening the valve higher in the atrium during ventricular systole 230. Either one of the leaflets can undergo prolapse or become flail. This condition is sometimes known as degenerative mitral valve regurgitation.

Figure 3B:
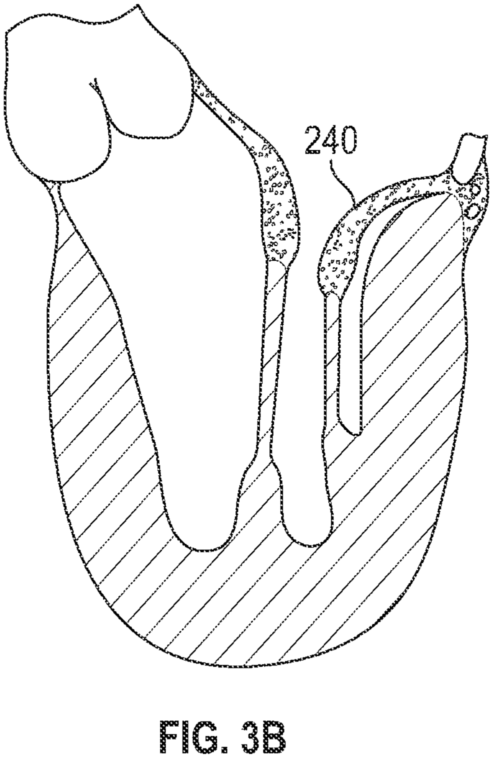

In excessive tethering, as shown in FIG. 3B, the leaflets of a normally structured valve may not function properly because of enlargement of or shape change in the valve annulus: so-called annular dilation 240. Such functional mitral regurgitation generally results from heart muscle failure and concomitant ventricular dilation. And the excessive volume load resulting from functional mitral regurgitation can itself exacerbate heart failure, ventricular and annular dilation, thus worsening mitral regurgitation.

Figure 4A:
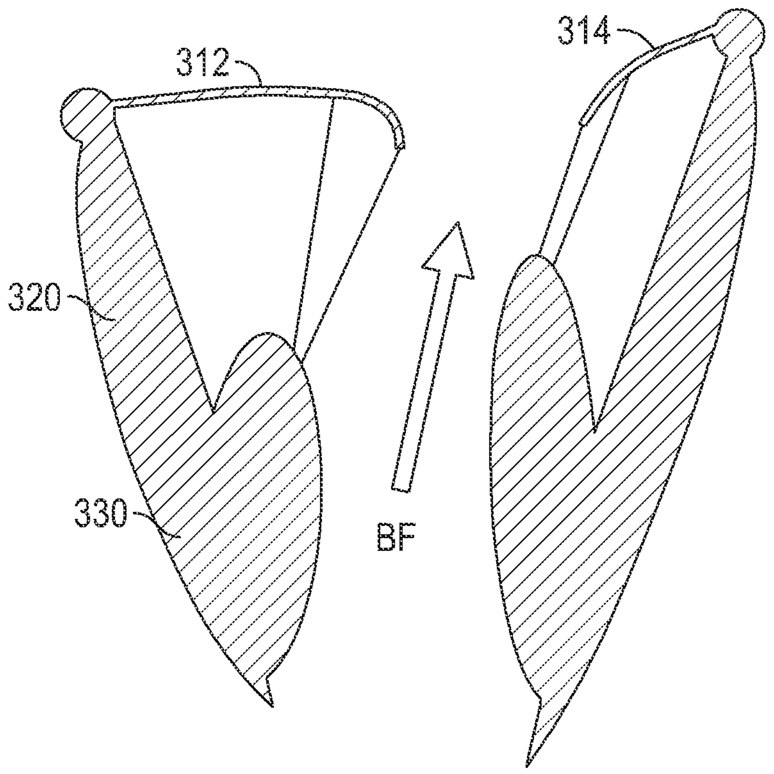
FIG. 4A illustrates a stylized cross section of a heart, showing mitral valve mal-coaptation in the settings of functional mitral valve regurgitation.
Figure 4B:
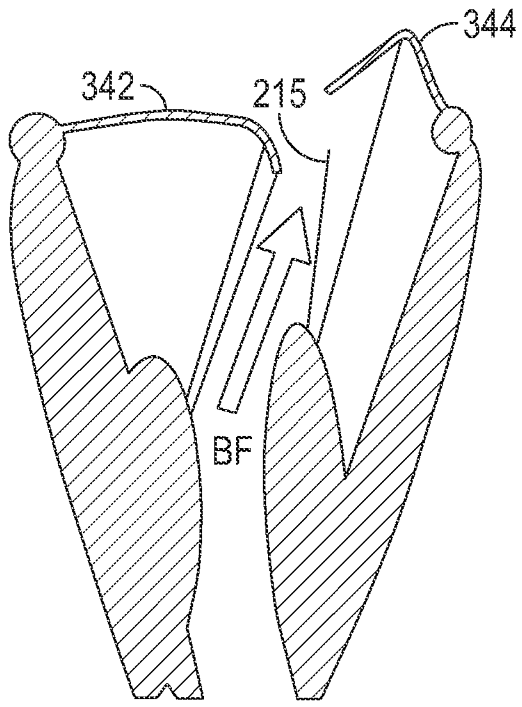
FIG. 4B illustrates a stylized cross section of a heart, showing mitral valve mal-coaptation in the settings of degenerative mitral valve regurgitation.

FIG. 4A-4B illustrate the backflow BF of blood during systole in functional mitral valve regurgitation (FIG. 4A) and degenerative mitral valve regurgitation (FIG. 4B). The increased size of the annulus in FIG. 4A, coupled with increased tethering due to hypertrophy of the ventricle 320 and papillary muscle 330, prevents the anterior leaflet 312 and posterior leaflet 314 from opposing, thereby preventing coaptation. In FIG. 4B, the tearing of the chordae 215 causes prolapse of the posterior leaflet 344 upward into the left atrium, which prevents opposition against the anterior leaflet 342. In either situation, the result is backflow of blood into the atrium, which decreases the effectiveness of left ventricle compression.

Figure 5A:
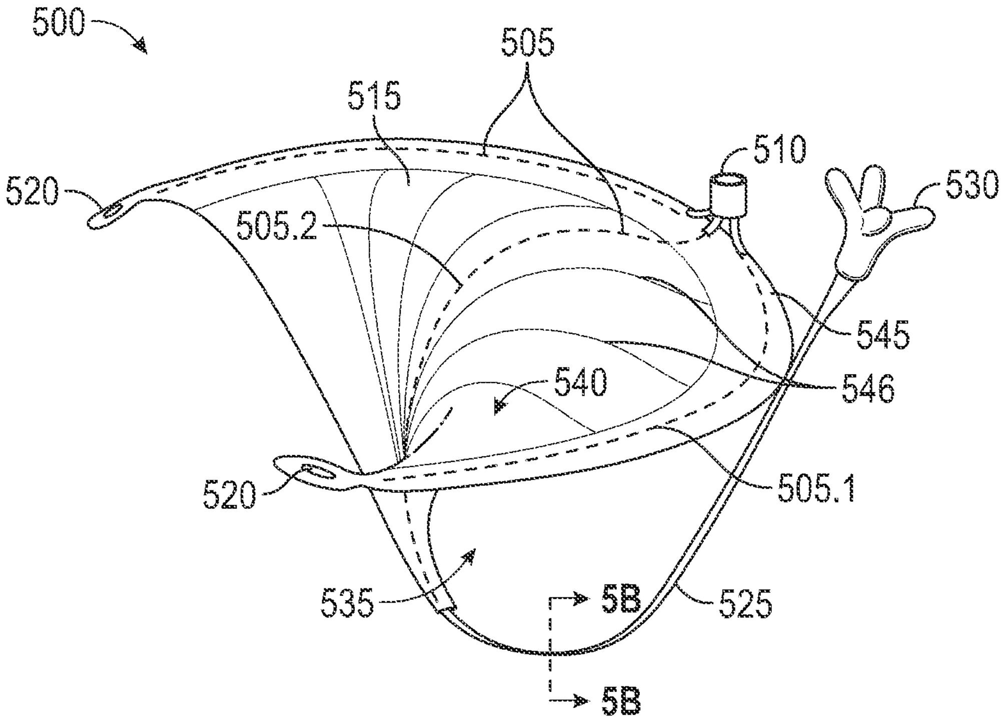
FIG. 5A illustrates an embodiment of the coaptation assistance device.

FIG. 5A illustrates an embodiment of a coaptation assistance device 500. The coaptation assistance device 500 can include a coaptation assistance body 515. The coaptation assist body 515 can include a first coaptation surface 535. The first coaptation surface 535 can be disposed toward a mal-coapting native leaflet, in the instance of a mitral valve, the posterior leaflet when implanted. The coaptation assist body 515 can include a second coaptation surface 540. The second coaptation surface 540 can be opposed to the first coaptation surface 535 as shown in FIG. 5A. The second coaptation surface 540 can be disposed toward a mal-coapting native leaflet, in the instance of a mitral valve, the anterior leaflet when implanted. The first coaptation surface 535 and the second coaptation surface 540 can be bounded by a first lateral edge and a second lateral edge. The first coaptation surface 535 and the second coaptation surface 540 can be bounded by an inferior edge and a superior edge 545.

The first coaptation surface 535 and the second coaptation surface 540 are two sides of the same implant structure forming the coaptation assistance body 515. The shape of the coaptation assistance body 515 may be characterized generally, in some embodiments, by the shape of the superior edge 545, the shape of the first coaptation surface 535, and the second coaptation surface 540.

The coaptation assistance device 500 can include a ventricular projection 525 as shown in FIG. 5A. The ventricular projection 525 can extend from the inferior edge of the coaptation assistance body 515. The ventricular projection 525 can be placed within the left ventricle when implanted. The ventricular projection 525 can provide an anchoring mechanism. The distal end 530 of the ventricular projection 525 generally provides the anchoring mechanism.

Figure 5B:
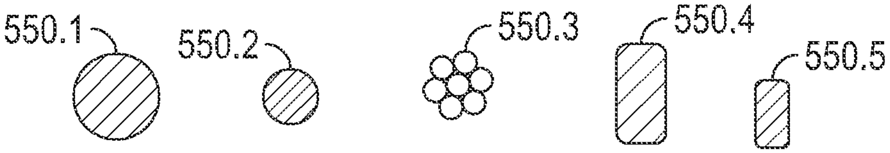
FIG. 5B illustrates the various cross-sections the support structure may have along the section A-A of FIG. 5A
Figure 5C:
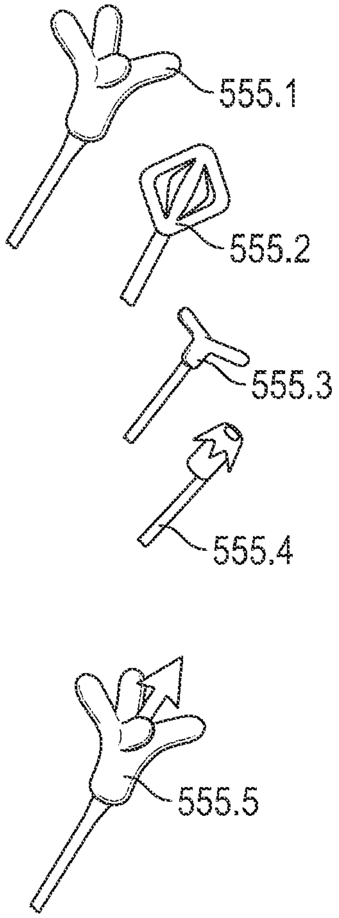
FIG. 5C illustrates the various shapes of the anchors at the distal end of the ventricular projection.

The distal end 530 of the ventricular projection 525 may have different shapes as shown in FIG. 5C. FIG. 5C shows five embodiments of the distal end 530. It is noted that more variations are possible and they are not limited to the five embodiments shown in FIG. 5C. Generally, and in other embodiments, there are two types of anchors. Examples of passive anchors are shown in embodiments 555.1 through 555.4 in FIG. 5C. Passive anchors rely on entrapment behind and/or interference with the chordae. With respect to the passive anchors, in some embodiments, the largest dimension or the dimension responsible for entanglement (usually the width) with the chordae may range from 10 mm to 40 mm, such as 25 mm.

Distal end 555.1 includes one or more prongs. The prongs can be an elongate rod which extends from a central hub as shown. In the illustrated embodiment, four prongs extend from the central hub. In other embodiments, one or more prongs extend from the central hub. The prongs can extend at an angle from the central hub, thereby increasing the surface area of the distal end 530. Distal end 555.2 can be generally rectangular, rectangular, generally square, square, generally diamond shaped or diamond shaped. The distal end 555.2 can include one or more cut outs. The cut outs can increase the ability to grip tissue. In the illustrated embodiment, four cutouts are formed in the distal end. In other embodiments, one or more cut outs are provided.

Distal end 555.3 includes one or more prongs. The prongs can be an elongate rod which extends from a central hub as shown. In the illustrated embodiment, two prongs extend from the central hub. In other embodiments, one or more prongs extend from the central hub. The prongs can extend at a right angle from the central hub, thereby increasing the surface area of the distal end 530.

Distal end 555.4 includes one or more barbs. The barbs can extends from a central hub as shown. The barbs can extend back toward the central hub. In the illustrated embodiment, three or more barbs extend from the central hub. In other embodiments, one or more barbs in one or more directions are provided.

Distal end 555.5 includes one or more prongs, and is similar to the configuration shown as distal end 555.1. Distal end 555.5 is an example of an active anchor. Active anchors may have features such as sharp points, barbs, or screws that may couple to the ventricular tissue. Active anchors may require a driving force, such as a torque, to embed within the tissue. Either passive or active anchors may be made of implant grade biocompatible materials such as silicone, PEEK, pebax, polyurethane.

Figure 5D:
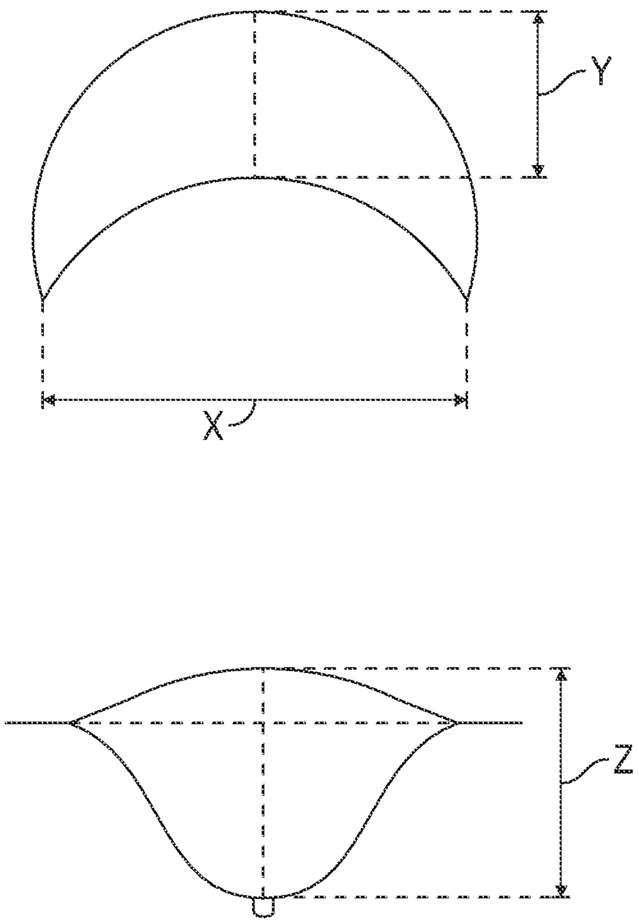
FIG. 5D illustrates non-limiting examples of ranges of dimensions of the coaptation assistance device.

The size of the coaptation assistance device 500 is described in detail in FIG. 5D. This figure shows the top view and front view of the coaptation assistance body 515 of the coaptation assistance device 500. The three parameters "x", "y" and "z" shown in the figure characterize the coaptation assistance device 500. Non-limiting examples of ranges and magnitudes of these variables x, y, and z are shown in the "Dimension Table" in the figure.

The coaptation assistance device 500 can include a support structure 505. The support structure 505 can be referred to as a spine. The support structure 505 can define, at least in part, the shape of the coaptation assistance device 500.

Returning back to FIG. 5A, the support structure 505 is shown by dotted lines. In some embodiments, the support structure 505 is made of a shape memory material such as but not limited to nitinol (NiTi), polyether ether ketone (PEEK) or other stiff polymer or fatigue resistant metal. The use of shape memory materials enables advantages described herein. For example, one advantage of a shape memory material is that its superelastic properties helps the coaptation assistance device 500 maintain its shape and functionality as a coaptation assistance device as the heart contracts and dilates and exerts pressure on the coaptation assistance device 500. Another example of an advantage is that a shape memory material lends itself to percutaneous delivery methods which will be described herein.

The support structure 505 can include one or more section. In some embodiments, the support structure 505 includes one section. In some embodiments, the support structure 505 includes two sections. In some embodiments, the support structure 505 includes three or more sections. In some embodiments, one or more sections of the support structure 505 can include one or more subsection. In the embodiment shown in FIG. 5A, the support structure 505 includes two sections: a first section 505.2 and a second section 505.1.

The first section 505.2 can extend through at least a portion of the coaptation assistance device 500 between the superior edge 545 and the ventricular projection 525. In some embodiments, the first section 505.2 can extend through the entire length between of the coaptation assistance device 500 between the superior edge 545 and the ventricular projection 525. In some embodiments, the first section 505.2 extends from a location between the superior edge 545 and the inferior edge of the coaptation assistance body 515. In some embodiments, the first section 505.2 extends from a location between the inferior edge of the coaptation assistance body 515 and the ventricular projection 525. In some embodiment, the first section 505.2 extends along the coaptation assistance body 515 and continues on to support the ventricular projection 525.

The second section 505.1 can extend through at least a portion of the coaptation assist body 515 between the first lateral edge and the second lateral edge. In some embodiments, the second section 505.1 can extend through the entire length between of the first lateral edge and the second lateral edge. In some embodiments, the second section 505.1 extends from a location between the superior edge 545 and the inferior edge of the coaptation assistance body 515. In some embodiments, the second section 505.1 extends from a location closer to the superior edge 545 than the inferior edge of the coaptation assistance body 515. In some embodiments, the second section 505.1 extends from the first lateral edge toward the second lateral edge. In some embodiments, the second section 505.1 extends from the second lateral edge toward the first lateral edge. In some embodiments, the second section 505.1 extends along a section between the first lateral edge and the second lateral edge. In some embodiments, the second section 505.1 extends along the edge of the coaptation assistance device 500.

In some embodiments, the first section 505.2 and the second section 505.1 of the support structure 505 may be one integral piece or unitary structure. In some embodiments, the first section 505.2 and the second section 505.1 of the support structure 505 are separate components. In some embodiments, the first section 505.2 and the second section 505.1 may be two separate sections joined together by methods such as but not limited to crimping and laser welding.

In some embodiments, the first section 505.2 is integrated within the coaptation assistance body 515 as described herein. In some embodiments, the first section 505.2 in integrated within the ventricular projection 525 as described herein. In some embodiments, the first section 505.2 is removable from the coaptation assistance body 515 as described herein. In some embodiments, the first section 505.2 is removable from the ventricular projection 525 as described herein. In some embodiments, the second section 505.1 is integrated within the coaptation assistance body 515 as described herein. In some embodiments, the second section 505.1 is removable from the coaptation assistance body 515 as described herein. In some embodiments, the first section 505.2 can have a first zone that is generally oriented substantially parallel to a longitudinal axis of the body 515, and a second zone that is generally oriented substantially perpendicular to the longitudinal axis of the body 515 as illustrated.

The support structure 505 that supports the shape of the ventricular projection 525 may have various cross sections as shown by section AA in FIG. 5A and illustrated in detail in FIG. 5B. In FIG. 5B, five embodiments of the cross-section are shown; however, it is noted that the embodiments of the cross section of the support structure 505 are not limited to these five. Cross-section 550.1 is circular or generally circular. Cross-section 505.2 is circular or generally circular. Cross-section 550.1 can have a larger cross-sectional area than cross-section 550.2. Cross-section 550.3 comprises a plurality of circular or generally circular cross-sections. In the illustrated embodiment, seven circular or generally circular cross-sections collectively form the cross-section 550.3. In other embodiments, two or more circular or generally circular cross-sections collectively form the cross-section 550.3. Cross-section 550.3 can be in the form of a cable. Cross-section 550.4 is rectangular or generally rectangular. Cross-section 550.5 is rectangular or generally rectangular. Cross-section 550.4 can have a larger cross-sectional area than cross-section 550.5.

It is also noted that the first section 505.2 and the second section 505.1 may have different cross-sections as well. Each cross-section or embodiment shown in FIG. 5B may have certain advantages such as some cross sections may bend easily in one direction and not in another. Some other cross sections may have higher reliability properties than others. The characteristics of each type of cross-section is described along with the ranges and non-limiting possible dimensions of the cross section in Table 2 in FIG. 5E for two different materials nitinol and PEEK. Although various configurations are presented in Table 2, in some embodiments, cross-sections 550.4 and 550.5 can be utilized for both materials.

Figure 5F:
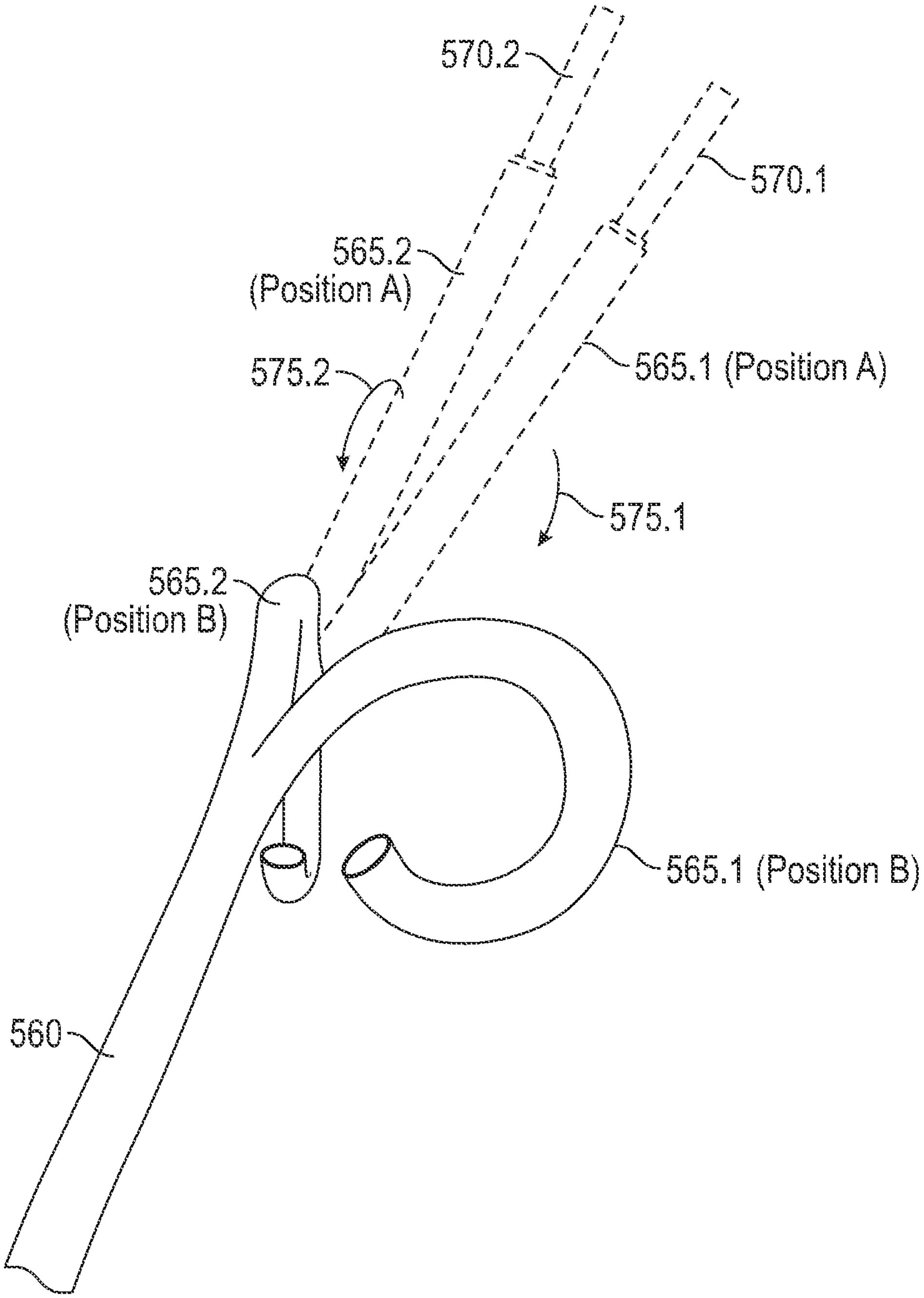
FIG. 5F illustrates an embodiment of the distal end of the ventricular projection.
Figure 5G:
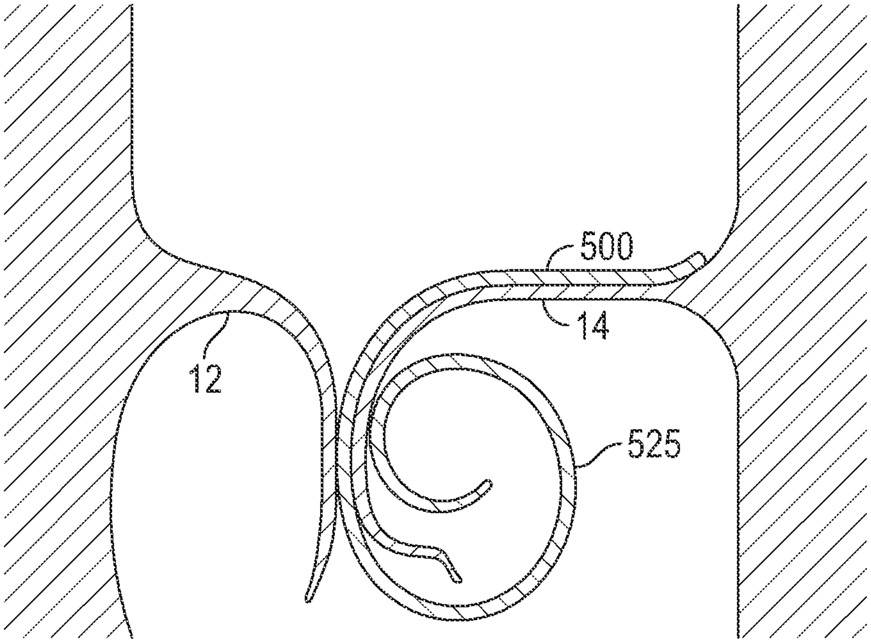
FIG. 5G illustrates the position of the coaptation assistance device may be maintained by utilizing the shape of the coaptation assistance device to pinch the native posterior leaflet.

When the coaptation assistance device 500 is placed within the heart, the coaptation assistance device 500 is such that, in some embodiments, the ventricular projection 525 will generally be placed within the left ventricle as shown in FIG. 5G. The ventricular projection 525 provides a mechanism to anchor the coaptation assistance device 500 using the structure of the ventricles. An example of positioning of the coaptation assistance device 500 over the posterior leaflet is illustrated in FIG. 5G.

Bearing in mind that other examples of positioning are possible and are discussed elsewhere within this disclosure, in this particular example, the coaptation assistance device 500 is illustrated with a ventricular projection 525 that has a curved shape. The ventricular projection 525 and/or the first support 505.2 may be composed of shape memory materials, in which case the curved shape is retained after implantation. The curved shape may enable the coaptation assistance device 500 to stay in position as engages to the native posterior leaflet 14.

FIG. 5F shows an embodiment of a passive anchor for the ventricular projection 525. In this embodiment, a tube 560 running along the length of the ventricular projection 525 terminates in two tubes 565.1 and 565.2, at the distal end of the coaptation assistance device 500. The coaptation assistance device 500 may be delivered to the left side of the heart with straightening wires such that the two tubes 565.1 and 565.2 are approximately straight as shown by the dotted lines 565.1 and 565.2 (Position A) indicating that the straightening wires are in an advanced state. In some embodiments, the two tubes 565.1 and 565.2 may be made of shape memory material including but not limited to polyurethane, silicone, polyethylene, pebax and nylon. Without the straightening wires, the two tubes 565.1 and 565.2 may have a default shape that may be curled or coiled as shown by the solid lines 565.1 and 565.2 (Position B) in FIG. 5F.

After the implant is appropriately delivered and placed in the heart, the straightening wires may be withdrawn allowing the two tubes 565.1 and 565.2 to assume their default shape (Position B). The two tubes 565.1 and 565.2 may provide anchoring support due to entanglement with the chordae. The advantage of this type of anchoring is that the straightening wires may be advanced back into the two tubes 565.1 and 565.2, straightening out the two tubes 565.1 and 565.2 and causing the two tubes 565.1 and 565.2 to disentangle from the chordae structure should it become necessary to reposition the coaptation assistance device 500 due to unsatisfactory placement. Although the example above describes two tubes 565.1 and 565.2, it will be understood that there may be one, two, or more tubes.

Figure 5H:
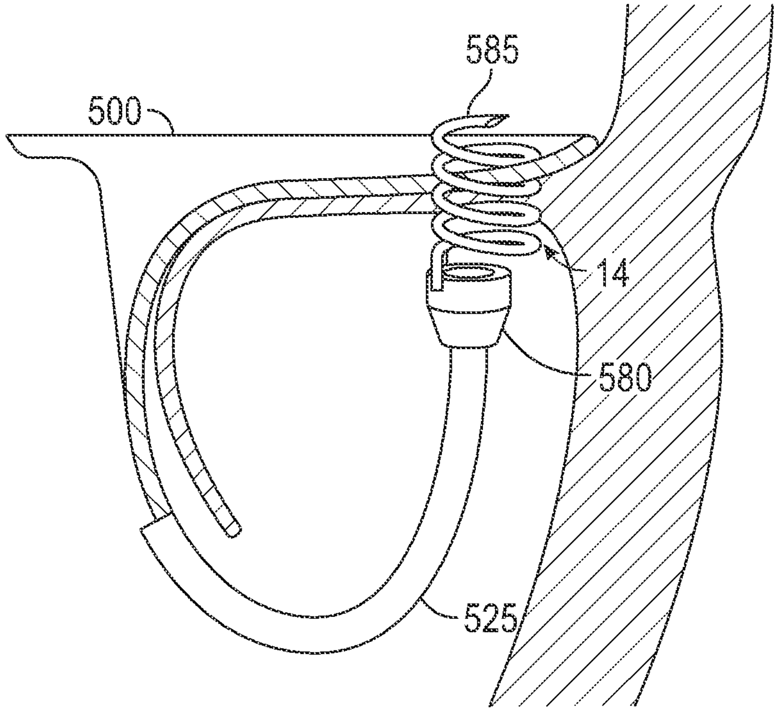
FIG. 5H illustrates an embodiment of how the coaptation assistance device may be secured through the posterior leaflet from the ventricular side.

Yet another embodiment of anchoring the coaptation assistance device 500 is illustrated in FIG. 5H. An active anchor may be coupled to the distal end of the ventricular projection 525. After delivery of the implant, the active anchor may be driven through the posterior leaflet to couple to the coaptation assistance device 500 at the annular (atrial) section as shown. Methods to position and drive the anchors will be discussed herein.

In another embodiment, the tips of the ventricular projection 525 may be radiopaque or echogenic to aid in placement and anchoring of the coaptation assistance device 500 while the coaptation assistance device 500 is being placed percutaneously. In such a procedure, fluoroscopic or ultrasound imaging modalities may be used to visualize the heart and the coaptation assistance device 500.

Returning back to FIG. 5A, in another embodiment, the coaptation assistance device 500 can include a hub 510. The hub 510 can have one or more purposes. One purpose can be to serve as an anchoring device as discussed herein. Another purpose can be to provide a mechanism to deliver the coaptation assistance device 500 percutaneously as discussed herein. In some embodiments, a hub (not shown) may be present at the distal end of the coaptation assistance device 500. The hub can be located at the end of the ventricular projection 525. The ventricular hub may be placed at the very distal tip of the distal end 530 of the ventricular projection 525. To distinguish the two hubs, the hub 510 on the proximal side will be called simply the "hub", the "annular hub" or the "proximal hub". The hub at the distal tip of the ventricular projection will specifically be called the "ventricular hub".

Still referring to FIG. 5A, the coaptation assistance body 515 of the coaptation assistance device 500 may be made of various biocompatible materials such as expanded polytetrafluoroethylene (ePTFE). This material provides the coaptation surface against which the anterior leaflet will close. The coaptation assistance body 515 of the coaptation assistance device 500 can be coupled to the support structure 505 such that the shape of the support structure 505 gives the general shape of the coaptation assistance device 500.

The shape of the coaptation assistance device 500 may be further supported by one or more ribs 546 (not shown). There may be one, two, or more ribs 546. The ribs 546 may be made of various materials such as but not limited to suture, polypropylene, nylon, NiTi cable, NiTi wire and PEEK. The process of coupling the coaptation assistance body 515 of the coaptation assistance device 500 to the support structure 505 and/or the ribs 546 (if ribs 546 are present) is described herein.

In some methods of manufacturing, the process may commence by slipping polyethylene (PE) tubes on the support structure 505 and/or the ribs 546 (if ribs 546 are present). This combination is placed between two ePTFE sheets after which heat and pressure are applied. The ePTFE bonds with the PE tubes due to pores in the ePTFE material into which the polyethylene material of the tube may melt into, creating a mechanical bond. Similarly, the PE tube material may melt into microholes in the support structure 505 and/or the ribs 546 when heat and compression are applied. The microholes in the support structure 505 and/or the ribs 546 may be deliberately placed to improve the bonding.

In a variation of the process described above, PE sheets may be placed where no PE tubes may be present. In this variation, just as described above, a similar process of heat and compression is applied and a more uniform composite structure may be generated. In a further embodiment, the support structure 505 and/or the ribs 546 may have features such as microholes that couple the ePTFE membrane. The micro-hole diameters may be in the range of 0.005" to 0.030", for example.

In a variation on the type of materials that may be used to make the coaptation assistance body 515 of the coaptation assistance device 500, other materials such as but not limited to sponge material, polyurethane, silicone, bovine or porcine pericardium may be utilized. Bonding processes may include but may not be limited to heat bonding, suturing and gluing.

Continuing to refer to FIG. 5A, in some embodiments, the coaptation assistance device 500 has perforations or slots 520. There may be one or multiple such perforations or slots 520. These perforations 520 can serve the purpose of providing sites where anchors may be placed as discussed herein.

One of the advantages of the coaptation assistance device 500 is that the coaptation assistance device 500 may be folded into a smaller structure. The coaptation assistance device 500 can be delivered percutaneously through a delivery catheter. In some embodiments, the support structure 505 is made of a shape memory material. When the coaptation assistance device 500 is unfolded inside the heart, the desired shape of the coaptation assistance device 500 is regained. Many embodiments now describe the various methods, devices and systems that are used to deliver the coaptation assistance device 500 into the heart.

In some methods of use, the first support has a first configuration wherein the first support 505.2 is generally linear and a second configuration wherein the first support 505.2 is curved. In some methods of use, the first support 505.2 and the second support 505.1 are configured to permit percutaneous insertion of the coaptation assistance device 500.

The first few steps in the delivery procedure can be similar to those that are known in the art. The body of the patient is punctured for example in the lower torso/upper thigh area (groin) to get access to the femoral vein. Generally a trans-septal sheath and needle are inserted into the inferior vena cava and advanced up to the atrial septum, at which point a trans-septal puncture is performed and the trans-septal sheath is advanced into the left atrium. The needle is removed and the trans-septal sheath now provides access to the left atrium. More details about the above steps may be found in publicly available medical literature.

The method can include various steps including those that are now described. The ventricular projection 525 of the coaptation assistance device 500 can be generally be placed within the left ventricle. It may be advantageous to guide the coaptation assistance device 500 to this location using various guiding techniques. For example a simple guidewire may be placed inside the trans-septal sheath and guided into the left ventricle by first entering the left atrium and going through the mitral valve. However, simple guidewire may not provide sufficient accuracy in placement of the ventricular projection 525.

In some embodiments, a method of placing a guidewire inside a steerable sheath may be used. The steerable sheath with a guidewire may be advanced through the trans-septal sheath and subsequently advanced through the mitral valve into the left ventricle where the steering ability of the steerable sheath would give additional support to position the guidewire appropriately. After the guidewire is placed, the steerable sheath requires to be removed prior to delivery of the coaptation assistance device. This method, although providing a more accurate positioning of the guidewire, involves an extra step of removing the steerable sheath. To improve on this process in terms of reducing the number of steps needed to perform the implantation, a various embodiments of a steerable sheath are disclosed herein.

Small Diameter Steerable Catheter

Figure 6A:
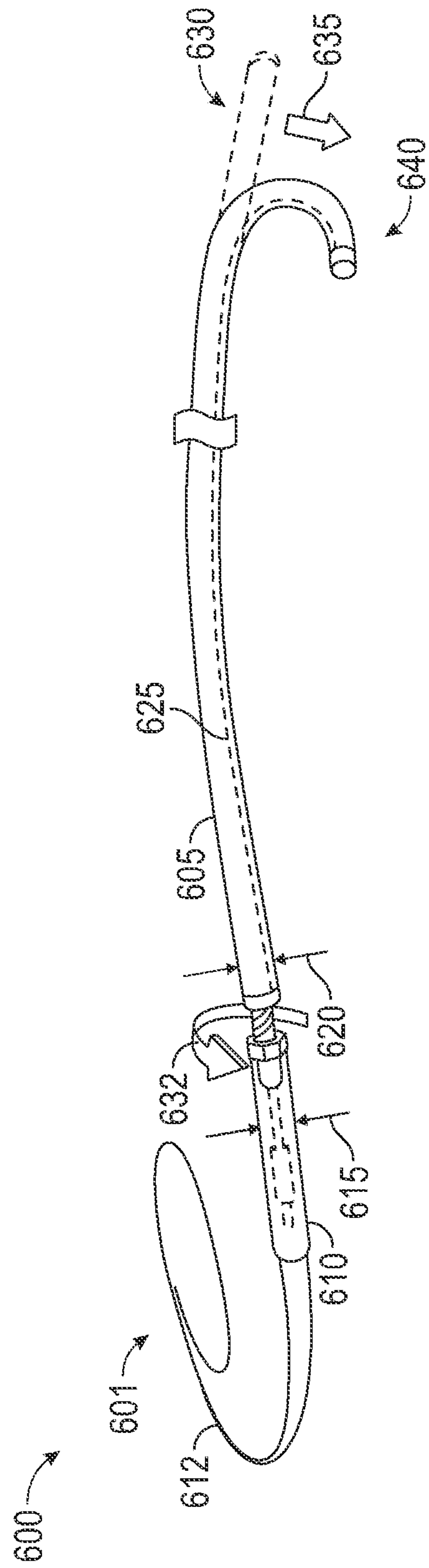
FIG. 6A illustrates a steerable catheter.

Referring to FIG. 6A, a small diameter steerable catheter 600 is illustrated. In some embodiments, the diameter 615 of a handle 610 of the steerable catheter 600 can be equal or substantially equal to the diameter 620 of the body 605 of the steerable catheter 600. The steerable catheter 600 can have within it a pullwire 625. When the handle 610 is rotated, for example in the direction of the arrow 632, the distal portion of the steerable catheter 600 moves along arrow 635 from the linear position 630 to the curved position 640. The curved position 640 may be beneficial to position the ventricular projection 625 as discussed herein. When the handle 610 is rotated, for example in the opposite direction of the arrow 632, the distal portion of the steerable catheter 600 moves along from the curved position 640 to the linear position 630. The linear position 630 of the steerable catheter 600 is shown by dotted lines, not to be confused with the pullwire 625 which is also shown in dotted lines. The linear position 630 may be beneficial for insertion or retraction of the steerable catheter 600 from the anatomy.

In some embodiments, the diameter of the handle 610 can be equal to the diameter of the body 605. This can be advantageous as the coaptation assistance device 500 may slide over the handle 610 and/or the body 605 smoothly after the steerable catheter 600 is placed in the ventricle. In some embodiments, the steerable catheter 600 can include an extension 612 at the proximal end which extends from the handle 610. The extension 612 can be a wire or other elongate structure. The purpose of the extension 612 is to aid in the loading of other catheters or devices while allowing a physician or other operators to retain control of the steerable catheter 600. Subsequent to loading of the other catheters or devices on the extension 612, the steerable catheter 600 is utilized to guide the other catheters or devices. The length of the extension 612 can match or exceed the length of the catheter or device that is being loaded such that during the process of loading and delivering the other catheter or device, control of the steerable catheter 600 is retained.

In some embodiments, the extension 612 may be coupled to the handle 610 only when necessary. For example if during a procedure, the medical team decides that a longer catheter is necessary, the extension 612 may be coupled to the handle 610. Coupling mechanisms may include but are not limited to a threaded junction, a compression fit, or other mechanisms.

Non-limiting examples of dimensions of the various subcomponents in some embodiments (the body 605, handle 615, extension 612) can be as follows: the diameter 620 of the body 605 may range from 2 to 10 Fr, such as 4 Fr, between about 2 Fr and about 6 Fr, between about 3 Fr and about 5 Fr, or less than 10 Fr, 9 Fr, 8 Fr, 7 Fr, 6 Fr, 5 Fr, 4 Fr, 3 Fr, or 2 Fr. The handle 610 length may range in some cases from about ½" to about 2", such as about 1", the handle linear travel (for pullwire activation) may range in some cases from about ⅛" to about 3", such as about ¼".

During the implantation process, some methods involve the guidewire or guidewire and steerable sheath. In some methods, the steerable catheter 600 may be advanced through the femoral access. Since the handle 610 is outside the patient's body, it may be rotated such that the distal portion of this steerable catheter 600 is placed in an appropriate position under the posterior leaflet. The extension 612 can be attached to the proximal end of the handle 610 to allow subsequent loading of the coaptation assistance device 500 and delivery catheter 700 prior to insertion into the trans-septal sheath 650, described herein. This delivery catheter 700 may then be used as a guide for introducing the coaptation assistance device 500 as will be explained herein.

Figure 6B:
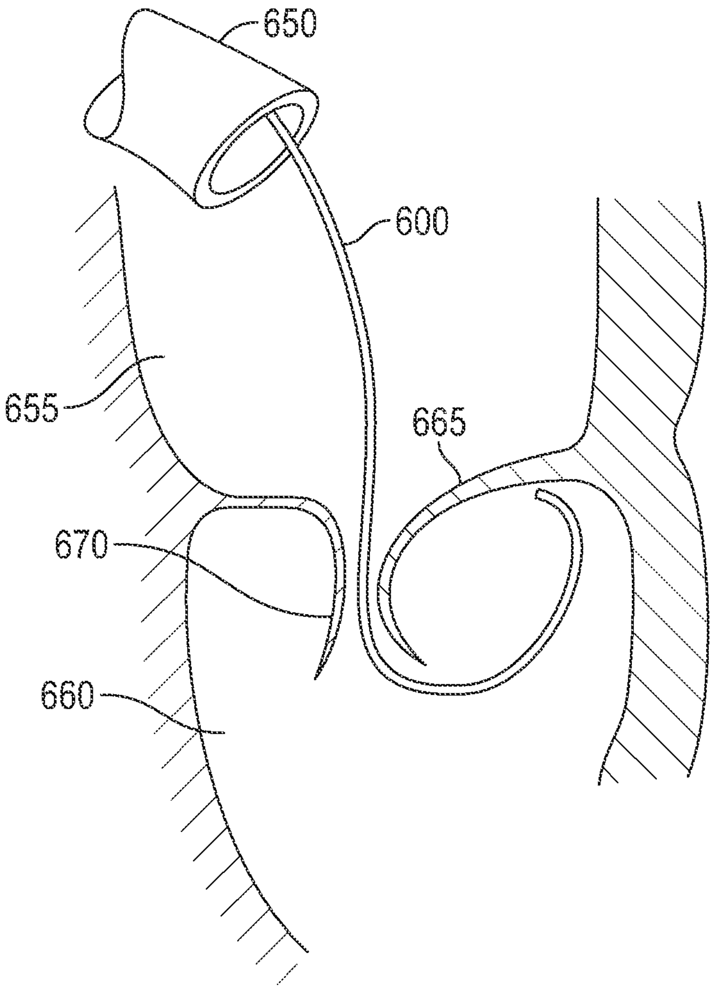
FIG. 6B illustrates the position of the steerable catheter of FIG. 6A in the heart.

FIG. 6B illustrates the placement of the steerable catheter 600 in the heart. An embodiment of the trans-septal sheath 650 is shown. The left atrium 655, left ventricle 660, the posterior leaflet 665 of the mitral valve and the anterior leaflet 670 of the mitral valve are also shown. The steerable catheter 600 is shown going through the mitral valve and being positioned under the posterior leaflet 665. It may be now appreciated how having the ability to deflect the distal portion of steerable catheter 600 can be advantageous so that an appropriate position of the coaptation assistance device 500 may be achieved. The distal portion of the steerable catheter 600 is able to curve under the posterior leaflet 665 as shown. In some methods, the next general step after placing the steerable catheter 600 is to deliver the coaptation assistance device 500 to the heart. Further embodiments are now described with regards to methods and devices to achieve delivery.

Delivery Catheter

Figure 7A:
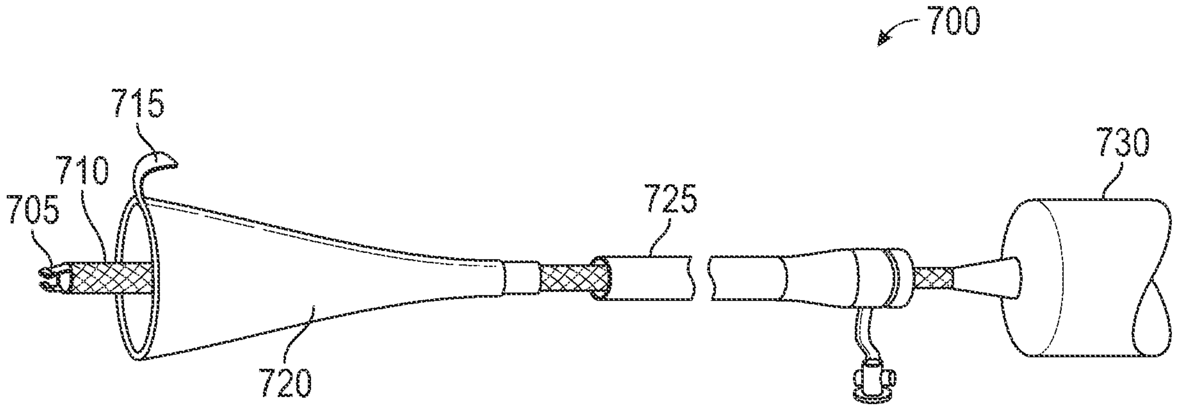
FIG. 7A illustrates a delivery catheter.

Referring to FIG. 7A, a delivery catheter 700 is now described. The function of the delivery catheter 700 is to carry the coaptation assistance device 500 to the heart. The shaft body 710 of the delivery catheter 700 can be torqueable and deflectable. The shaft body 710 is shown by the cross hatched lines. The delivery catheter 700 can include a handle 730. The handle 730 can have rotation mechanisms, for example pull wires etc. The rotation mechanism can deflect and steer the shaft body 710. Distal to the handle 730 is an implant sheath 725 which as explained herein may carry the coaptation assistance device 500 to the heart. In some embodiments, and even more distal to the implant sheath 725 is a tear away funnel 720. The tear away funnel 720 can facilitate the folding of the coaptation assistance device 500. In some embodiments, the most distal end of the shaft body 710 has features that may lock the shaft body 710 to the coaptation assistance device 500 so that the coaptation assistance device 500 may be transported to the heart and placed appropriately. The locking process and features are now described in relation to FIGS. 7B, 7C and 7D.

Figure 7B:
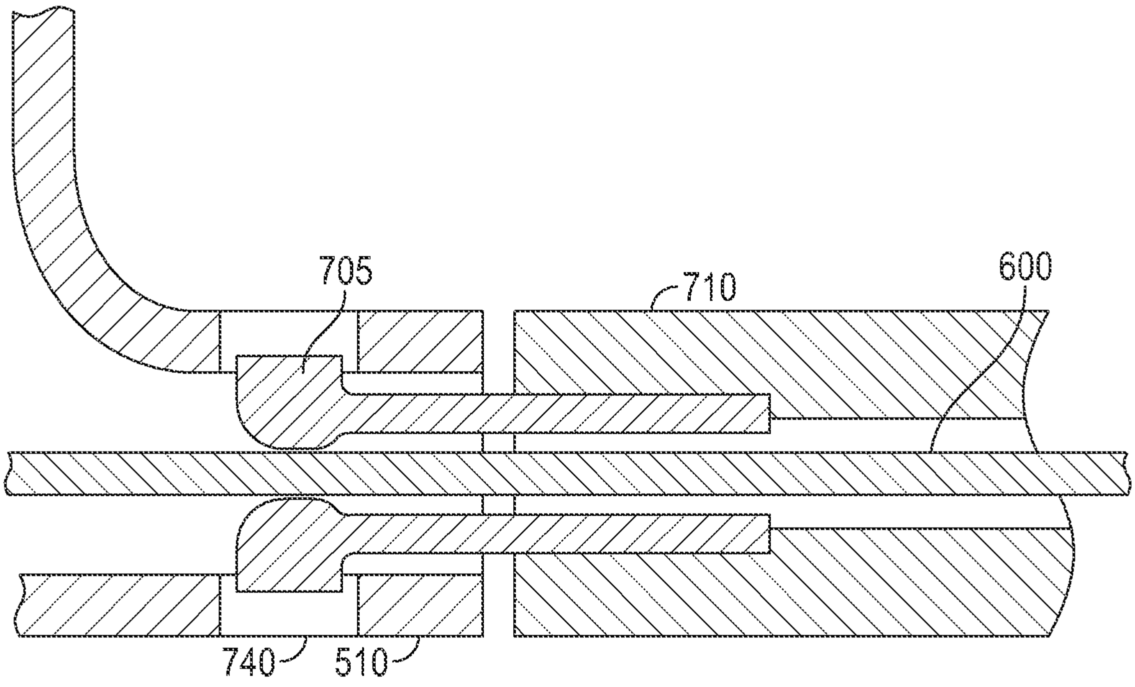
FIG. 7B illustrates an embodiment of a locking mechanism that locks the delivery catheter to the annular hub.
Figure 7C:
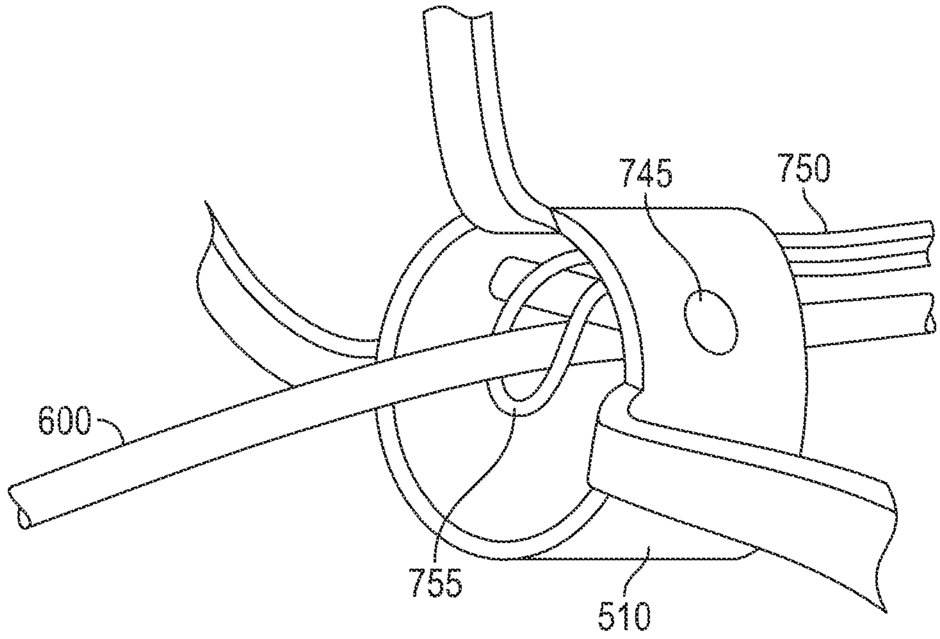
FIG. 7C illustrates another embodiment of a locking mechanism that locks the delivery catheter to the annular hub.
Figure 7D:
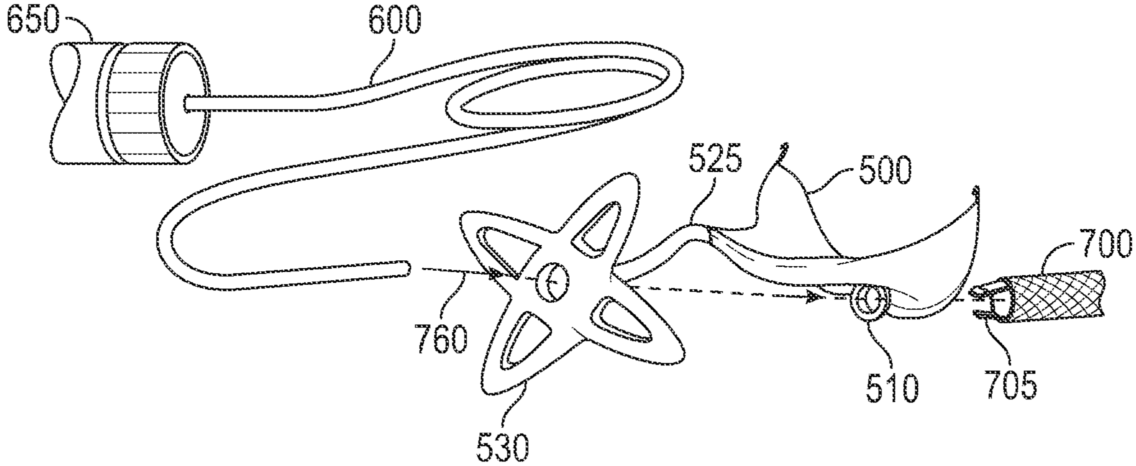
FIG. 7D illustrates the coupling of the coaptation assistance device, the delivery catheter, and a guidewire or steerable catheter.

Referring to FIG. 7D, the delivery catheter 700 and the coaptation assistance device 500 can have matching features that enable them to be locked temporarily. In some embodiments, the delivery catheter 700 includes one or more distal locking tabs 705. The coaptation assistance device 500 can include the annular hub 510 as described herein. The distal locking tabs 705 of the delivery catheter 700 may couple with features in the annular hub 510 of the coaptation assistance device 500 as will be explained herein.

In some methods, the steerable catheter 600 or other guiding wires or catheters may be advanced through the ventricular projection 525 and/or anchoring mechanism 530. In some embodiment, the anchoring mechanism 530 can have a hole or passageway in the center to allow the steerable catheter 600 to pass through, as shown in FIG. 7D. The steerable catheter 600 can pass from the anchoring mechanism 530 to the annular hub 510. Other paths through the coaptation assistance device 500 are contemplated. The steerable catheter 600 can pass from the anchoring mechanism 530 to the annular hub 510 and further to the delivery catheter 700.

Referring to FIG. 7B, the tip of the delivery catheter 700 is shown in a magnified view. The annular hub 510 of coaptation assistance device 500 is also shown. Distal locking tabs 705 may be made of some shape memory material such as nitinol. The natural position of the locking tabs 705 is set such that they bend inwards and towards each other as illustrated in FIG. 7A. In some methods, a guidewire or a catheter such as steerable catheter 600 can be inserted into the annular hub 510 and between the distal locking tabs 705, and the distal locking tabs 705 can be pushed out against the annular hub 510. The annular hub 510 is designed with matching pockets 740 such that the distal locking tabs 705 fit into these pockets 740. As long as the steerable catheter 600 is present to force the distal locking tabs 705 outwards into the pockets 740, the tip of the delivery catheter 700 remains locked to the annular hub 510. Other locking mechanisms are possible and one such alternative is now described in FIG. 7C.

Referring to FIG. 7C, the annular hub 510 can include a cross-pin 745. The cross-pin 745 can be a solid piece that goes across the annular hub 510 and is held in place by methods that are known in the art. The delivery catheter 700 can include a loop of wire or suture 750. The suture 750 which may loop around an object such as a guidewire or the steerable catheter 600 within the annular hub 510. The suture 750 may extend into the handle 730 of the delivery catheter 700. The handle 730 may have a mechanism which controls the tension of the suture 750. By controlling the tension, the coaptation assistance device 500 can be pulled against and held securely to the distal end of the delivery catheter 700. When steerable catheter 600 is retracted past the level of the cross-pin 745, the loop 755 of the suture 750 can slip over the cross-pin 745, thereby releasing the cross-pin 745 and the coaptation assistance device 500.

Delivery Procedure

Figure 8A:
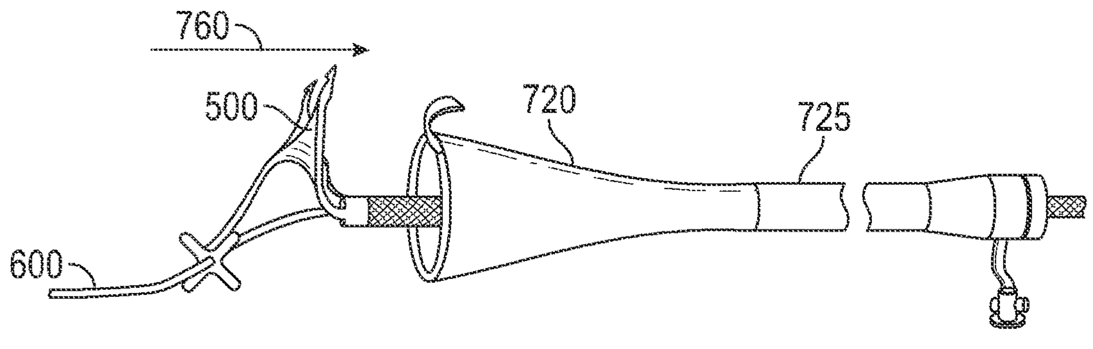
FIG. 8A-8D illustrate how the coaptation assistance device is folded and pulled into an implant sheath and delivered into the heart through the femoral access.
Figure 8B:
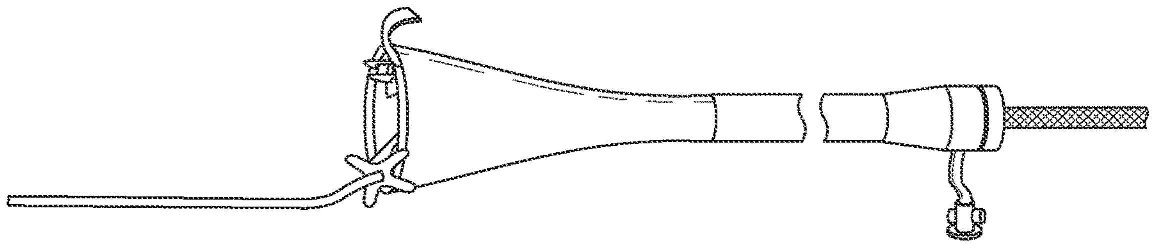
Figure 8C:
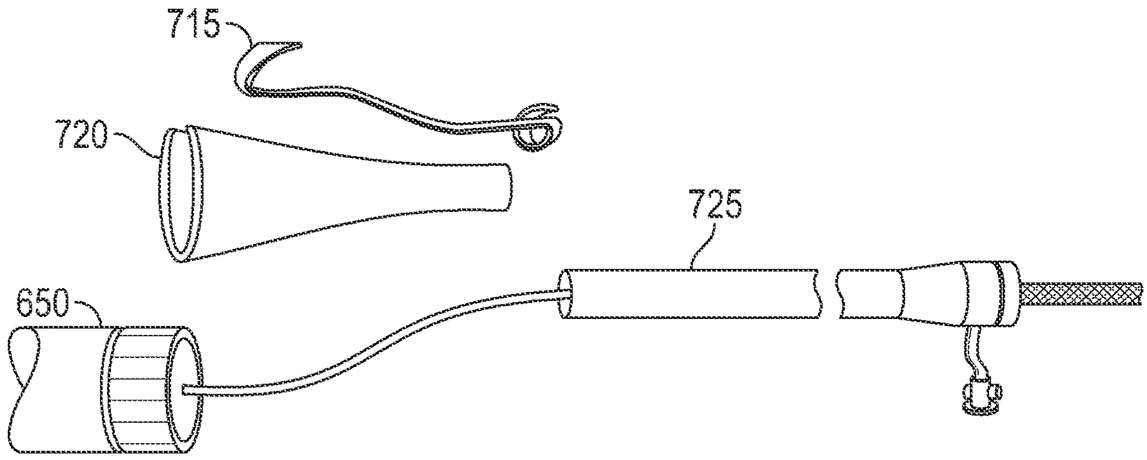
Figure 8D:
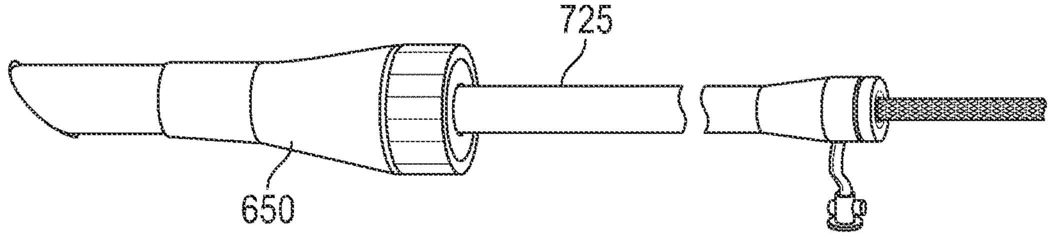

FIGS. 8A-8D show a method of delivery. In some methods, the implant sheath 725 and the funnel 720 are advanced over the coaptation assistance device 500. The implant sheath 725 and the funnel 720 can be advanced over the coaptation assistance device 500 after the delivery catheter 700 is locked with the coaptation assistance device 500. The shape of the funnel 720 aids in the coaptation assistance device 500 closing or folding in on itself. The advancement of the implant sheath 725 and the funnel 720 is shown in FIGS. 8A and 8B. The arrow 760 in FIG. 8A indicates how the coaptation assistance device 500 is pulled into the funnel 720. Once the coaptation assistance device 500 is within the implant sheath 725, the funnel 720 is removed. In some embodiments, the funnel 720 is removed by pulling on a tab 715, thereby splitting the funnel 720, shown in FIG. 8C. The funnel 720 and the tab 715 can be then discarded. In some methods, the implant sheath 725 containing the coaptation assistance device 500 can be advanced over the guidewire or the steerable catheter 600. To reiterate, the advantage of the design of the steerable catheter 600 becomes evident as the coaptation assistance device 500 can glide smoothly over the steerable catheter without having any difficulty due to different size diameters of the handle 610 and the body 605. The implant sheath 725 can be inserted into the trans-septal sheath 650 as shown FIG. 8D.

Figure 8E:
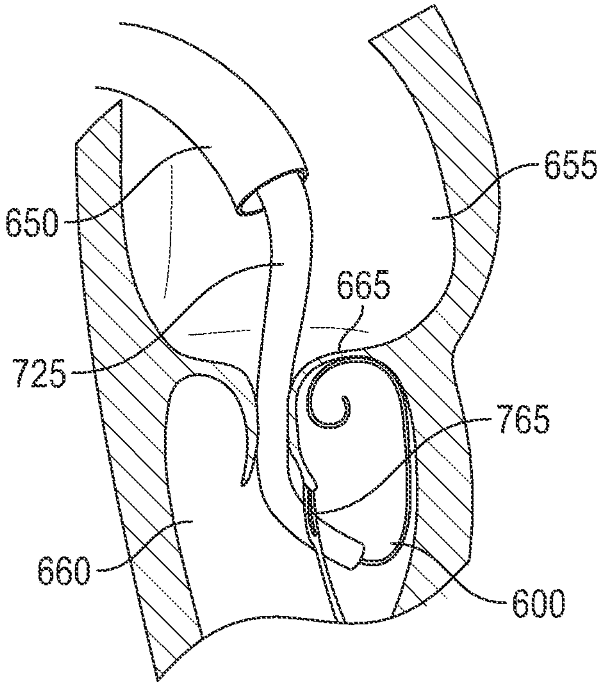
FIG. 8E-8G illustrate how the delivery catheter and the implant sheath are placed so that the ventricular projection of the coaptation assistance device may be anchored.
Figure 8F:
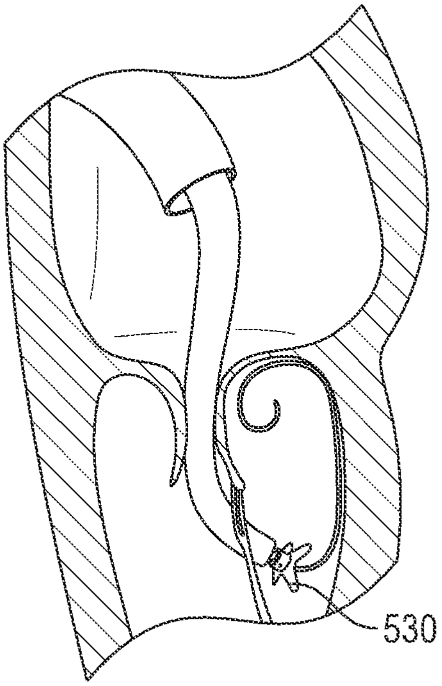
Figure 8G:
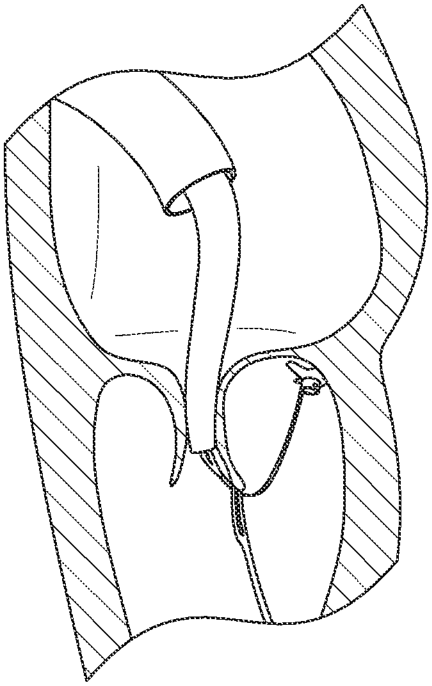

The system of the coaptation assistance device 500 and the implant sheath 725 is advanced until it exits the trans-septal sheath 650 as shown in FIG. 8E. The delivery catheter 700 is deflected such that the implant sheath 725 is positioned between the leaflets of the mitral valve, which is shown in FIG. 8E. The implant sheath 725 is placed between the chordae 765 ("P2" location). Once the implant sheath 725 attains this position, the delivery catheter 700 is held in place and the implant sheath 725 is retracted slowly, causing the coaptation assistance device 500 to start exiting the implant sheath 725 as illustrated in FIG. 8F. It is to be noted that the steerable catheter 600 or an equivalent guide wire is still in place under the posterior leaflet and can still be actively adjusted or deflected using the control handle 610. In some methods, as the delivery catheter 700 is advanced, the coaptation assistance device 500 is pushed out, following the path of the steerable catheter 600 until the distal end 530 of the ventricular projection 525 is coupled to the ventricular tissue. This is illustrated in FIG. 8G. While the coaptation assistance device 500 is being pushed out, the implant sheath 725 can be retracted. In some methods, rotational adjustments may be made to the delivery catheter 700 to ensure appropriate placement.

Anchoring

Once the coaptation assistance device 500 is open, the method can include the step of anchoring the coaptation assistance device 500 on the atrial aspect of the mitral valve namely, on the on the mitral valve annulus. Several embodiments now describe the methods and systems to achieve anchoring.

Figure 8H:
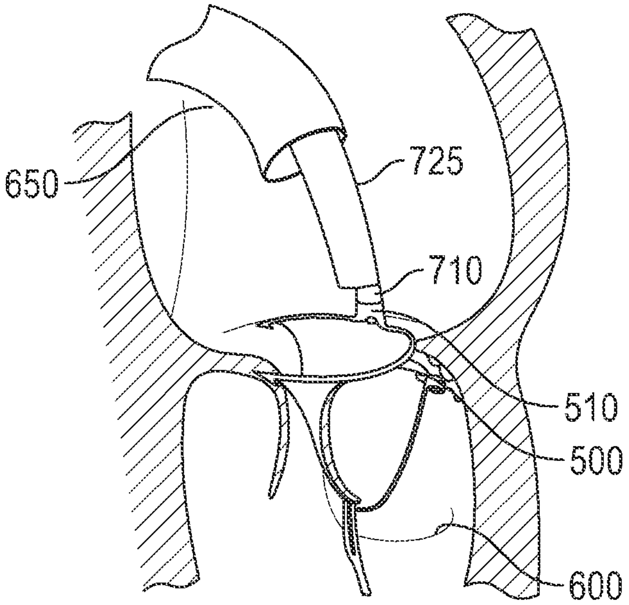
FIG. 8H illustrates the coaptation assistance device that is fully open and the delivery catheter positioned over the annular hub for anchoring the annular hub to the annulus.
Figure 8I:
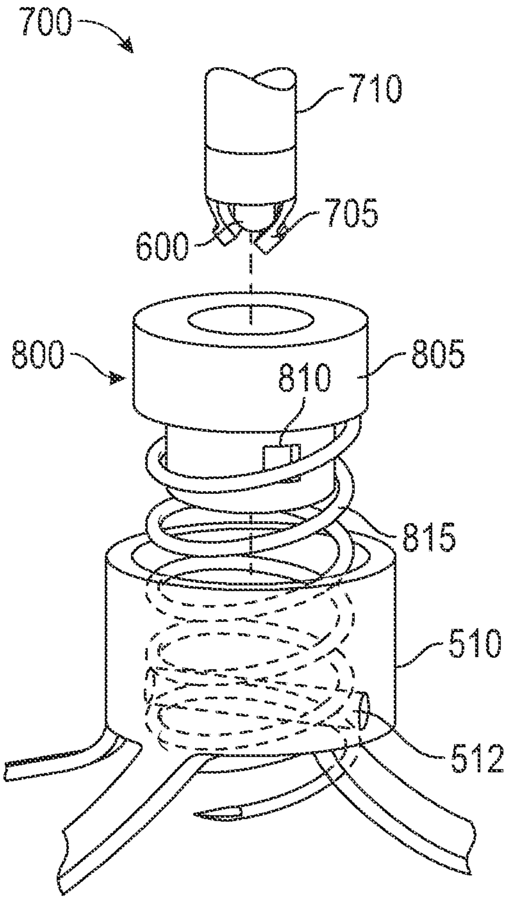
FIG. 8I illustrates an embodiment of an anchor that may be used to anchor the annular hub.

A support structure 505 made of a shape memory material can be advantageous. As the coaptation assistance device 500 opens, the coaptation assistance device 500 assumes the shape that was intended due to the action of the shape memory material. The shape of the coaptation assistance device 500, as described herein, can be intended to provide a new coaptation surface so that regurgitant flows are reduced or eliminated. Returning back to the explanation of the delivery and anchoring process, the delivery catheter 700, which can be still coupled to the annular hub 510 of the coaptation assistance device 500, may now be manipulated (rotationally and axially) to position the coaptation assistance device 500 appropriately over the posterior leaflet of the native valve. In an embodiment, the support structure 505 of the coaptation assistance device 500 may have features which may attach to the tissue. In some embodiments, these features are passive hooks. In some methods, these features engage the annulus such that the coaptation assistance device 500 may be held in place while anchoring is commenced. FIG. 8H shows the state of the delivery catheter 700 with the implant sheath 725 retracted and the shaft body 710 still coupled to the annular hub 510.

An embodiment of an anchor 800 is illustrated in detail in FIG. 81. The anchor 800 may be coupled to the delivery catheter 700 and/or the coaptation assistance device 500 in various ways. The annular hub 510 may have a cross-pin 512. The cross-pin 512 can provide a site about which a helical structure 815 of the anchor 800 may wrap around as shown. The anchor 800 can have a shoulder 805. The shoulder 805 may fit around the shaft body 710 of the delivery catheter 700. The shoulder 805 may have features such as windows 810 which can lock the distal locking tabs 705 of the delivery catheter 700. The distal locking tabs 705 of the delivery catheter 700 can lock when a pin, guidewire or a catheter such as the steerable catheter 600 is present within the shaft body 710 of delivery catheter 700. In some methods, the anchor 800 can be preloaded onto the coaptation assistance device 500 and locked in place with the delivery catheter 700 during the process of mounting the coaptation assistance device 500 onto the delivery catheter 700. This can occur prior to when the coaptation assistance device 500 is pulled into the implant sheath 725 and being readied for insertion into the femoral vein. Returning back to FIG. 8H, torque can be applied to the shaft body 710 such that the anchor 800 is driven into the tissue. To provide feedback whether the anchor 800 is secured appropriately, fluoroscopic markers may be present on the anchor 800. The markers may be located at the proximal end. These markers may inform the medical team about how far the anchor 800 may have travelled towards the annular hub 510 and may be informative about when the anchor 800 is securely in place. In some embodiments, to ensure that appropriate torque is applied, the torque level at the handle 730 may spike as the anchor 800 bottoms out on the annular hub 510. This increased torque level may be felt at the handle 730 providing feedback that appropriate torque has been applied. The central guidewire or the steerable catheter 600 can be retracted. This causes the distal locking tabs 705 to fall back from the windows 810 of the anchor 800, thus unlocking the delivery catheter 700 and the anchor 800. This can cause the releasing the coaptation assistance device 500. The delivery catheter 700 and steerable catheter 600 may now be completely retracted.

Commissure Anchoring

Figure 9A:
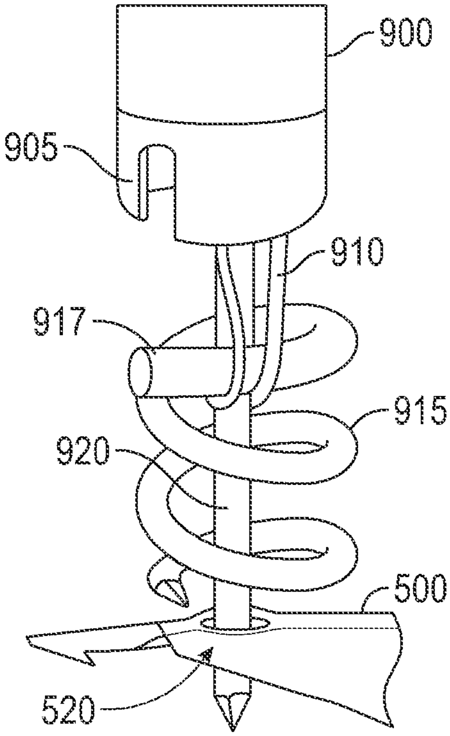
FIG. 9A illustrates a method to anchor the coaptation assistance device adjacent to the commissures via holes in the frame of the coaptation assistance device.

Several embodiments illustrate the commissure anchoring. One such embodiment is shown in FIG. 9A. The delivery catheter 700 (not shown) has been retracted and an anchor catheter 900 has been advanced through the femoral access. The anchor catheter 900 is torqueable. One or more anchor catheters 900 can be provided. The distal tip of the anchor catheter 900 may have one or more features to lock the anchors in place during the delivery of the anchor. In FIG. 9A, the distal tip has a cut-out 905 which may receive a portion of the helical anchor 915. The anchor catheter 900 may also have central pin 920. The central pin 920 can have a pointed end on the distal tip. In some embodiments, the central pin 920 can have the ability to be retracted.

Figure 9B:
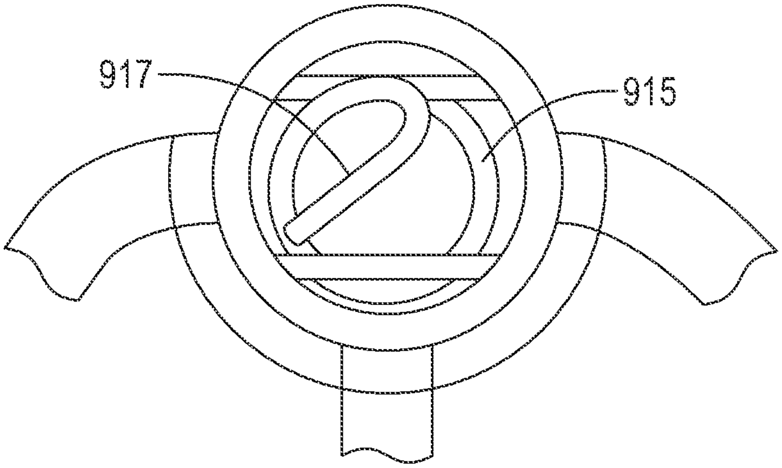
FIG. 9B illustrates the top view of the anchor and crossbar of FIG. 9A.

FIG. 9A shows a loop 910. The ends (not shown) of the loop 910 may travel to the handle of the anchor catheter 910 or some length therebetween such that the tension of the loop 910 may be controlled. The loop 910 go over a crossbar 917 or other portion which forms the proximal part of the helical anchor 915. The top view of the helical anchor 915 with the crossbar 917 is shown in FIG. 9B. While outside the body, prior to entry into the trans-septal sheath (not shown), the helical anchor 915 may be placed adjacent to the central pin 920. The loop 910 may be arranged in such a manner that when tension is applied to the loop 910, the loop 910 keeps the helical anchor 915, and the central pin 920 locked in place. In FIG. 9A, this arrangement is retracted so that the cutouts 905 receive the proximal portion of the helical anchor 915. Keeping the loop 910 in tension, the entire arrangement is advanced into the trans-septal sheath.

Once in the desired location within the body, the anchor catheter 900 is adjusted so that the distal end of the anchor catheter 900 is positioned over a commissure hole 520. The central pin 920 and the helical anchor 915 are advanced such that the central pin 920 first pierces the tissue after going through a commissure hole 520. Torque is applied to the anchor catheter 900 and the helical anchor 915 pierces the tissue. The helical anchor 915 anchors the support structure 505 or frame of the coaptation assistance device 500 to the tissue. After the helical anchor 915 is in place, the central pin 920 is retracted. The retraction of the central pin 920 can allows the loop 910 to slip over the crossbar 917 of the helical anchor 915, thereby releasing the anchor 915. This process can be repeated for the other commissure site to anchor both extreme projections of the coaptation assistance device 500.

Alternative Anchoring Techniques

Figure 10A:
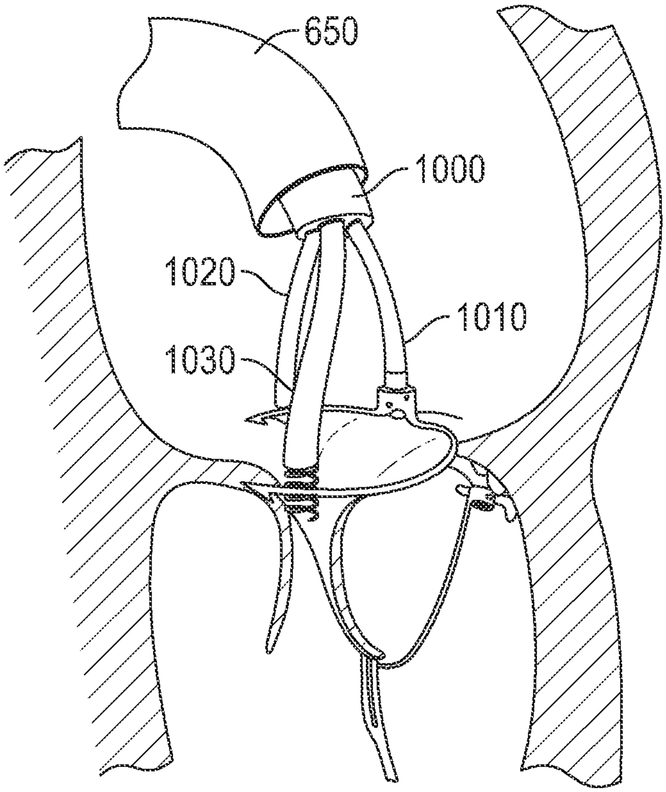
FIG. 10A illustrates another embodiment of the delivery catheter having multiple lumens and connections to the implant.
Figure 10B:
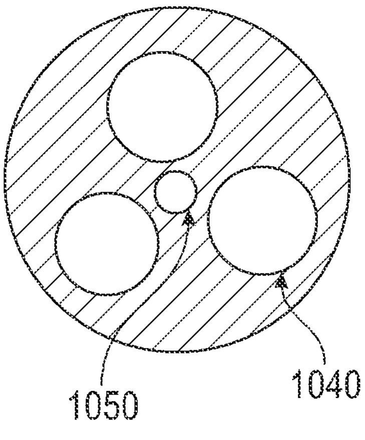
FIG. 10B illustrates a cross section of the delivery catheter shown in FIG. 10A.

FIG. 10A shows an alternative anchoring technique in another embodiment. In this embodiment, a delivery catheter 1000 may have multiple lumens 1040. The delivery catheter 1000 may have a cross-section as shown in FIG. 10B. The lumens 1040 may carry individual torqueable drive shafts. Each drive shaft can be locked onto an anchor as the case is for shafts 1020 and 1030 or onto the annular hub 510 as is shown for shaft 1010. Each torqueable shaft 1010, 1020, 1030 may have the design of the anchor catheter 900 illustrated in FIG. 9A. The delivery catheter 1000 may have a central lumen 1050 through which a guidewire or the steerable catheter 600 may pass. The multiple torqueable drive shafts 1010, 1020, 1030, a guidewire or the steerable catheter 600 along with the coaptation assistance device 500 can all be loaded and retracted into the implant sheath of the delivery catheter 1000 prior to entry into the trans-septal sheath. This entire arrangement can be advanced and the same procedure as explained herein can be followed to place the coaptation assistance device 500. The advantageous aspect of this arrangement is that the anchoring process may be accomplished without the need to retract the anchor catheter multiple times, reloading the anchors and reentering the body.

Alternative Designs for Anchors

Figure 11A:
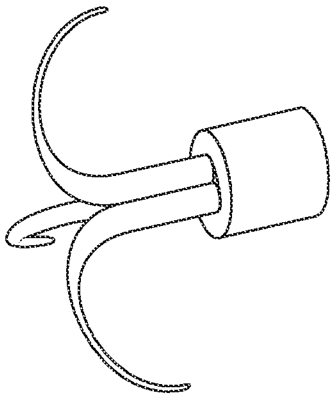
FIG. 11A-B illustrate various alternative embodiments of anchors.
Figure 11B:
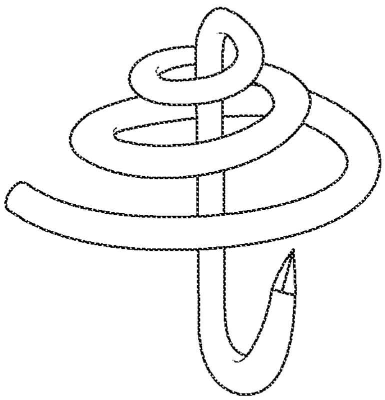
Figure 11C:
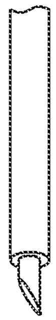
FIG. 11C illustrates a delivery tube through which the anchors 11A and 11B may be delivered.

While some anchors have been described herein, other alternative embodiments are contemplated. FIG. 11A shows an anchor with grappling hooks. FIG. 11B shows an anchor that resembles an umbrella. In both embodiments, the anchors may be made of a shape memory material. In both embodiments, the anchors may be loaded into a delivery catheter such as the delivery catheter illustrated in FIG. 11C.

Locking mechanisms such as those described herein may be used to lock the anchors to the delivery catheter. The delivery catheter may have a pointed end so that the delivery catheter may be guided to an appropriate location and initially pierce the tissue. After the delivery catheter is placed at an appropriate location and the initial piercing is accomplished, one or more of the anchors may be advanced and set in place. This step is followed by unlocking and retracting the delivery catheter.

Figure 11D:
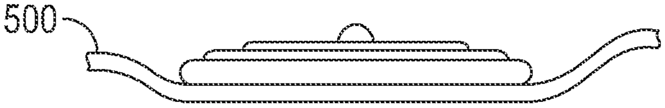
FIG. 11D illustrates how the anchor of FIG. 11B may appear after the anchoring process is completed.

FIG. 11D is an illustration of how the umbrella anchor of FIG. 11B may look after it has been set into the tissue to anchor the coaptation assistance device 500. Due to the natural unstressed shape of the anchor, when deployed in the tissue over the coaptation assistance device 500, the deformed shape would have an effective spring-force on the face of the coaptation assistance device 500, ensuring a good foothold.

Spineless Implants

The coaptation assistance device 500 described in FIGS. 5A-F can include the support structure 505. The support structure 506 can be made of shape memory material as described herein. In some embodiments of the coaptation assistance device, another configuration is contemplated. This configuration can be called the spineless coaptation assistance device to indicate that the support structure is removed after placement of the coaptation assistance device in the heart. Both types of coaptation assistance devices can have certain advantages. The spineless coaptation assistance device may be advantageous due to fewer components and materials and no possible metal fatigue.

Figure 12:
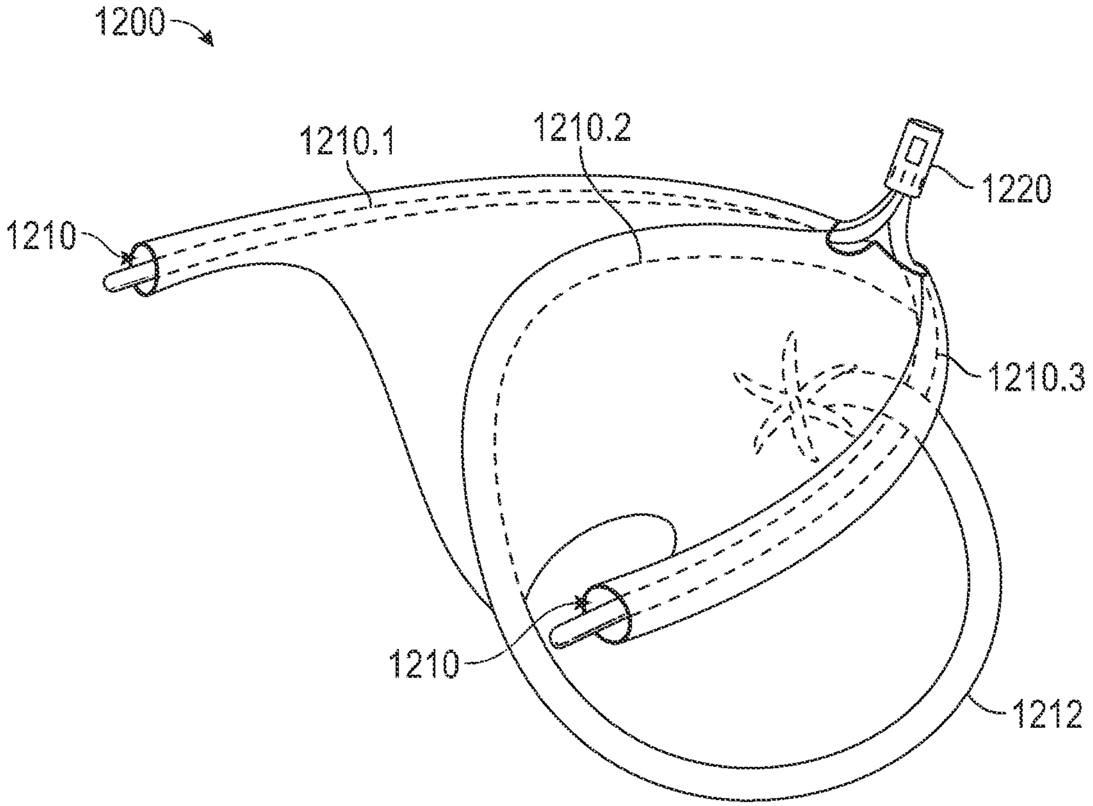
FIG. 12 illustrates a spineless implant design (figure is shown with a structure 1220 which is later withdrawn from the implant).

FIG. 12 shows an embodiment of the spineless coaptation assistance device 1200. The spineless coaptation assistance device 1200 can include a tube or a passageway 1210. The passageway 1210 can be placed around the annular edge. This passageway 1210 can be called the annular tube. The spineless coaptation assistance device 1200 can include a tube or passageway 1212 along the ventricular projection. This passageway 1212 can be called the ventricular tube.

The profile of the passageway 1210 can be shown towards the ends of the annular tube. Although a circular profile is illustrated, the tubes or passageways 1210, 1212 may have other profiles including but not limited to oval and flat.

The support structure 1210.1, 1210.2, 1210.3 is shown by dotted lines except at the annular edges where the support structures 1210.1 and 1210.3 protrude. The support structure 1210.1, 1210.2, 1210.3 may have three distinct sections, where 1210.1 and 1210.3 are placed in the annular tube and 1210.2 is placed in the ventricular tube. The support structure 1210.1, 1210.2, 1210.3 can be coupled within a spine hub 1220. In some embodiments, the support structure 1210.1, 1210.2, 1210.3 may be distinct and separate sections. In some embodiments, the support structure 1210.1, 1210.2, 1210.3 may be joined together by using one of various methods such as, but not limited to, crimping and laser welding. This arrangement of the support structure 1210.1, 1210.2, 1210.3 and the coaptation assistance device 1200 allows the support structure 1210.1, 1210.2, 1210.3 to be extracted from the coaptation assistance device 1200. In some methods, the support structure 1210.1, 1210.2, 1210.3 is extracted by applying a pulling force on spine hub 1220. More detail about the coaptation assistance device 1200, and the procedure to deliver and anchor the coaptation assistance device 1200, will be provided herein.

Delivery Procedure of the Spineless Implant

Figure 13A:
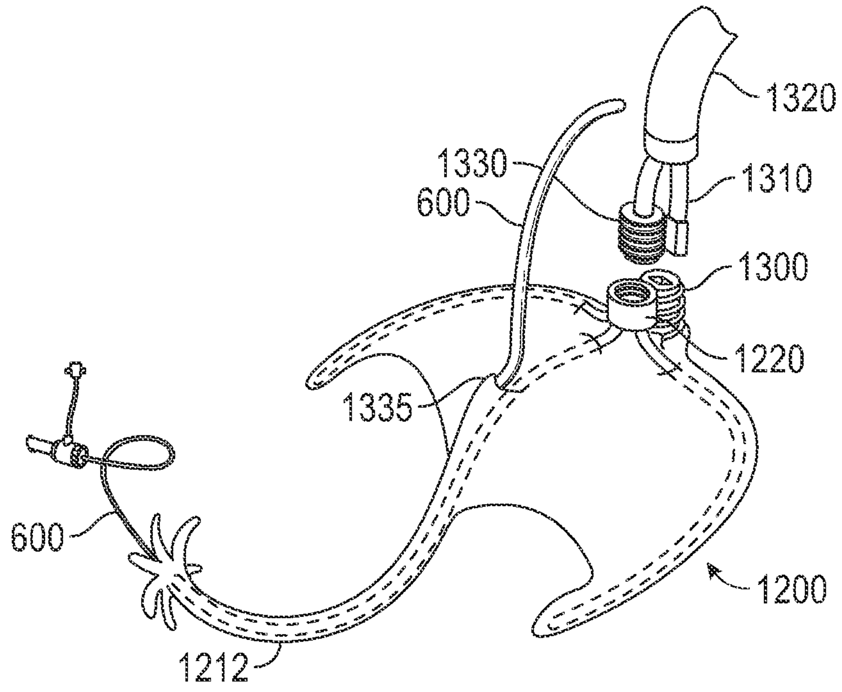
FIG. 13A-B illustrate the initial stages of the delivery procedure for the spineless implant.
Figure 13B:
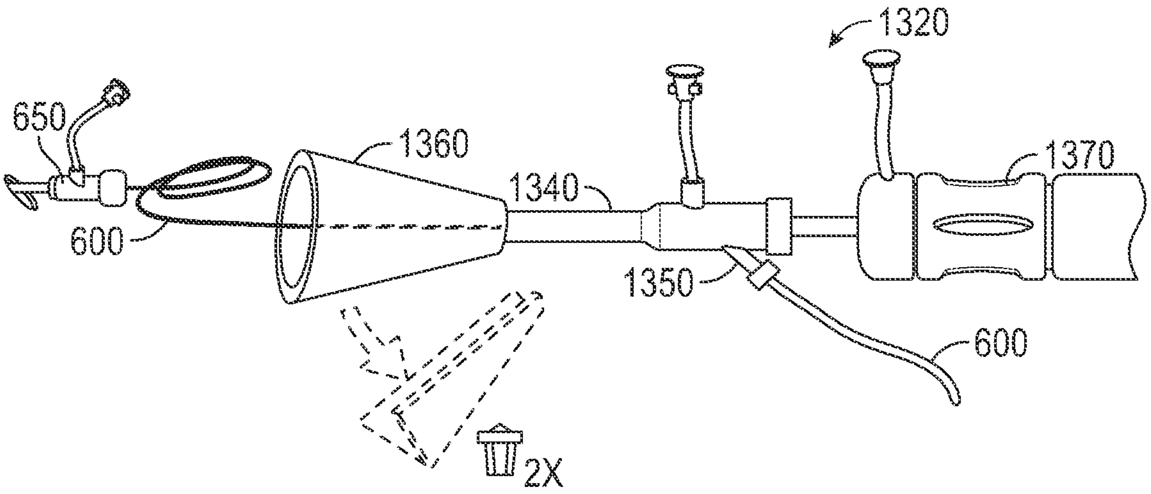

FIGS. 13A and 13B illustrate the delivery procedure of the coaptation assistance device 1200. FIG. 13A shows the coaptation assistance device 1200 of FIG. 12. FIG. 13A shows an additional feature, an anchor site 1300. This anchor site 1300 will be described in greater detail herein.

The steerable catheter 600 can inserted into the coaptation assistance device 1200. The steerable catheter 600 can be inserted from the distal tip of the ventricular projection 1212. The steerable catheter 600 can exits from an exit aperture 1335. A delivery catheter 1320 can be provided. The delivery catheter 1320 can include a torqueable shaft 1310. The delivery catheter 1320 can include a hub locking feature 1330 that couples with a hub anchor 1300. In FIG. 13A, the hub locking feature 1330 is shown as a screw. Other locking mechanisms explained herein may be utilized.

FIG. 13B illustrates more detail with regard to the delivery catheter 1320. The distal tip of the delivery catheter 1320 can include a funnel 1360. Proximal to the funnel 1360, an implant introducer 1340 may be present. At the very proximal end, the delivery catheter 1320 may have a handle 1370.

The steerable catheter 600 can be threaded through the coaptation assistance device 1200 as described herein. The funnel 1360 can be inserted on to the distal tip of the delivery catheter 1320. The coaptation assistance device 1200 can be locked in place using the locking feature 1330, such that the hub anchor 1300 is connected to the torqueable shaft 1310.

The steerable catheter 600 can be threaded through an angled side port 1350 on the implant introducer 1340. The coaptation assistance device 1200 and the steerable catheter 600 can be pulled through the funnel 1360 by retracting the delivery catheter 1320. With continued retraction, the coaptation assistance device 1200 will fold upon itself within the implant introducer 1340. Once the implant is in the introducer 1340, the funnel 1360 is removed and discarded. The funnel 1360 may be designed such that it may be easily removed. Designs for the funnel include but are not limited to the peel away design (shown previously in FIGS. 8A-8C) or a clamshell design (FIG. 13B).

The delivery catheter 1320 along with the implant introducer 1340 can be advanced over the steerable catheter 600 until the implant introducer 1340 couples with the hub of the trans-septal sheath 650. At this point, the implant introducer 1340 may not be able to advance further but the coaptation assistance device 1200 itself can be advanced into the trans-septal sheath. The next several steps are similar to that shown in FIGS. 8E through 8G, except in this example, no implant sheath is used. The coaptation assistance device 1200 is placed over the posterior leaflet and the ventricular projection 1212 is placed in the left ventricle. The steerable catheter 600 can be retracted allowing the ventricular projection 1212 to curl or coil under P2. Once the ventricular projection 1212 is anchored, the hub anchor 1300 can be rotated or otherwise activated. The hub anchor 1300 can anchor the proximal side of the coaptation assistance device 1200 to the annulus. The torqueable shaft 1310 can retracted. After additional anchoring, which will be explained herein, the hub locking feature 1330 is retracted pulling the support structure 1210.1, 1210.2, 1210.3 along with it. The coaptation assistance device 1200 may now be operational in the left heart without the support structure 1210.1, 1210.2, 1210.3.

Anchoring Procedure for Spineless Implant

Figure 14A:
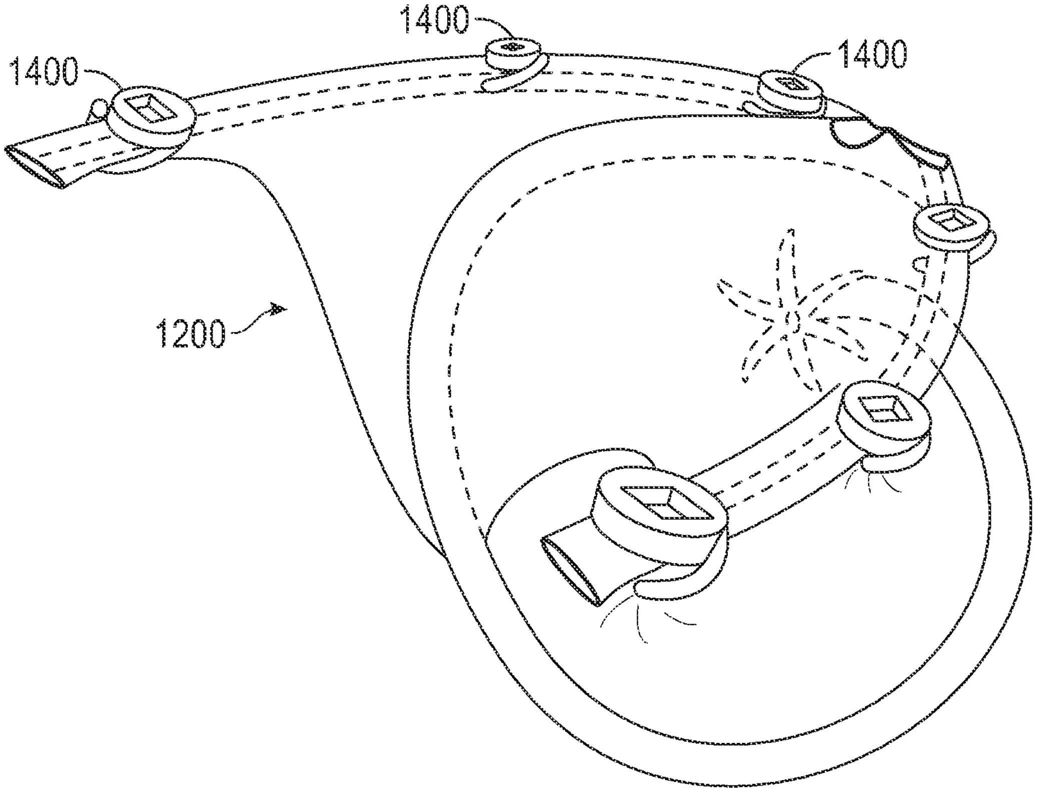
FIG. 14A-B illustrate various types of anchoring methods for spineless implants.
Figure 14B:
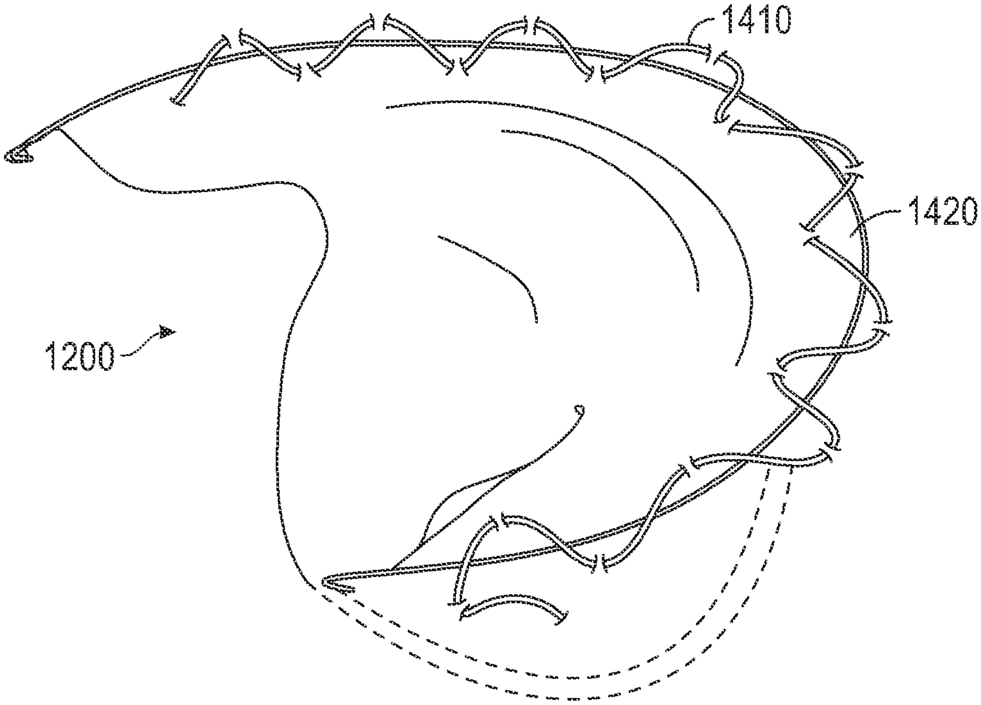

FIG. 14A shows an embodiment for anchoring the coaptation assistance device 1200. As no rigid structure such as the support structure 1210.1, 1210.2, 1210.3 can be present after implantation, the coaptation assistance device 1200 may need additional anchors. In some embodiments, the coaptation assistance device 1200 may utilize closely spaced anchors. In some embodiments, the coaptation assistance device 1200 may utilize additional and closely spaced anchors than a similar coaptation assistance device with a support structure 505, described herein. FIG. 14A shows an embodiment of anchors 1400, which may be used to couple the coaptation assistance device 1200 and the tissue. FIG. 14B shows another embodiment. In FIG. 14B, a suture or tape 1410 is used to "sew" the coaptation assistance device 1200 to the tissue. The suture or tape 1410 may be made of one of several materials including, but not limited to, polypropylene or nylon. Several embodiments describing how the multiple anchors are placed are now explained herein.

Figure 15A:
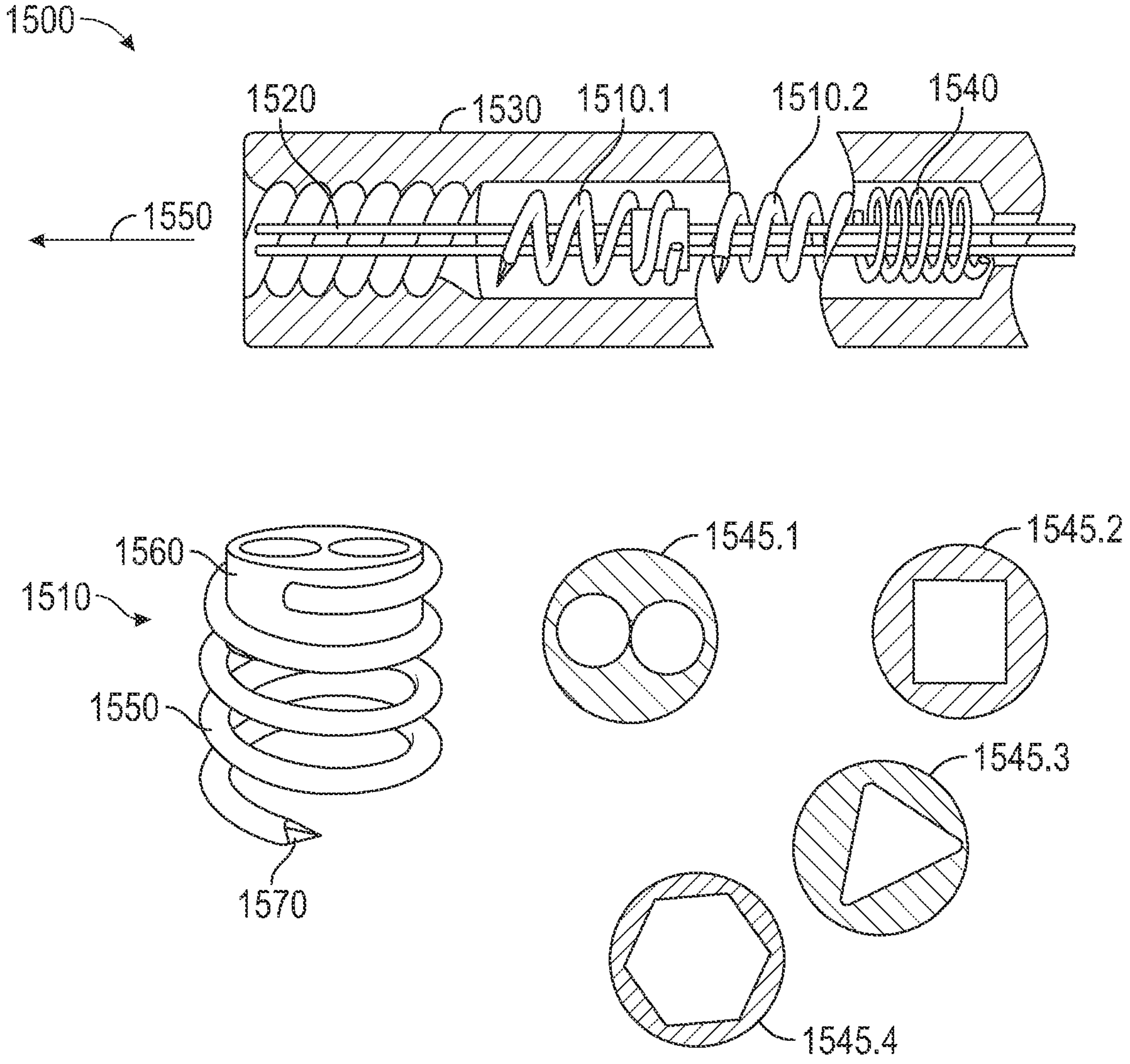
FIG. 15A illustrates an embodiment of an anchor catheter enabled to deliver multiple anchors. This figure also illustrates multiple anchor designs.

FIG. 15A shows an embodiment of an anchor catheter 1500 that delivers multiple anchors. Several anchors 1510, including anchor 1510.1 and anchor 1510.2, are stacked within the anchor catheter 1500. Although FIG. 15A shows two anchors 1510.1 and 1510.2 stacked within the anchor catheter 1500, more or fewer anchors may be stacked. Each anchor 1510 may include a coil section 1550. The coil section 1550 can include a pointed end 1570. The anchor 1510 may include an anchor head 1560. The anchor head 1560 may have one of several cross sections shown by 1545.1, 1545.2, 1545.3 and 1545.4 in FIG. 15A. Other cross sections are possible.

To initially load the anchor catheter 1500, the anchors 1510 are loaded onto a central shaft 1520 of the anchor catheter 1500. The central shaft 1520 and the anchors 1510 may have a matching cross section such that the anchors 1510 may be rotationally coupled to the central shaft 1520. At the proximal end of the anchor catheter 1500, a spring 1540 can be included. This spring 1540 provides a pushing force such that as the central shaft 1520 is rotated, the anchors 1510 exit the distal end of the anchor catheter 1500 in the direction of arrow 1550. As the anchors 1510 exit, the anchor 1510 can engage with the coaptation assistance device 1200 and the tissue to couple the coaptation assistance device 1200 to the tissue. The rotation of the central shaft 1520 may be controlled by an operator such as a doctor. In some embodiments, the central shaft 1520 is coupled to a torqueable wire (not shown) which may be coupled at the proximal end to a handle (not shown). In some embodiments, the torqueable wire may be controlled manually. In some embodiments, the torqueable wire may be controlled via an electric motor. Other methods to impart a rotational motion to the central shaft 1520 are contemplated. A feature that is not shown in the FIG. 15A is the ability to steer and position the distal end of the anchor catheter 1500. As one anchor 1510 is delivered, the distal tip may need to be repositioned to deliver the next anchor 1510. A steering mechanism such as pull wires may be included to steer the distal tip of the anchor catheter 1500.

Figure 15B:
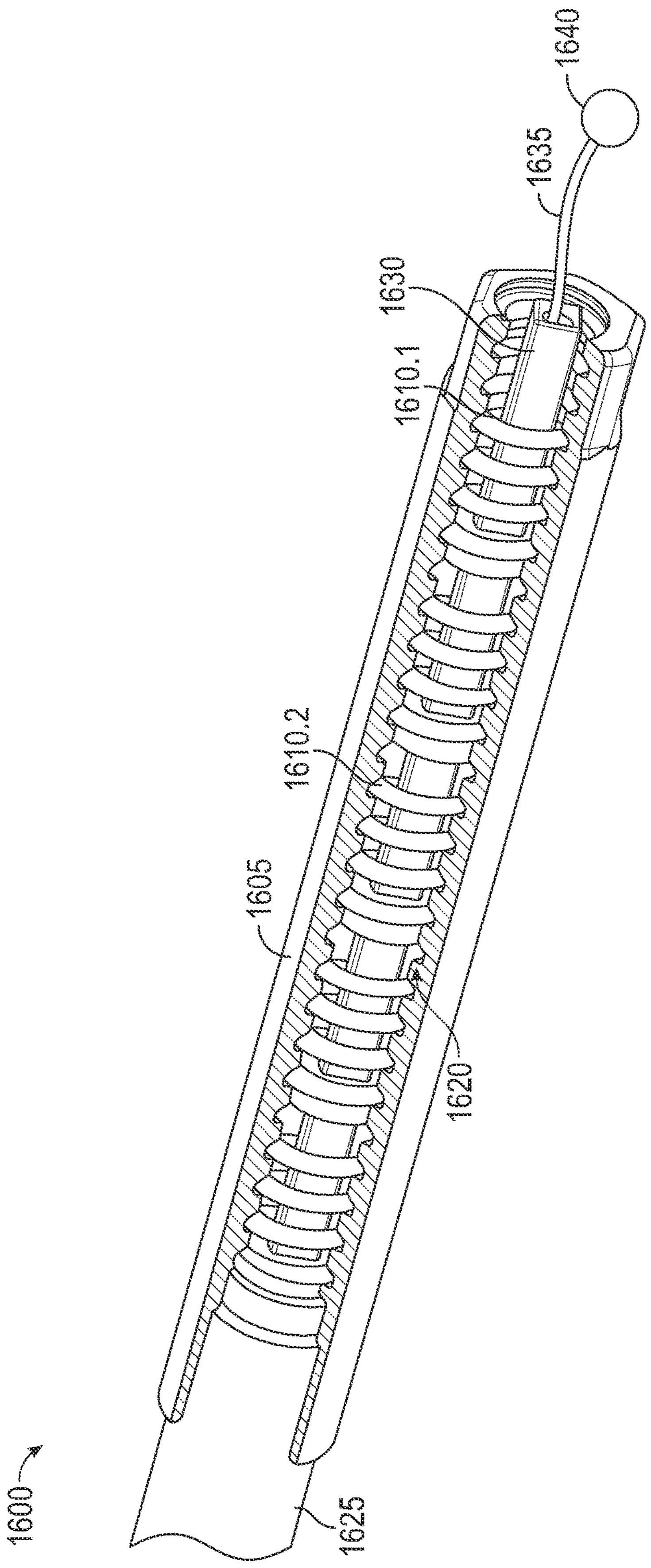
FIG. 15B illustrates another embodiment of an anchor catheter enabled to deliver multiple anchors.

FIG. 15B shows another embodiment of an anchor catheter 1600 that delivers multiple anchors. FIG. 15B shows only the distal tip of an anchor catheter 1600. The anchor catheter 1600 can include multiple anchors 1610 such as 1610.1 and 1610.2. Although the anchor catheter 1600 shows five anchors, more or fewer anchors 1610 may be loaded at any one time. The anchor catheter 1600 may have a central shaft 1630. The anchor catheter 1600 can include threads such as 1620 on the inside of the housing 1605. These threads 1620 can house the coils of the anchors 1610 as shown. To initially load the anchor catheter 1600, the anchors 1610 are inserted into the housing 1605. The anchors 1610 are inserted onto the central shaft 1630. As described previously, the cross-section of the central shaft 1630 may match the cross-section of the anchors 1610 so that the anchors 1610 may be mounted on the central shaft 1630. The rotation of the central shaft 1630 may be controlled by a torqueable cable (not shown) which may couple the central shaft 1630 to a handle (not shown) of the anchor catheter 1600. The operator such as a doctor may control the rotation. In some embodiments, the torqueable wire may be controlled manually.

In some embodiments, the torqueable wire may be controlled via an electric motor. As the central shaft 1630 rotates, the threads will force the anchors 1610 to exit the anchor catheter 1600 and engage with the coaptation assistance device 1200 and the tissue to couple the coaptation assistance device 1200 and the tissue together. The anchor catheter 1600 may also have pull wires to steer the distal tip of the anchor catheter 1600 so that as one anchor 1610 is delivered, the anchor catheter 1600 may be positioned to deliver the next anchor 1610.

Figure 15C:
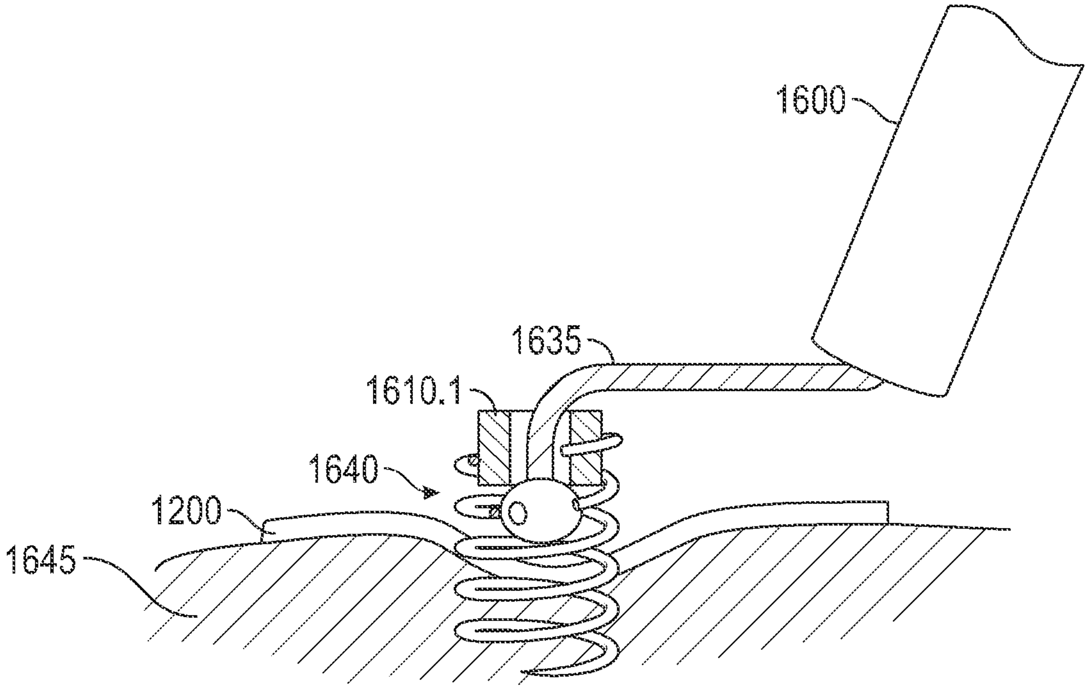
FIG. 15C-D illustrate how the anchors in 15B may be coupled to the tissue.
Figure 15D:
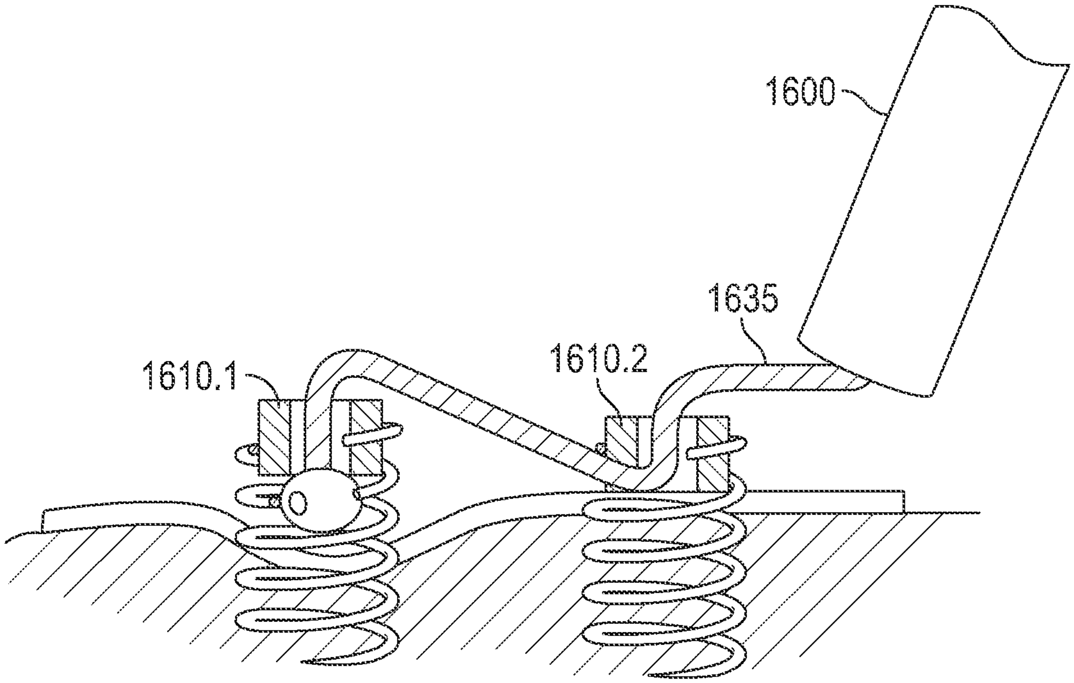

FIG. 15B illustrates a central suture 1635. The central suture 1635 can include a ball 1640 coupled to the end of the central suture 1635. FIGS. 15C and 15D illustrate how the central suture 1635 and ball 1640 may be used. The ball 1640 can sit in a pocket inside the first anchor 1610.1. The central suture 1635 can connect the first anchor 1610.1 to the second anchor 1610.2 and others anchors 1610 (not shown in the figure). This arrangement may provide the ability to use the central suture 1635 as a guide wire to return back to an anchor 1610 after the anchor 1610 has been screwed into the tissue 1645. The operator may wish to return to the anchor 1610 to reposition or adjust the anchor 1610. In addition, if one or more anchors 1610 came loose, the central suture 1635 may provide a tether for the loose anchors 1610, therefore preventing embolic events.

Figure 16A:
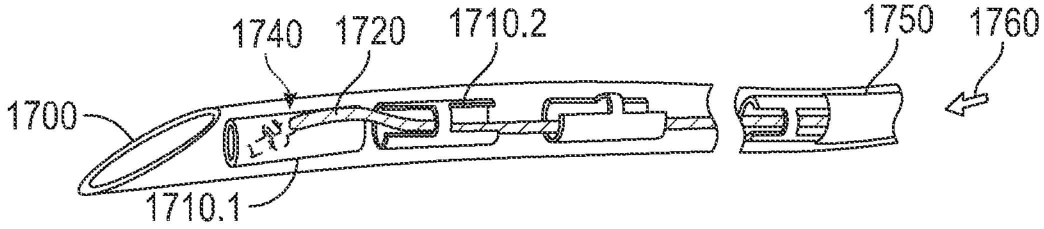
FIG. 16A illustrates another embodiment of an anchor catheter enabled to deliver multiple anchors.
Figure 16B:
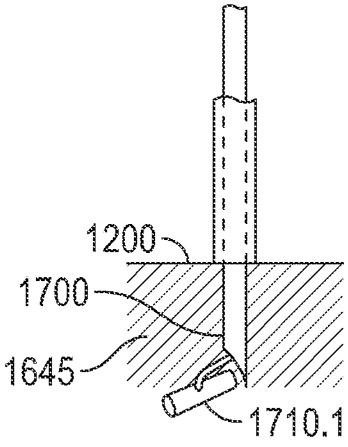
FIG. 16B-C illustrate how the tool in FIG. 16A may be used to deliver multiple anchors.
Figure 16C:
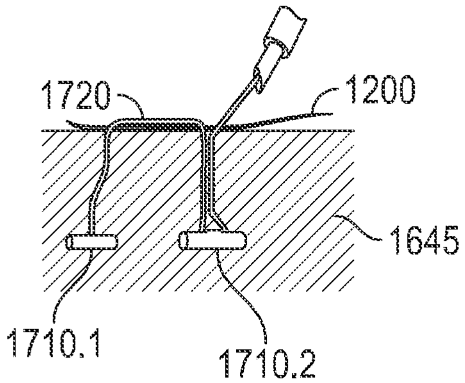

FIG. 16A-C shows another embodiment of an anchor catheter 1700 that delivers multiple anchors. The anchor catheter 1700 can have a hollow shaft. The hollow shaft can be pointed at the distal end which may be used to pierce the coaptation assistance device 1200 and tissue. Multiple anchors 1710 such as 1710.1, 1710.2 may be arranged within the hollow shaft of the anchor catheter 1700. The anchors 1710 can be hollow barrels.

A suture 1720 may be threaded through the anchors 1710 as shown. The suture 1720 may be secured to the first anchor 1710.1 by arranging the suture 1720 to exit the second anchor 1710.2 and enter the first anchor 1710.1 through a side aperture 1740. The suture 1720 may then be secured by means of a knot as depicted in dotted lines within the first anchor 1710.1. The suture 1720 in the other anchors 1710, except the first anchor 1710.1, may appear as illustrated for the anchor 1710.2. The anchors 1710, except the first anchor 1710.1 have a portion of their walls cut out. The cut outs can aids in better trapping the anchors within the tissue, similar to a toggle-bolt. At the proximal end of the anchor catheter 1700, a feature such as a pusher tube 1750 may be present to cause the anchors 1710 such as 1710.1 and 1710.2 to exit the anchor catheter 1700 at the distal end. The pusher 1750 may be attached to a handle (not shown) so as to enable an operator such as a doctor to deposit one or more anchors 1710 when appropriate. The arrow 1760 indicates the direction of the push.

FIG. 16B-C illustrates how the anchor catheter 1700 of FIG. 16A may operate. In FIG. 16B, the anchor catheter 1700 is advanced through the coaptation assistance device 1200 through a slot such as described by 520 in FIG. 5A. The anchor catheter 1700 then pierces the tissue 1645. The operator pushes the first anchor 1710.1 out of the anchor catheter 1700, depositing the anchor 1710.1 within the tissue. Once the first anchor 1710.1 is deposited, the rest of the anchors 1710 are deposited as illustrated in FIG. 16C. In FIG. 16C, the anchor catheter 1700 is pulled out of the tissue after depositing the first anchor 1710.1 in order to enter a second location. At the second location, the anchor catheter 1700 can deposit the second anchor 1710.2. This process is continued until desired to secure the coaptation assistance device 1200 to the tissue. After the last anchor 1710 is delivered, a cutter (not shown) can be advanced inside the anchor catheter 1700 to cut the suture 1720, leaving behind the anchors 1710.

In some embodiments, the anchors 1710 may be radio opaque or they may be covered by a radio graphic marker. During the process of delivery of the anchors 1710, the radio opaque markers may be visualized if a fluoroscope is used. This may help in spacing the anchors 1710 around the annulus of the coaptation assistance device 1200.

In some embodiments, the MR is assessed while securing the coaptation assistance device 1200 and the pitch and/or the location of the sewing action is determined according to the presence or absence of the MR.

Spineless Implant with Annular Tube

Figure 17A:
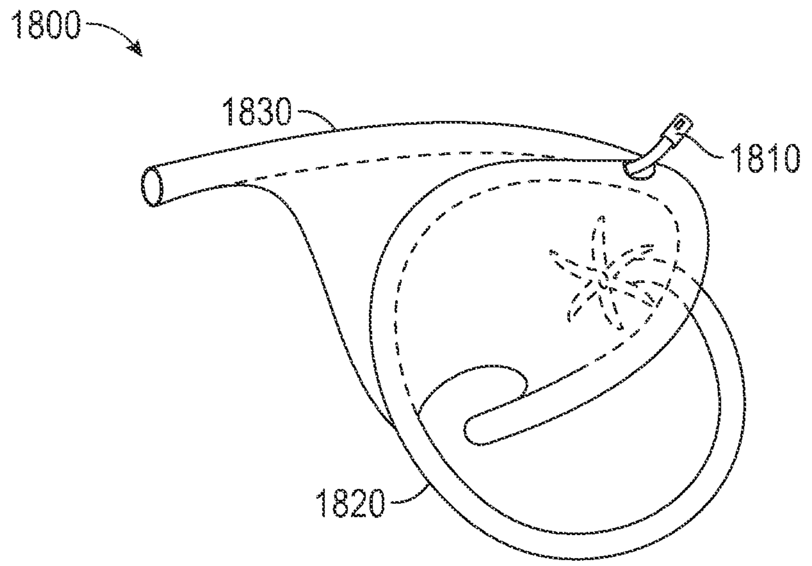
FIG. 17A illustrates another embodiment of a spineless implant.
Figure 17B:
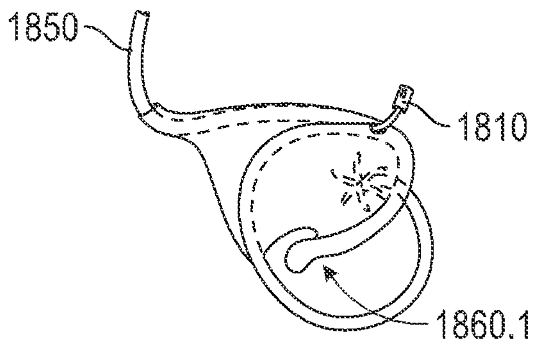
FIG. 17B-E illustrate how the embodiment of FIG. 17A may be anchored.

FIG. 17A illustrates another embodiment of a spineless coaptation assistance device 1800. In this embodiment, the support structure 1810 may only traverse down the ventricular projection 1820. A tube or passageway 1830 may be present around the annular edge of the coaptation assistance device 1800. Instead of utilizing a support structure 1810 to maintain the shape of the coaptation assistance device 1800, an anchor catheter 1850 can be inserted into the tube 1830 as shown in FIG. 17B. In FIG. 17B, the anchor catheter 1850 can be a deflectable anchor catheter.

Figure 17C:
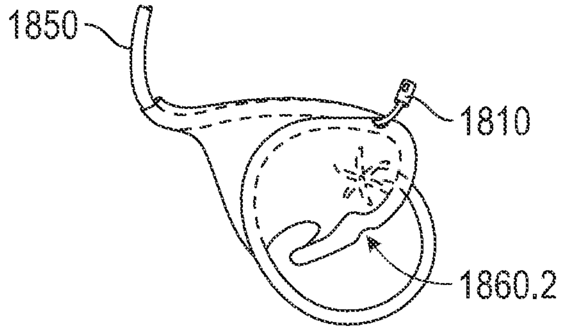
Figure 17D:
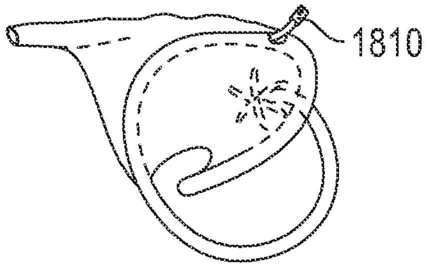
Figure 17E:
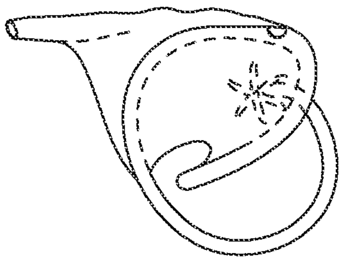

FIG. 17B also shows a first site 1860.1 where an anchor such as that described by 1560 in FIG. 15A can be delivered. At this site 1860.1 and all anchor sites 1860, the tip of the anchor catheter 1850 would be deflected by controls located outside the body. The anchors (not shown) may be delivered securing the coaptation assistance device 1800 to the tissue. The tip of the anchor catheter 1850 may be radio opaque which may then be visualized during the anchor delivery process. The visualization of the tip may be utilized to locate the anchors around the annulus of the coaptation assistance device 1800. FIG. 17B illustrates a first anchor location 1860.1 and FIG. 17C illustrates a second anchor location 1860.2. After the appropriate number of anchors are delivered, the anchor catheter 1850 is retracted completely as shown in FIG. 17D. Finally the support structure 1810 can be removed as shown in FIG. 17E.

In a variation of the embodiment shown in FIGS. 17A-17E, the support structure 1810 may not be limited only to the ventricular projection; it may also be inserted through the annular tube 1830 such that a desired shape may be maintained. The support structure can be a shape memory material. Utilizing a support structure around the annular tube 1830 may result in an anchor catheter which may have relatively simpler control mechanisms compared to the anchor catheter 1850 used for the coaptation assistance device 1800 described in FIG. 17A.

It is contemplated that various combinations or subcombinations of the specific features and aspects of the embodiments disclosed above may be made and still fall within one or more of the inventions. Further, the disclosure herein of any particular feature, aspect, method, property, characteristic, quality, attribute, element, or the like in connection with an embodiment can be used in all other embodiments set forth herein. Accordingly, it should be understood that various features and aspects of the disclosed embodiments can be combined with or substituted for one another in order to form varying modes of the disclosed inventions. Thus, it is intended that the scope of the present inventions herein disclosed should not be limited by the particular disclosed embodiments described above. Moreover, while the invention is susceptible to various modifications, and alternative forms, specific examples thereof have been shown in the drawings and are herein described in detail. It should be understood, however, that the invention is not to be limited to the particular forms or methods disclosed, but to the contrary, the invention is to cover all modifications, equivalents, and alternatives falling within the spirit and scope of the various embodiments described and the appended claims. Any methods disclosed herein need not be performed in the order recited. The methods disclosed herein include certain actions taken by a practitioner; however, they can also include any third-party instruction of those actions, either expressly or by implication. For example, actions such as “inserting a coaptation assist body proximate the mitral valve” includes “instructing the inserting of a coaptation assist body proximate the mitral valve.” The ranges disclosed herein also encompass any and all overlap, subranges, and combinations thereof. Language such as “up to,” “at least,” “greater than,” “less than,” “between,” and the like includes the number recited. Numbers preceded by a term such as “approximately”, “about”, and “substantially” as used herein include the recited numbers, and also represent an amount close to the stated amount that still performs a desired function or achieves a desired result. For example, the terms "approximately", "about", and "substantially" may refer to an amount that is within less than 10% of, within less than 5% of, within less than 1% of, within less than 0.1% of, and within less than 0.01% of the stated amount.

What is claimed is:

1. An anchoring system comprising:

a coaptation assist device comprising a coaptation assist body, wherein the coaptation assist body comprises an arcuate, peripheral superior edge, a first lateral edge, a second lateral edge, and an inferior edge, wherein the arcuate, peripheral superior edge is greater than the inferior edge, wherein the coaptation assist device comprises a hub and a plurality of struts extending from the hub, wherein the hub is positioned closer to the arcuate, peripheral superior edge than the inferior edge, wherein at least one strut of the plurality of struts comprises a first zone that is generally oriented substantially parallel to the longitudinal axis of a coaptation assist body and a second zone that is generally oriented substantially perpendicular to the longitudinal axis of the coaptation assist body; and a helical tissue anchor, wherein the hub is configured to receive the helical tissue anchor, wherein the helical tissue anchor is configured to be rotated relative to the hub, wherein the helical tissue anchor is configured to secure the coaptation assist device to an annulus of a mitral valve.

2. The anchoring system of claim 1, wherein the coaptation assist body comprises a first concave surface configured to restrain a posterior leaflet of the mitral valve.

3. The anchoring system of claim 1, wherein the coaptation assist body comprises a second convex surface configured to contact an anterior leaflet of the mitral valve.

4. The anchoring system of claim 1, wherein the coaptation assist body is configured to provide a new coaptation surface over a posterior leaflet such that the backward flow of blood is minimized or eliminated.

5. The anchoring system of claim 1, wherein the helical tissue anchor comprises a fluoroscopic marker.

6. The anchoring system of claim 1, wherein the plurality of struts comprises a shape memory material.

7. The anchoring system of claim 1, wherein the coaptation assist body comprises polyurethane.

8. The anchoring system of claim 1, wherein the coaptation assist body comprises pericardium.

9. An anchoring system comprising:

a coaptation assist device, wherein the coaptation assist device comprises a shape memory structure comprising a hub and a plurality of struts, wherein the coaptation assist body comprises a biocompatible membrane coupled to the shape memory structure, wherein the coaptation assist device comprises a proximal end greater than a distal end, wherein the coaptation assist device tapers along a first lateral edge and a second lateral edge toward the distal end, wherein the hub is placed on a proximal side of the coaptation assist device; and a helical tissue anchor, wherein the hub is configured to receive the helical tissue anchor, wherein the helical tissue anchor is configured to be rotated relative to the hub, wherein the helical tissue anchor is configured to secure the coaptation assist device to an annulus of a mitral valve.

10. The anchoring system of claim 9, wherein the shape memory structure comprises Nitinol.

11. The anchoring system of claim 9, wherein the shape of the plurality of struts is configured to be retained after implantation.

12. The anchoring system of claim 9, further comprising a torque shaft configured to rotate the helical tissue anchor, wherein a torque level at a handle of the torque shaft spikes as the helical tissue anchor bottoms out on the hub.

13. The anchoring system of claim 9, wherein the coaptation surface is configured to be disposed toward an anterior leaflet of the mitral valve.

14. An anchoring system comprising:

a coaptation assist device comprising a coaptation assist body, wherein the coaptation assist device comprises a hub and a plurality of struts, wherein at least one strut of the plurality of struts comprises a first zone that is generally oriented downward and substantially parallel to the longitudinal axis of a coaptation assist body and a second zone that is generally oriented substantially perpendicular to the longitudinal axis of the coaptation assist body, wherein the second zone has a greater dimension transverse to the longitudinal axis of the coaptation assist body than the first zone, wherein the hub extends directly from the second zone, wherein the coaptation assist device is configured to maintain its shape and functionality as the heart contracts and dilates and exerts pressure on the coaptation assistance device; and a helical tissue anchor, wherein the hub is configured to receive the helical tissue anchor, wherein the helical tissue anchor is configured to be rotated relative to the hub, wherein the helical tissue anchor is configured to secure the coaptation assist device to an annulus of a mitral valve.

15. The anchoring system of claim 14, wherein the plurality of struts comprises a shape memory metal or polymer.

16. The anchoring system of claim 14, wherein the helical tissue anchor is configured to be rotated by a torque shaft.

17. The anchoring system of claim 14, wherein the coaptation assist device is configured to be positioned over a posterior leaflet of the mitral valve.

18. The anchoring system of claim 14, further comprising an additional helical anchor.

19. The anchoring system of claim 18, further comprising an anchor catheter comprising one or more features to lock the additional helical anchor in place during delivery of the additional helical anchor.

* * * * *